United States Patent
Wang et al.

(10) Patent No.: US 10,695,347 B2
(45) Date of Patent: Jun. 30, 2020

(54) PYRIMIDINE DERIVATIVE AND USE THEREOF

(71) Applicants: Hubei Bio-Pharmaceutical Industrial Technological Institute Inc., Wuhan (CN); Humanwell Healthcare (Group) Co., Ltd., Wuhan (CN)

(72) Inventors: Xuehai Wang, Wuhan (CN); Yong Xu, Wuhan (CN); Xijun Sheng, Wuhan (CN); Xiaolin Zhang, Wuhan (CN); Hangui Xia, Wuhan (CN); Zhongwen Yang, Wuhan (CN); Yang Yue, Wuhan (CN); Lu Huang, Wuhan (CN); Qiang Xiao, Wuhan (CN)

(73) Assignee: HUBEI BIO-PHARMACEUTICAL INDUSTRIAL TECHNOLOGICAL INSTITUTE, INC., Wuhan (CN)

(*) Notice: Subject to any disclaimer, the term of this patent is extended or adjusted under 35 U.S.C. 154(b) by 0 days.

(21) Appl. No.: 15/773,826

(22) PCT Filed: Nov. 4, 2016

(86) PCT No.: PCT/CN2016/104723
§ 371 (c)(1),
(2) Date: May 4, 2018

(87) PCT Pub. No.: WO2017/076355
PCT Pub. Date: May 11, 2017

(65) Prior Publication Data
US 2018/0338973 A1    Nov. 29, 2018

(30) Foreign Application Priority Data

Nov. 5, 2015   (CN) .......................... 2015 1 0744839
Jun. 8, 2016   (CN) .......................... 2016 1 0404608
Aug. 16, 2016  (CN) .......................... 2016 1 0675909

(51) Int. Cl.
| | | |
|---|---|---|
| C07D 401/12 | (2006.01) |
| C07D 401/14 | (2006.01) |
| A61K 31/506 | (2006.01) |
| A61K 31/5377 | (2006.01) |
| C07D 409/14 | (2006.01) |
| C07D 239/48 | (2006.01) |
| C07D 409/12 | (2006.01) |
| C07D 413/14 | (2006.01) |
| A61P 35/00 | (2006.01) |
| A61K 45/06 | (2006.01) |
| A61K 9/00 | (2006.01) |
| A61K 9/08 | (2006.01) |
| A61K 9/12 | (2006.01) |
| A61K 9/14 | (2006.01) |

(Continued)

(52) U.S. Cl.
CPC ........ *A61K 31/506* (2013.01); *A61K 31/5377* (2013.01); *A61K 45/06* (2013.01); *A61P 35/00* (2018.01); *C07D 239/48* (2013.01); *C07D 401/12* (2013.01); *C07D 401/14* (2013.01); *C07D 409/12* (2013.01); *C07D 409/14* (2013.01); *C07D 413/14* (2013.01); *A61K 9/0019* (2013.01); *A61K 9/08* (2013.01); *A61K 9/12* (2013.01); *A61K 9/14* (2013.01); *A61K 9/20* (2013.01); *A61K 9/48* (2013.01); *A61K 2300/00* (2013.01)

(58) Field of Classification Search
CPC .......................... C07D 401/12; C07D 401/14
See application file for complete search history.

(56) References Cited

U.S. PATENT DOCUMENTS

| | | | |
|---|---|---|---|
| 2011/0098280 A1* | 4/2011 | Garcia-Echeverria | ................ C04B 35/632 |
| | | | 514/217.06 |
| 2015/0140013 A1 | 5/2015 | Ramaswamy | |
| 2019/0256493 A1* | 8/2019 | Hong | ....... A61P 35/00 |

FOREIGN PATENT DOCUMENTS

| | | |
|---|---|---|
| CA | 2821102 A1 | 6/2012 |
| CA | 2824092 A1 | 8/2012 |
| CN | 101616895 A | 12/2009 |

(Continued)

OTHER PUBLICATIONS

Ex parte Firooznia, Appeal 2015-005810, U.S. Appl. No. 13/469,177, dated Sep. 5, 2017 (Year: 2017).*

(Continued)

*Primary Examiner* — Matthew P Coughlin
(74) *Attorney, Agent, or Firm* — Westman, Champlin & Koehler, P.A.; Z. Peter Sawicki; Amanda M. Prose

(57) ABSTRACT

The present invention provides a pyrimidine derivative and a use thereof. The pyrimidine derivative is the compound shown in formula I or a pharmaceutically acceptable salt, hydrate, solvate, metabolite or prodrug thereof, wherein, $R_1$, $R_2$, $R_3$, $R_4$ and $R_5$ are, for example, as defined in the specification. The compound can act as an ALK inhibitor, and is for preparing an anti-tumor medicament for suppressing an anaplastic lymphoma kinase.

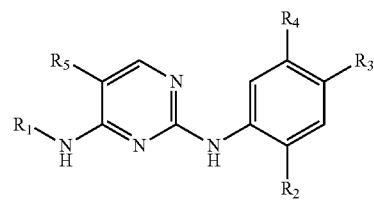

I

20 Claims, No Drawings

(51) Int. Cl.
*A61K 9/20* (2006.01)
*A61K 9/48* (2006.01)

(56) References Cited

FOREIGN PATENT DOCUMENTS

| CN | 104672214 A | 6/2015 | |
|---|---|---|---|
| CN | 104860922 A | 8/2015 | |
| CN | 104987324 A | 10/2015 | |
| CN | 106008503 A | 10/2016 | |
| JP | 2006520354 A | 9/2006 | |
| JP | 2007502260 A | 2/2007 | |
| JP | 2010512329 A | 4/2010 | |
| WO | WO-03026666 A1 * | 4/2003 | ........... C07D 231/12 |
| WO | 2004080980 A1 | 9/2004 | |
| WO | 2005016894 A1 | 2/2005 | |
| WO | 2015081813 A1 | 6/2015 | |
| WO | 2015130014 A1 | 9/2015 | |

OTHER PUBLICATIONS

Office Action issued for JP Application No. 2018-522969, dated Feb. 19, 2019; English Translation.
Office Action issued for AU Application No. 2016349089, dated Apr. 29, 2019.
Office Action issued for CA Application No. 3,004,372, dated Apr. 29, 2019.
Liu, Z. et al. "Novel 2,4-Diarylaminopyrimidine Analogues (DAAPalogues) Showing Potent c-Met/ALK Multikinase Inhibitory Activities" (2014) ACS Med Chem Lett; 5(4): 304-308.
Office Action issued for CN patent application 201610675909.6 dated Oct. 8, 2018.
Office Action issued for AU patent application 2016349089 dated Nov. 26, 2018.
International Search Report completed Jan. 24, 2017, and dated Feb. 9, 2017, for PCT Application No. PCT/CN2016/104723.
ISR for International Patent Application No. PCT/CN2016/104723, dated Feb. 9, 2017.
Written opinion for International Patent Application No. PCT/CN2016/104723, dated Feb. 9, 2017.
Galkin, A. V., et al. "Identification of NVP-TAE684, a potent, selective, and efficacious inhibitor of NPM-ALK" Proceedings of the National Academy of Sciences U S A., Jan. 2, 2007, 104 (1) 270-275.
Marsilje, T. H., et al. "Synthesis, Structure-Activity Relationships, and in Vivo Efficacy of the Novel Potent and Selective Anaplastic Lymphoma Kinase (ALK) Inhibitor 5-Choloro-N2-(2-isopropoxy-5-methyl-4-a(piperidin-4-yl)-N4-(2-(isopropylsulfonyl)phenyl)pyrimidine-2,4-diamine(LDK378)Currently in Phase 1and Phase 2 Clinical Trials" Journal of Medicinal Chemistry, Jun. 6, 2013, 56, 5675-5690.
Kang, C. H., et al. "Minor modifications to ceritinib enhance anti-tumor activity in EML4-ALK positive cancer" Cancer Letters, May 1, 2016, vol. 374, Issue 2, pp. 272-278.
Extended European Search Report issued for EP application No. 16861623.3, dated Sep. 20, 2019.

* cited by examiner

PYRIMIDINE DERIVATIVE AND USE THEREOF

CROSS-REFERENCE TO RELATED APPLICATIONS

The present application is the U.S. national phase of PCT Application No. PCT/CN2016/104723 filed on Nov. 4, 2016, which claims priorities to and benefits of Chinese Patent Application Nos. 201510744839.0 filed on Nov. 5, 2015, 201610404608.X filed on Jun. 8, 2016, and 201610675909.6 filed on Aug. 16, 2016 with the State Intellectual Property Office of P. R. China.

FIELD

The present disclosure relates to the biological medicine field, in particular to pyrimidine derivative and use thereof, and more particular to pyrimidine derivative, the method of preparing the same and use in preparation of a medicament.

BACKGROUND

Non-small-cell lung cancer (NSCLC) (synonym for non-small-cell carcinoma) including squamous carcinoma, adenocarcinoma and large cell carcinoma, is characterized by slower cell division than small cell carcinoma; as well as late spread and metastasis, representing about 80-85% of total lung cancer. Data shows that current morbidity of lung cancer in our country is rising 26.9% annually, with the number of patient newly-diagnosed with lung cancer increasing by 120,000 from 2000 to 2005, where the number of male patients increased from 260,000 to 330,000 and the number of female patients increased from 120,000 to 170,000. Furthermore, lung cancer has also becoming the first common one among all cancers in most regions in china. For example in Beijing, the morbidity of lung cancer increased by 56% from 2001 to 2010, during which one out of five patients newly-diagnosed with cancer is a patient affected with lung cancer. For another example in Zhejiang province, lung cancer still ranks at the top in "cancer spectrum" in 2011 issued by Zhejiang Cancer Hospital. For still another example in Guangzhou province, the morbidity of lung cancer is seven times more than that for 30 years ago.

With the progress of molecular medicine and the development of target drug, patients with advanced NSCLC have been treating with individualized therapy. At present in clinic application, the individualized therapy targeting NSCLC mainly aims at the epidermal growth factor receptor (EGFR) mutation and the Anaplastic lymphoma kinase (ALK) fusion gene, both of which have definite molecular targets, corresponding target assay technology and commercial target medicine, with clinical efficacy improved obviously.

Anaplastic lymphoma kinase (ALK) is a receptor tyrosine kinase, which is originally found in a subtype of anaplastic large cell lymphoma (ALCL) and thus is denominated as the Anaplastic Lymphoma kinase (Science, 1994, 263, 1281-1284; Oncogene, 1994, 9, 1567-1574). ALK fusion gene is a potent carcinogenic gene that is newly discovered as one of NSCLC-driven gene, with echinoderm microtubule related protein 4 (EML4-ALK) as the most common one. Abnormality in the ALK gene, such as translocation, point mutation and gene amplification, will result in abnormal kinases fused with other genes, which involve in carcinogenesis. The ALK fusion gene is generally found in non-smoking or less-smoking patients with lung adenocarcinoma. ALK-positive non-small cell lung cancer is a subtype of lung cancer newly discovered in 2007, representing 3% to 5% of total NSCLCs.

Although it has been studied a large number of compounds with inhibitory activity against protein kinases and some protein kinase inhibitors have been commercially available for NSCLC therapy, such as Crizotinib, there still remains many deficiencies, for example, drug resistance. The EML4-ALK fusion gene serving as a new target for cancer therapy has been validated with the first generation ALK inhibitor, Crizotinib (from Pfizer), which was approved by FDA rapidly in November 2011 as the first one of the first-line drug for ALK-positive NSCLC therapy based on exhibition of good efficacy in clinical trials with around 60% objective response rate and about 10 months of survival without cancer progression. However, the patient under such the therapy is found to become resistant after 9 to 12 months. Currently, it is considered that the secondary resistance is at least due to self-secondary mutation of the ALK kinase, including L1196M, G1269A, S1206Y, G1202R, 1151Tins, L11152R and C1156Y, with L1196M and G1269A detected at highest frequency in clinic. It has been revealed by researchers that the secondary mutation of ALK kinase is found in about one third of Crizotinib-resistant patients and no obvious progress is observed in about 40% ALK-positive patients under continuing therapy with Crizotinib. Moreover, it is also observed from two clinical trials for Crizotinib that the most common side effects are visual impairment, nausea, diarrhea, vomiting, edema and constipation, with an occurring rate above 25%.

As the Next-Generation ALK inhibitor developed by Novartis, LDK378 still exhibits 80% response rate in 88 patients with the ALK-positive NSCLCs, who had undergone the Crizotinib therapy, in the early clinical trial, and thus was awarded as "breakthrough" by FDA in March 2013 and approved as Ceritinib (trade name: Zykadia) by FDA in April 2014 to treat patients with ALK-positive NSCLCs who had been resistant to Crizotinib based on inhibition of Crizotinib-resistant mutation by LDK378. It is revealed by research that LDK378 inhibits the Crizotinib-resistant mutation, including L1196M, G1269A, 1171T and S1206Y, with G1202R and F1174C excluded, indicating certain limitation. Besides, the clinical dosage of the Ceritinib is large, about 750 mg, P.O qday.

Therefore, all the famous pharmaceutical companies have been focusing on development of a novel safer and more effective ALK inhibitor that would bring huge social values and economic interests. A novel ALK inhibitor having improved resistance and druggability can be developed by modifying structures of candidate compound, therefore improving bioactivity and bioavailability, which is of greatly importance for diseases caused by the ALK mutation in clinic. Thus, there is still a need to improve the ALK inhibitor.

SUMMARY

Embodiments of the present disclosure seek to solve at least one of the problems existing in the related art at least to some extent, or to provide a useful commercial alternative at least. For this purpose, the present disclosure provides in embodiments a pharmaceutical compound for treating a cancer.

In a first aspect, the present disclosure provides in embodiments compounds. In some embodiments, the compounds are a compound of formula I or a pharmaceutically acceptable salt, a hydrate, a solvate, a metabolite, or a prodrug thereof,

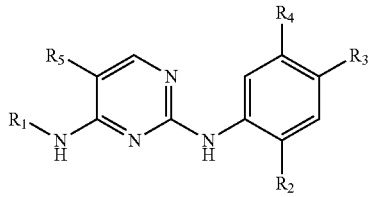

I in which,

R₁ is selected from 5- or 6-membered cycloalkyl, 5- or 6-membered heterocyclyl, 5- or 6-membered aryl, or 5- or 6-membered heteroaryl, optionally said 5- or 6-membered cycloalkyl, 5- or 6-membered heterocyclyl, 5- or 6-membered aryl and 5- or 6-membered heteroaryl each are independently substituted with one or more substituents chosen from halogen, hydroxyl, cyano, nitro, $C_{1-8}$ alkyl, $C_{2-8}$ alkenyl, $C_{2-8}$ alkynyl, $C_{3-8}$ cycloalkyl, 3- to 8-membered heterocyclyl, $C_{5-10}$ aryl, 5- to 10-membered heteroaryl, $C_{1-6}$ alkoxy, $C_{3-8}$ cycloalkoxy, —S(O)$_p$R$_6$, —C(O)R$_6$, —C(O)OR$_6$, —NR$_7$R$_8$ or —C(O)NR$_8$, with R$_6$, R$_7$ and R$_8$ each being independently hydrogen or $C_{1-4}$ alkyl, and p being 0, 1 or 2;

R₂ is selected from hydrogen, halogen, $C_{1-6}$ alkyl, $C_{1-6}$ alkoxy, halogen substituted $C_{1-6}$ alkyl, or halogen substituted $C_{1-6}$ alkoxy;

R₃ is selected from optionally substituted piperazinyl, optionally substituted morpholinyl, optionally substituted piperidyl, optionally substituted cyclohexylaminyl, optionally substituted $C_{1-2}$ alkyl or optionally substituted 1,2,3,6-tetrahydropyridyl, wherein a substitution on substituted $C_{1-2}$ alkyl is optionally substituted piperidyl;

R₄ is hydrogen or $C_{1-6}$ alkyl; and

R₅ is selected from hydrogen, chlorine, hydroxyl, cyano, $C_{1-6}$ alkyl, $C_{1-6}$ alkoxy, or halogen substituted $C_{1-6}$ alkoxy.

In embodiments of the present disclosure, R₁ is selected from 5- or 6-membered heterocyclyl, 5- or 6-membered aryl, or 5- or 6-membered heteroaryl substituted with one or more —S(O)$_p$R$_6$.

In embodiments of the present disclosure, R₂ is selected from hydrogen, halogen, $C_{1-6}$ alkyl, $C_{1-6}$ alkoxy, or halogen substituted $C_{1-6}$ alkoxy.

In embodiments of the present disclosure, R₃ is selected from optionally substituted piperazinyl, optionally substituted morpholinyl, optionally substituted piperidyl, optionally substituted methyl or optionally substituted 1,2,3,6-tetrahydropyridyl, with a substitution on the optionally substituted methyl being optionally substituted piperidyl, wherein said optionally substituted piperazinyl, optionally substituted morpholinyl, optionally substituted piperidyl, or optionally substituted 1,2,3,6-tetrahydropyridyl is optionally substituted with one or more substituents chosen from $C_{1-6}$ alkyl, hydroxyl, $C_{1-6}$ alkylamino, $C_{1-6}$ alkoxy, oxo (=O), $C_{1-6}$ acyl, morpholinyl, $C_{1-6}$ alkylmorpholinyl, piperazinyl, $C_{1-6}$ alkylpiperazinyl, $C_{1-6}$ acylpiperazinyl, hydroxyl $C_{1-6}$ alkylpiperazinyl, piperidyl or $C_{1-6}$ alkylaminopiperidyl.

In embodiments of the present disclosure, R₄ is hydrogen or $C_{1-4}$ alkyl.

In embodiments of the present disclosure, R₅ is chlorine or halogen substituted $C_{1-6}$ alkoxy.

In embodiments of the present disclosure, R₆ is $C_{1-4}$ alkyl.

In embodiments of the present disclosure, p is 2.

In embodiments of the present disclosure, R₁ is any one of

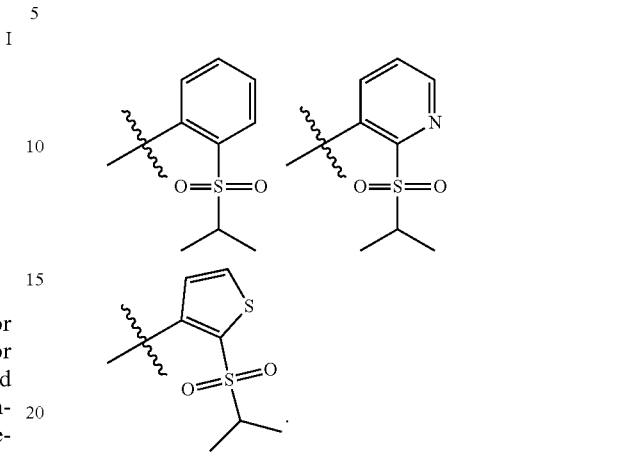

In embodiments of the present disclosure, R₂ is selected from hydrogen, chlorine, methyl, methoxy, ethoxy, isopropoxy or difluoromethoxy.

In embodiments of the present disclosure, R₃ is any one selected from

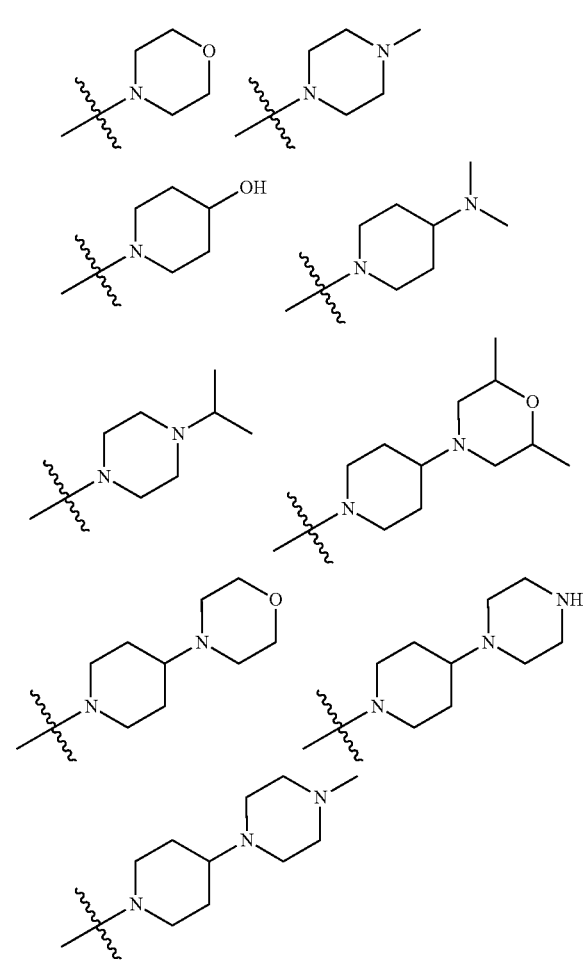

-continued
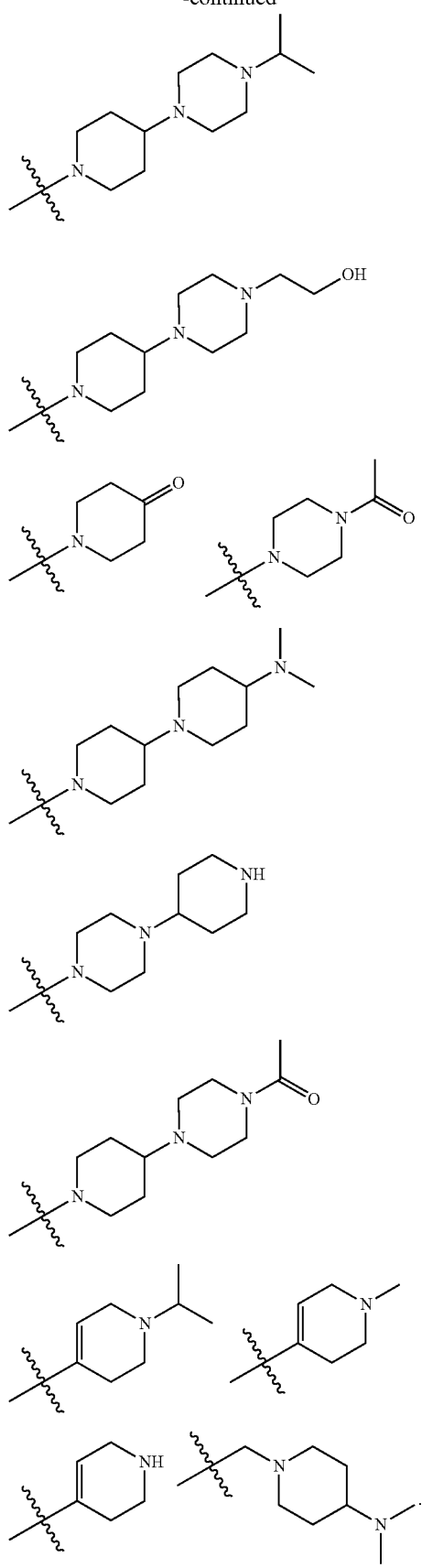
In embodiments of the present disclosure, $R_1$ is
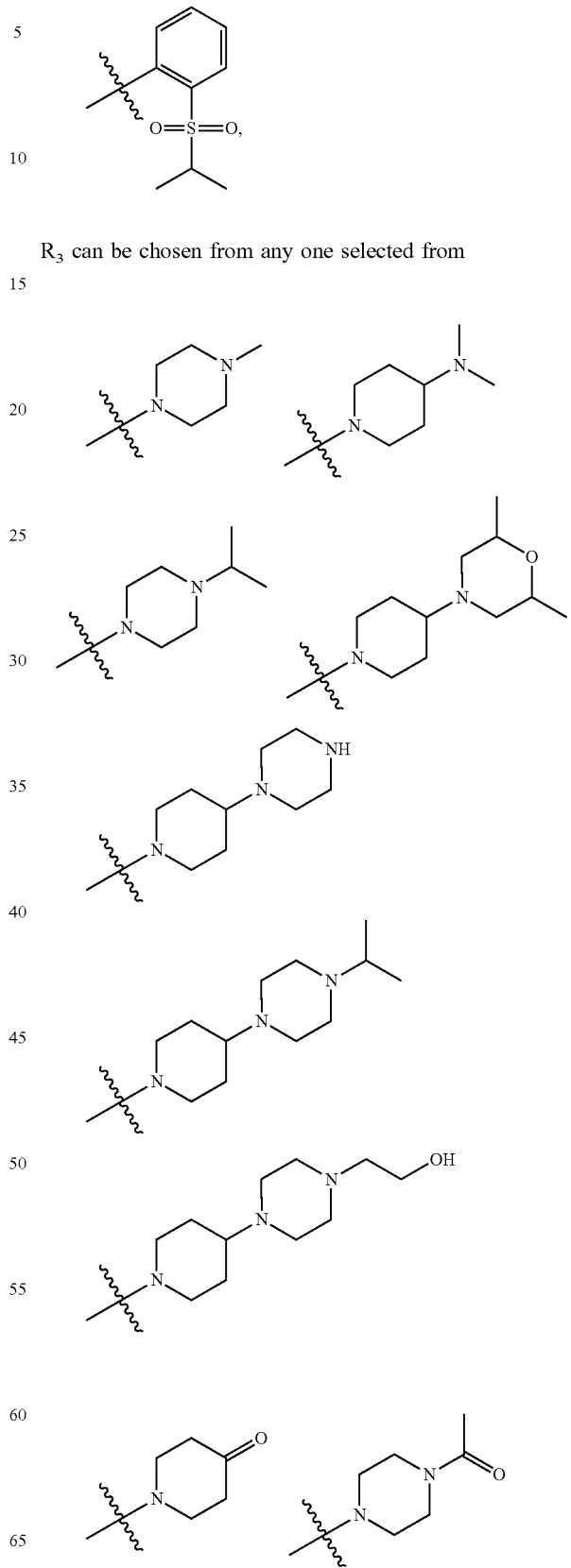
$R_3$ can be chosen from any one selected from

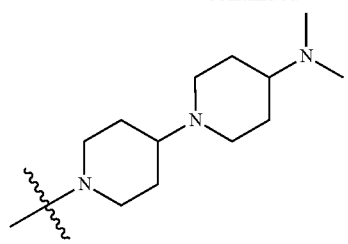

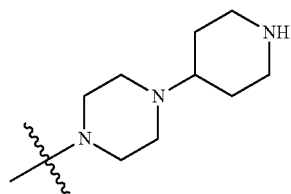

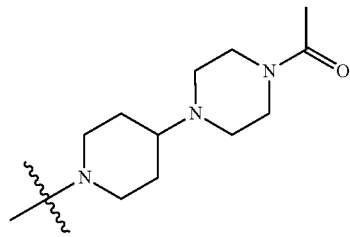

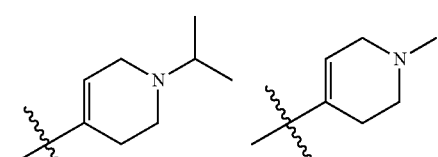

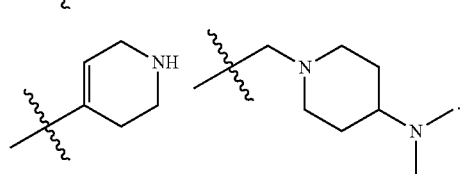

In embodiments of the present disclosure, $R_4$ is hydrogen or methyl.

In embodiments of the present disclosure, $R_5$ is chlorine or difluoromethoxy.

It will be understood by those skilled in the art that

in the chemical structures herein is used to refer to a chemical bond by which a part or a substituent thereof is bound to a core structure or a backbone structure.

Throughout the specification herein, selection thus can be made to $R_1$ to $R_5$ and their substituents, as well as p within the compounds of formula I by those skilled in the art to provide the stable compounds represented in formula I in the examples and their pharmaceutically acceptable salts, hydrates, solvates, metabolites, or prodrugs.

In embodiments of the present disclosure, the compound of formula I is any one selected from

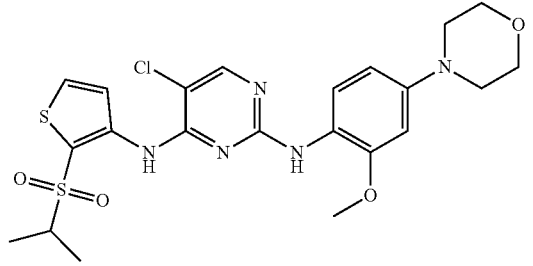

I-1

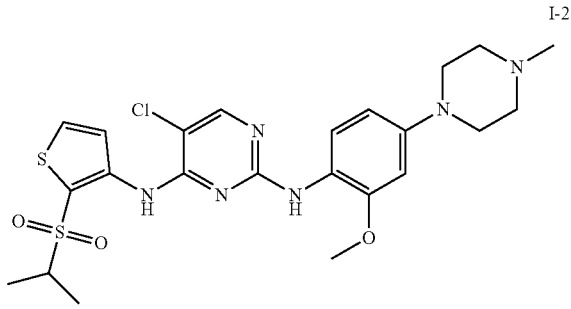

I-2

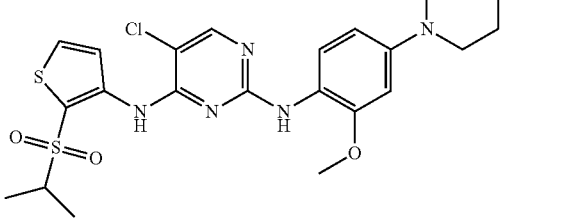

I-3

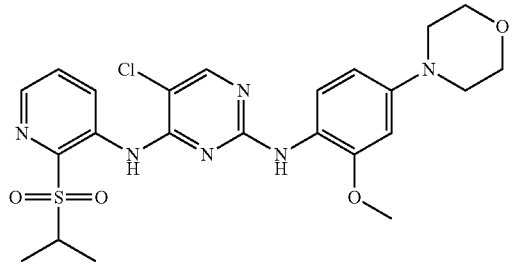

I-4

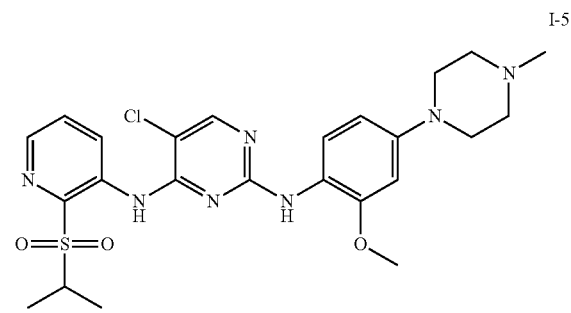

I-5

-continued
I-6
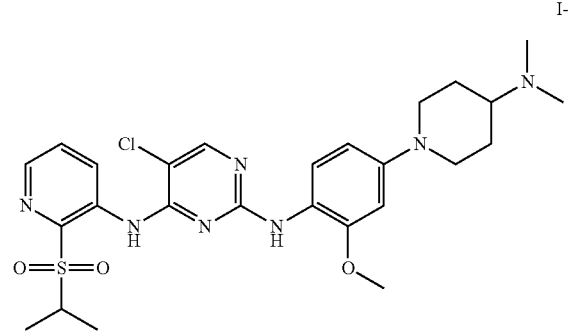
I-7
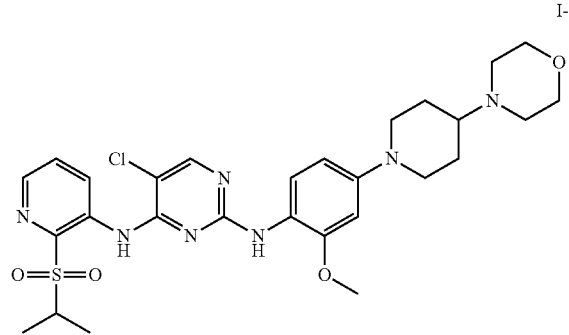
I-8
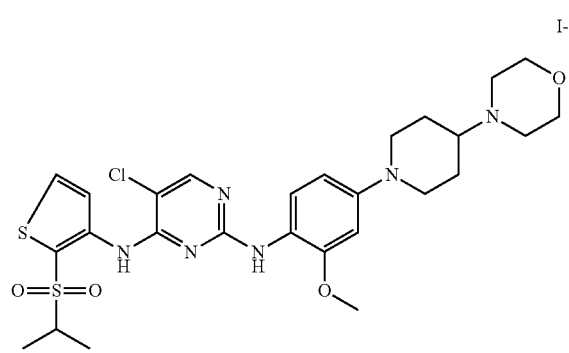
I-9
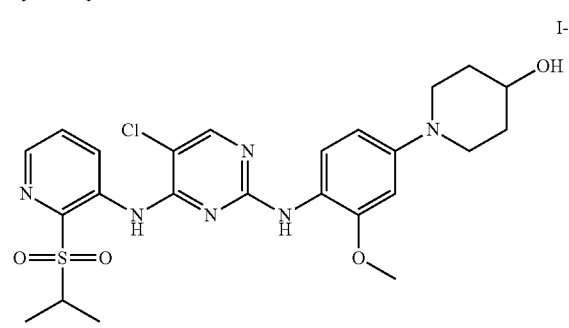
I-10
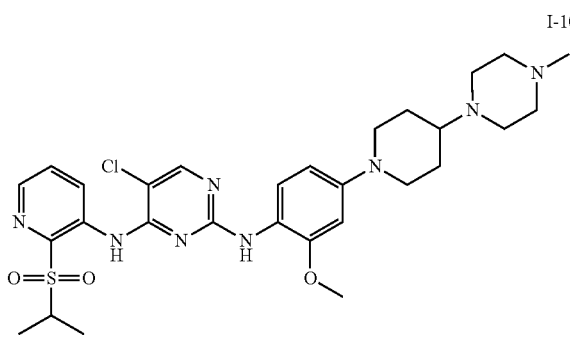
-continued
I-11
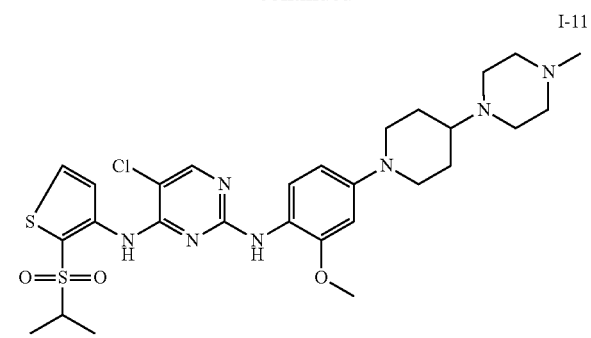
I-12
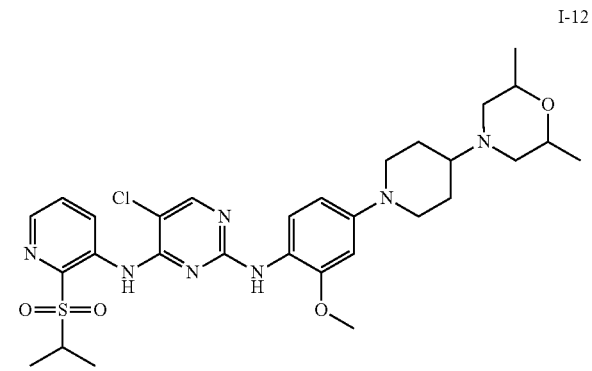
I-13
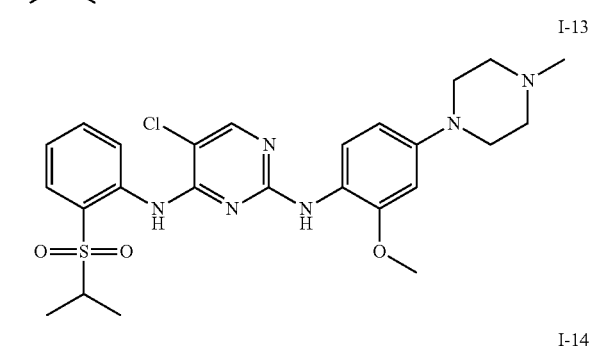
I-14
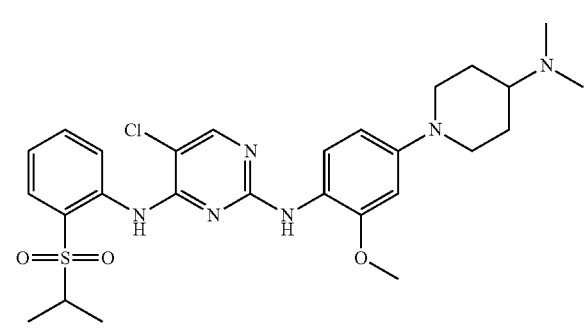
I-15
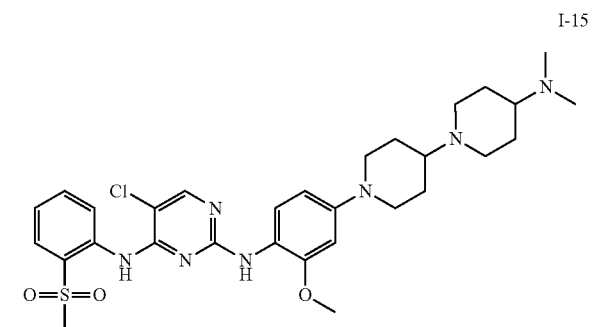

-continued
I-16
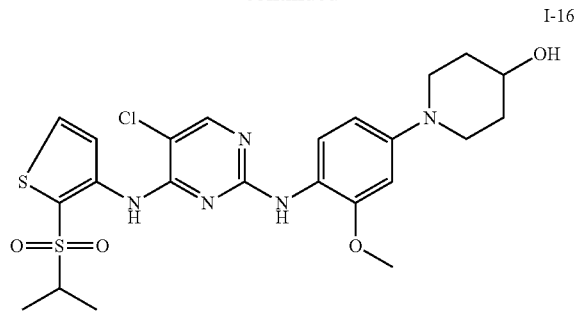
I-17
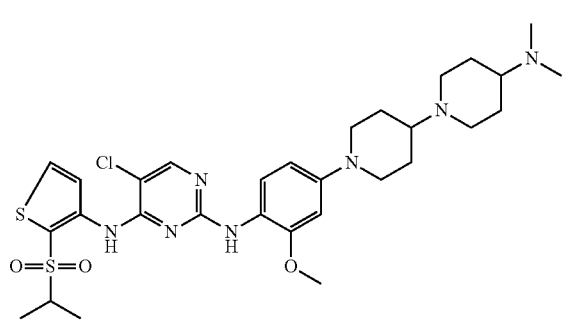
I-18
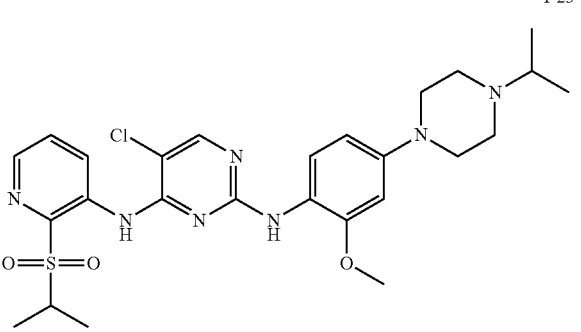
I-23
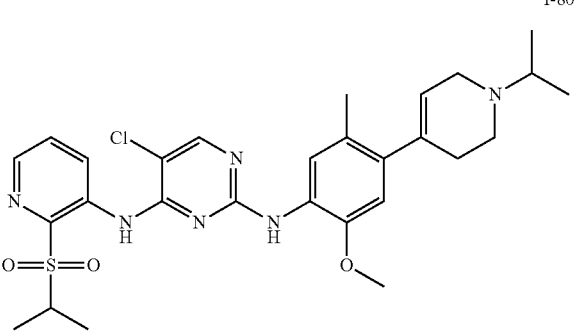
-continued
I-82
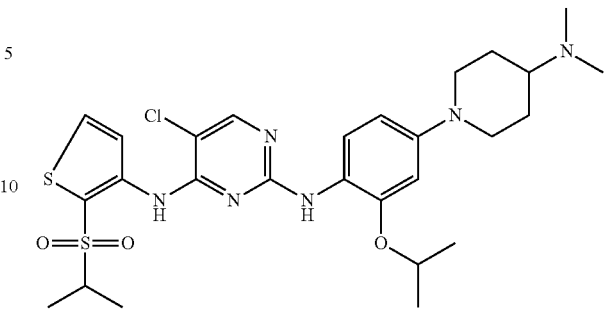
I-84
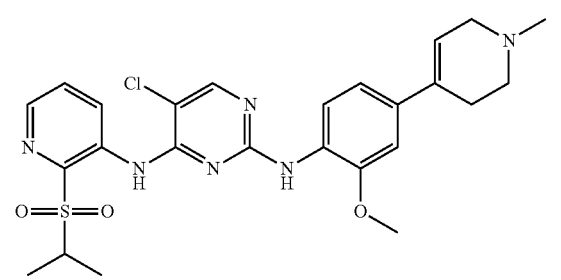
I-85
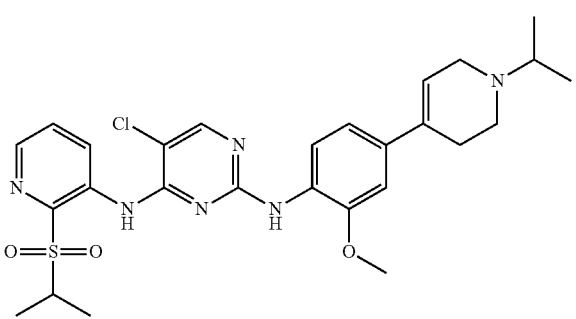
I-86
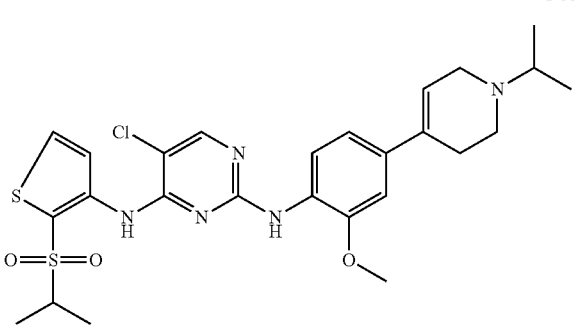
I-80
I-88
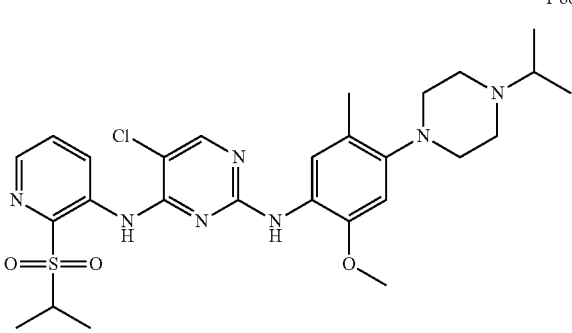

-continued
I-89
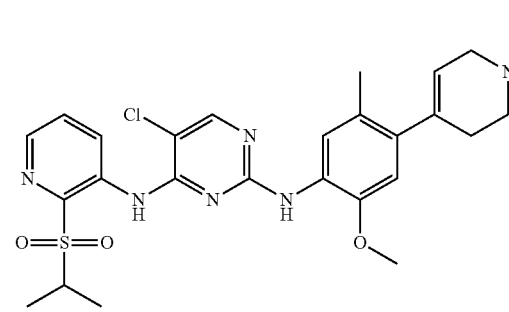
I-98
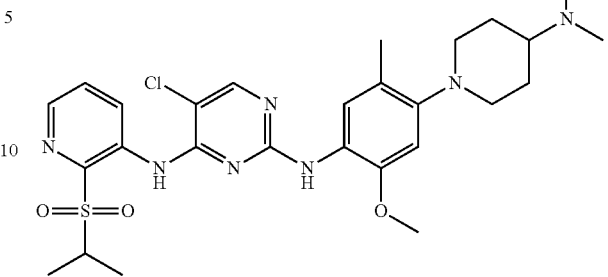
I-90
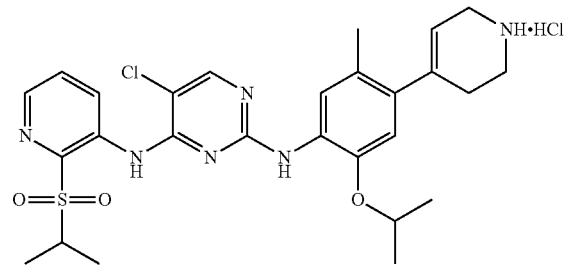
I-100
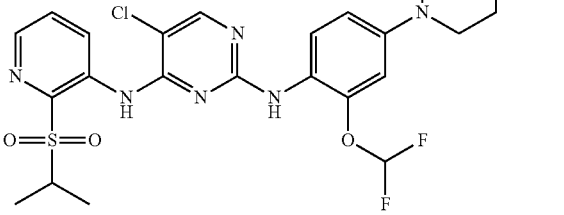
I-91
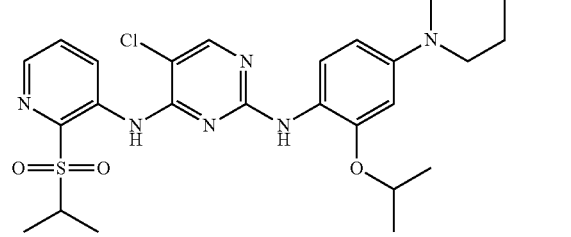
I-102
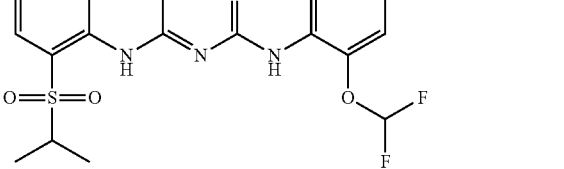
I-92
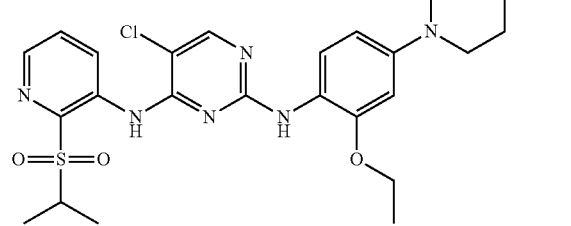
I-103
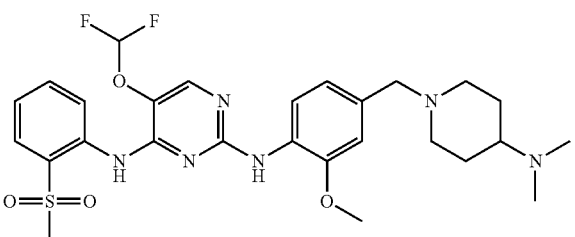
I-95
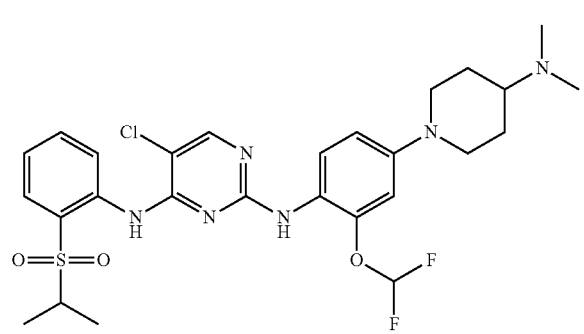
I-107
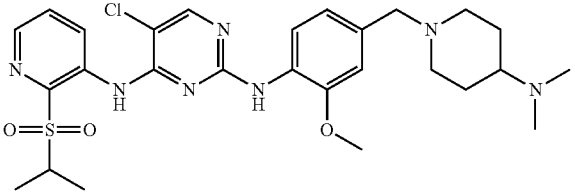

-continued

I-109
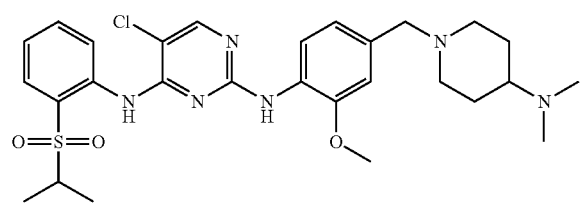

I-110
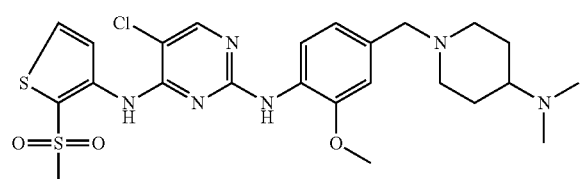

I-111
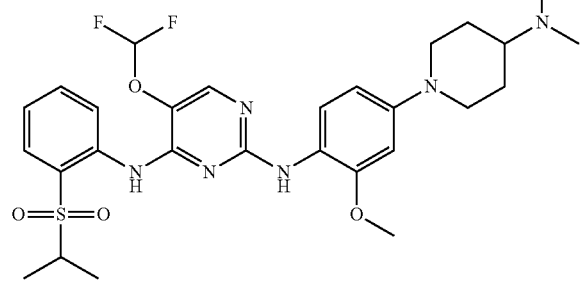

I-112
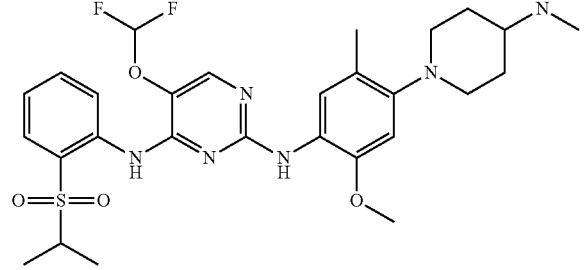

I-113
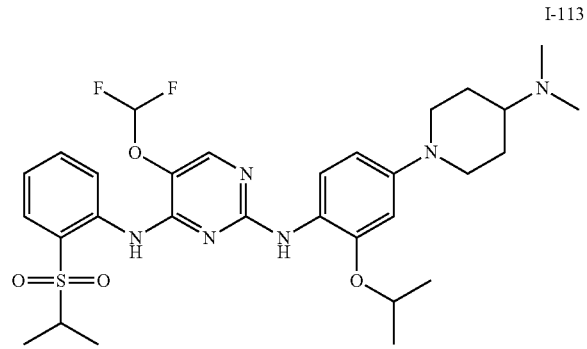

-continued

I-114
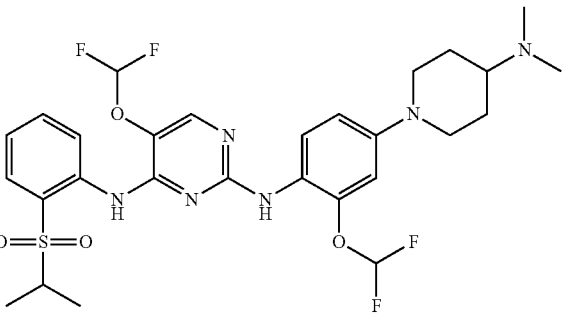

I-115
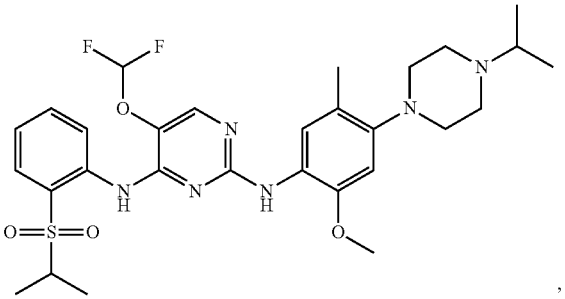

or a pharmaceutically acceptable salt, a hydrate, a solvate, a metabolite, or a prodrug thereof.

As used herein, $C_{1-6}$ is chosen from $C_1$, $C_2$, $C_3$, $C_4$, $C_5$ and $C_6$; $C_{1-8}$ is chosen from $C_1$, $C_2$, $C_3$, $C_4$, $C_5$, $C_6$, $C_7$ and $C_8$; $C_{2-8}$ is chosen from $C_2$, $C_3$, $C_4$, $C_5$, $C_6$, $C_7$ and $C_8$; $C_{3-8}$ is chosen from $C_3$, $C_4$, $C_5$, $C_6$, $C_7$ and $C_8$; $C_{5-10}$ is chosen from $C_5$, $C_6$, $C_7$, $C_8$, $C_9$ and $C_{10}$. As used herein, the term "pharmaceutically acceptable" is intended to mean the compounds, materials, compositions and/or dosage forms of the present disclosure are suitable for use in contact with human and animal tissues within a range of reliable medical judgment, without excessive toxicity, irritation, allergic reaction or other problems or complications, thus having a reasonable benefit comparable to their risks.

The term "pharmaceutically acceptable salts" refer to salts of the compound of the present disclosure prepared by contacting the compound containing one or more designated substituents with a relatively non-toxic acid or base. For example, when the compound contains relatively acidic functional groups, its base addition salt can be obtained by contacting a neutral form of such compound with an adequate amount of base in a pure solution or a suitable inert solvent. Examples of this pharmaceutically acceptable base addition salt include sodium, potassium, calcium, ammonium, organic amino or magnesium salts or other similar salts. Also, when the compound contains relatively basic functional groups, its acid addition salt can be obtained by contacting a neutral form of such compound with an adequate amount of acid in a pure solution or a suitable inert solvent. Examples of this pharmaceutically acceptable acid addition salt include inorganic acid salts, including, such as hydrochloric acid, hydrobromic acid, nitric acid, carbonic acid, bicarbonate, phosphoric acid, monohydrogen phosphate, dihydrogen phosphate, sulfuric acid, hydrogen sulphate, hydroiodic acid, phosphorous acid and the like; organic acid salts, including, such as acetic acid, propionic acid, isobutyric acid, maleic acid, malonic acid, benzoic acid, succinic acid, suberic acid, fumaric acid, lactic acid, mandelic acid, phthalic acid, benzenesulfonic acid, p-toluenesulfonic acid, citric acid, tartaric acid, methanesulfonic acid and the like; and salts of organic acid, such as salts of amino acid (such as, arginine), glucuronic acid and the like (see, Berge et al., "Pharmaceutical Salts", Journal of Pharmaceutical Science 66: 1-19 (1977)). In certain embodiments of the present disclosure, the compound contains both basic and acidic functional groups, so as to allowing converted to either base or acid addition salt.

For example, the neutral form of the compound can be regenerated by contacting the salt thereof with a base or acid and then isolating the resulting parent compound which differs with other forms of its salt in some physical properties, such as solubility in polar solvents, using conventional manners.

As used herein, "pharmaceutically acceptable salts" are derivatives of the compound in the present disclosure which was formed by contacting the parent compound with an acid or base. Examples of the pharmaceutically acceptable salt include, but are not limited to, inorganic acid or organic acid salts of basic groups (such as amine group), alkali metal or organic salts of acidic groups (such as carboxylic acid) and the like. The pharmaceutically acceptable salts typically are non-toxic, such as the quaternary ammonium salt of the parent compound or salts formed with non-toxic inorganic or organic acids. The non-toxic salts usually include, but are not limited to those derived from inorganic and organic acids which are selected from the group consisting of 2-acetoxybenzoic acid, 2-hydroxyethanesulfonic acid, acetic acid, ascorbic acid, benzenesulfonic acid, benzoic acid, bicarbonate, carbonic acid, citric acid, edetic acid, ethanedisulfonic acid, ethanesulfonic acid, fumaric acid, glucoheptose, gluconic acid, glutamic acid, glycolic acid, hydrobromic acid, hydrochloric acid, hydroiodide, hydroxyl, hydroxynaphthalene, isethionic acid, lactic acid, lactose, dodecylsulfonic acid, maleic acid, malic acid, mandelic acid, methanesulfonic acid, nitric acid, oxalic acid, pamoic acid, pantothenic acid, phenylacetic acid, phosphoric acid, polygalactaldehyde, propionic acid, salicylic acid, stearic acid, Folinate, succinic acid, sulfamic acid, p-aminobenzenesulfonic acid, sulfuric acid, tannicacid, tartaric acid and p-toluenesulfonic acid.

The pharmaceutically acceptable salts of the present disclosure can be synthesized from the parent compounds containing acidic or basic groups using conventional chemical methods, and typically be prepared by contacting the compound in a free acidic or basic form with a stoichiometric amount of suitable base or acid in water or organic solvents or both, for example, non-aqueous medium such as ether, ethyl acetate, ethanol, isopropanol or acetonitrile.

In addition to the pharmaceutically acceptable salt thereof, the compound of the present disclosure can also be existed as a prodrug thereof, which is easily to be converted into the present compound by chemical reaction under physiological conditions. Any compounds that can be converted in vivo into the present compounds of formula I to provide bioactivity are within the scope of the present disclosure. For example, a carboxyl-containing compound forms physically-hydrolysable ester, serving as the prodrug which can be hydrolyzed in vivo under physiological conditions to give the present compound of formula I. For example, said prodrug is administered orally, because it is mainly hydrolyzed by digestive enzymes. The prodrug in form of ester can also be administered parenterally, if it is active or is hydrolyzed in blood. In addition, the prodrug can be converted to the compound of the present disclosure in vivo by chemical or biochemical methods.

The compound of the present disclosure can be existed as a non-solvent or solvate (including hydrate) thereof, generally speaking both of them being comparatively included in the present disclosure. The compound of the present disclosure can also be existed in polycrystalline or amorphous forms.

The compound of the present disclosure can contain asymmetric carbon atoms (that is optical center) or double bonds, and all of the racemate, the diastereomer, the geometrical isomer and the individual isomer thereof are included within the scope of the present disclosure.

The graphic representations of racemic, ambiscalemic and scalemic or enantiomerically pure compounds used herein are taken from Maehr, J. Chem. Ed. 1985, 62: 114-120. The absolute configuration of a stereogenic center is specified by a wedge bond or a dashed bond, unless otherwise specified. When containing olefinic double bonds or other geometric asymmetric centers, the compound described herein includes E, Z geometric isomers, unless otherwise specified; and all the tautomers thereof are also included within the scope of the present disclosure.

The compound of the present disclosure can contain one or more designated geometrical isomers or stereoisomers, and all of them are contemplated by the applicant, including cis-isomers, trans-isomers, (−)-enantiomers, (+)-enantiomers, (R)-enantiomers. (S)-enantiomers, diastereoisomers, (D)-isomers and (L)-isomers, and racemic mixture thereof or other mixture, such as enantiomer or diastereomer enriched mixture, all of the mixtures being within the scope of the present disclosure. Other asymmetric carbon atoms can also be existed in the substituents such as alkyl and the like, and all of the isomers and mixtures thereof are also included within the scope of the present disclosure.

Optically active (R)- and/or (S)-isomers may be prepared by using chiral synthons or chiral reagents, or using other conventional techniques, so that a desired enantiomer of the compound in the present disclosure can be prepared by asymmetric synthesis or derivatization with chiral auxiliaries, and specifically including the steps of isolating the resulting enantiomer from the diastereomeric mixture, and then cleaving the auxiliary groups in the enantiomer to provide the desired pure enantiomer. Alternatively, when the compound contains basic functional groups (e.g., amino group) or acidic functional groups (e.g., carboxyl group), an enantiomer of the compound can be prepared by contacting the compound with an appropriate amount of optically active acids or bases to form a diastereomeric salt, and resolving the diastereoisomer mixture by methods well known in the art such as fractional crystallization or chromatography to separate the enantiomer with the diastereoisomer followed by collection of the separated pure enantiomer. Generally, the separation of an enantiomer with a diastereoisomer is usually accomplished by chromatography on chiral stationary phase, and optionally in combination with chemical derivatization method (e.g., carbamate was generated by amine).

In the present disclosure, one or more atoms constituting the present compound may process non-natural proportions of atomic isotopes, and for example, the compound can be labeled with radioisotopes, such as tritium ($^3H$), iodine-125 ($^{125}I$) or C-14 ($^{14}C$). All the combinations of isotopes in the compound are included within the scope of the present disclosure, no matter the isotopes are radioactive or not.

The term "excipient" generally refers to the carrier, diluent and/or medium required to formulate an effective pharmaceutical composition.

For any drugs or pharmacologically active agents, the term "effective amount" or "therapeutically effective amount" refers to a sufficient amount of a drug or agent that is non-toxic but be capable of achieving the desired effect. For the orally administered formulation described herein, the "effective amount" of an active substance in the formulation, refers to its amount required to achieve the desired effect when used in association with one or more other active substances. The effective amount varies from person to person, depending on the age and general condition of the receptor and on the designated active substance. The appropriate effective amount in individual cases can be determined by a person skilled in the art in accordance with routine testing.

The terms "active ingredient", "therapeutic agent", "active substance" or "active agent" refer to a chemical entity which is effective in treating targeted disorders, diseases or conditions.

The term "substituted" means that at least one hydrogen on the designated atom is replaced with one or more substituents including variants of deuterium and hydrogen, provided that the designated atom's normal valence is not exceeded and the substituted stucture is stable. When the substituent is ketone group (i.e., =O), then two hydrogens on the atom are replaced, but hydrogens on aromatic group cannot be replaced by ketone group. The term "optionally substituted" means that the hydrogens on the designated atom may be substituted or not substituted with one or more substituents unless otherwise specified. The type and number of the substituents are not specifically restricted at the substitution occurrence.

When any variable (e.g., R) occurs more than one time in any constituent or structure of the present compound, at each occurrence, its definition is independent. For example, if a group is substituted with 0 to 2 of R, the group may be optionally substituted with up to two of R, and R can be different groups at each occurrence. In addition, combinations of substituents and/or variables are permissible provided that the compound produced is stable. When one of the variables is a single bond, it indicated that the two groups to which it is attached are directly connected. For example, when L represents a single bond in A-L-Z, it means that A-L-Z is actually A-Z.

In the context of the present disclosure, the terms "alkyl", "alkane" or "alkyl group" are exchangeable, with the alkyl optionally substituted with one or more substituents described herein. In some embodiments of the present disclosure, the alkyl group contains 1 to 8 carbon atoms. In other embodiments, the alkyl group contains 1 to 6 carbon atoms. In still other embodiments, the alkyl group contains 1 to 4 carbon atoms. Examples of the alkyl group contain but not limited to methyl (Me, —CH$_3$), ethyl (Et, —CH$_2$CH$_3$), n-propyl (n-Pr, —CH$_2$CH$_3$CH$_3$), isopropyl (i-Pr, —CH(CH$_3$)$_2$), n-butyl (n-Bu, —CH$_2$CH$_2$CH$_2$CH$_3$), isobutyl (i-Bu, —CH$_2$CH(CH$_3$)$_2$), sec-butyl (s-Bu, —CH(CH$_3$)CH$_2$CH$_3$), tert-butyl (t-Bu, —C(CH$_3$)$_3$), n-pentyl (—CH$_2$CH$_2$CH$_2$CH$_2$CH$_3$), 2-pentyl (—CH(CH$_3$)CH$_2$CH$_2$CH$_3$), 3-pentyl (—CH(CH$_2$CH$_3$)$_2$), 2-methyl-2-butyl (—C(CH$_3$)$_2$CH$_2$CH$_3$), 3-methyl-2-butyl (—CH(CH$_3$)CH(CH$_3$)$_2$), 3-methyl-1-butyl (—CH$_2$CH$_2$CH(CH$_3$)$_2$), 2-methyl-1-butyl (—CH$_2$CH(CH$_3$)CH$_2$CH$_3$), n-hexyl (—CH$_2$CH$_2$CH$_2$CH$_2$CH$_2$CH$_3$), 2-hexyl (—CH(CH$_3$)CH$_2$CH$_2$CH$_2$CH$_3$), 3-hexyl (—CH(CH$_2$CH$_3$)(CH$_2$CH$_2$CH$_3$)), 2-methyl-2-pentyl (—C(CH$_3$)$_2$CH$_2$CH$_2$CH$_3$), 3-methyl-2-pentyl (—CH(CH$_3$)CH(CH$_3$)CH$_2$CH$_3$), 4-methyl-2-pentyl (—CH(CH$_3$)CH$_2$CH(CH$_3$)$_2$), 3-methyl-3-pentyl (—C(CH$_3$)(CH$_2$CH$_3$)$_2$), 2-methyl-3-pentyl (—CH(CH$_2$CH$_3$)CH(CH$_3$)$_2$), 2,3-dimethyl-2-butyl (—C(CH$_3$)$_2$CH(CH$_3$)$_2$), 3,3-dimethyl-2-butyl (—CH(CH$_3$)C(CH$_3$)$_3$), n-heptyl, n-octyl and so on.

The term "alkoxy" refers to an alkyl group, as previously defined, attached to the rest moiety of molecule via an oxygen atom. Unless otherwise specified, the alkoxy group contains 1 to 6 carbon atoms. Examples of the alkoxy group include but not limited to methoxy (MeO, —OCH$_3$), ethyoxy (EtO, —OCH$_2$CH$_3$), propoxy (n-PrO, n-propoxy, —OCH$_2$CH$_2$CH$_3$), isopropoxy (i-PrO, i-propoxy, —OCH(CH$_3$)$_2$), n-butoxy (n-BuO, n-butoxy, —OCH$_2$CH$_2$CH$_2$CH$_3$), 1-methylpropoxy (s-BuO, s-butoxy, —OCH(CH$_3$)CH$_2$CH$_3$), 2-methyl-1-propoxy (i-BuO, i-butoxy, —OCH$_2$CH(CH$_3$)$_2$), tert-butoxy (t-BuO, t-butoxy, —OC(CH$_3$)$_3$), n-pentyloxy (n-pentyloxy, —OCH$_2$CH$_2$CH$_2$CH$_2$CH$_3$), 2-pentyloxy (—OCH(CH$_3$)CH$_2$CH$_2$CH$_3$), 3-pentyloxy (—OCH(CH$_2$CH$_3$)$_2$), 2-methyl-2-butoxy (—OC(CH$_3$)$_2$CH$_2$CH$_3$), 3-methyl-2-butoxy (—OCH(CH$_3$)CH(CH$_3$)$_2$), 3-methyl-1-butoxy (—OCH$_2$CH$_2$CH(CH$_3$)$_2$), 2-methyl-1-butoxy (—OCH$_2$CH(CH$_3$)CH$_2$CH$_3$), n-hexyloxy (n-hexyloxy. —OCH$_2$CH$_2$CH$_2$CH$_2$CH$_2$CH$_3$) and so on.

The term "cycloalkyl" refers to monovalent or multivalent saturated monocyclic, bicyclic, or tricyclic systems containing 3 to 8 carbon atoms. The cycloalkyl group can be optionally substituted with one or more substituents described herein. In some embodiments, the cycloalkyl contains 3 to 8 carbon atoms. Examples of the cycloalkyl group include but not limited to cyclopropyl, cyclobutyl, cyclopentyl, cyclohexyl, cycloheptyl, cyclooctyl and so on.

The term "halogen" refers to fluorine (F), chlorine (Cl), bromine (Br) or iodine (I).

The term "alkylamino" includes "N-alkylamino" and "N,N-dialkylamino", in which the amino group each is independently substituted with one or two alkyl groups, as previously defined. An appropriate alkylamino group can be monoalkylamino or dialkylamino. Examples of the alkylamino include but not limited to N-methylamino, N-ethylamino, isopropylamino, propylamino, tert-butylamino, n-butylamino, I-methylpropylamino, n-pentylamino, n-hexylamino, N,N-dimethylamino, N,N-diethylamino and so on.

The term "C$_{1-6}$ acyl" refers to R—C(=O)—, in which R is C$_{1-6}$ alkyl, as previously defined.

The term "alkylmorpholinyl" refers to morpholinyl substituted with one or more alkyl groups.

The term "C$_{1-6}$ acylpiperazinyl" refers to piperazinyl substituted with one or more C$_{1-6}$ acyl groups.

The term "hydroxyl C$_{1-6}$ alkylpiperazinyl" refers to C$_{1-6}$ alkyl substituted piperazinyl which is substituted with one or more hydroxyl groups.

The term "alkylaminopiperidyl" refers to amino substituted piperidyl which is substituted with one or more alkyl groups.

The words "comprise", "comprising", "include", "including" and the like are to be construed in an inclusive sense, i.e., all contents specified in the present disclosure are included, but contents in other aspects are not intended to be excluded.

All reaction solvent used in each reaction step of the present disclosure is not particularly limited, and any solvent that can dissolve a starting material to some extent and does not inhibit the reaction is included. In addition, similar modifications, alternatives, or equivalents of the solvents, solvent combinations, and proportions thereof described herein also belong to the scope of the present disclosure.

In a second aspect, the present disclosure provides in embodiments a method of preparing a compound represented in formula I. A general method of synthesizing such compounds includes synthesizing a parent pyrimidine compound and then connecting to a nitrogen-containing compound via a carbon chain.

In some embodiments of the present disclosure, the present disclosure provides a method of preparing a compound represented in formula I. Said method includes the following steps: substitution reaction between the compound of formula 5A and the compound of formula 4A; and then conversion to a corresponding compound of formula I in accordance with different substitutions or a protective group used, thus giving the compound of formula I,

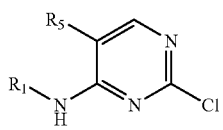

formula 5A

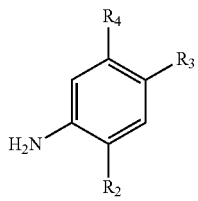

formula 4A in which, $R_1$ is selected from 5- or 6-membered cycloalkyl, 5- or 6-membered heterocyclyl, 5- or 6-membered aryl, or 5- or 6-membered heteroaryl, and optionally said 5- or 6-membered cycloalkyl, 5- or 6-membered heterocyclyl, 5- or 6-membered aryl and 5- or 6-membered heteroaryl each are independently substituted with one or more substituents chosen from halogen, hydroxyl, cyano, nitro, $C_{1-8}$ alkyl, $C_{2-8}$ alkenyl, $C_{2-8}$ alkynyl, $C_{3-8}$ cycloalkyl, 3- to 8-membered heterocyclyl, $C_{5-10}$ aryl, 5- to 10-membered heteroaryl, $C_{1-6}$ alkoxy, $C_{3-8}$ cycloalkoxy, —S(O)$_p$R$_6$, —C(O)R$_6$, —C(O)OR$_6$, —NR$_7$R$_8$ or —C(O)NR$_8$, with R$_6$, R$_7$ and R$_8$ each being independently hydrogen or C$_4$ alkyl, and p being 0, 1 or 2;

$R_2$ is selected from hydrogen, halogen, $C_{1-6}$ alkyl, $C_{1-6}$ alkoxy, halogen substituted $C_{1-6}$ alkyl, or halogen substituted $C_{1-6}$ alkoxy;

$R_3$ is selected from optionally substituted piperazinyl, optionally substituted morpholinyl, optionally substituted piperidyl, optionally substituted cyclohexylaminyl, optionally substituted $C_{1-2}$ alkyl, or optionally substituted 1,2,3,6-tetrahydropyridyl, with a substitution on substituted $C_{1-2}$ alkyl being optionally substituted piperidyl;

$R_4$ is hydrogen or $C_{1-6}$ alkyl; and $R_5$ is selected from hydrogen, chlorine, hydroxyl, cyano, $C_{1-6}$ alkyl, $C_{1-6}$ alkoxy, or halogen substituted $C_{1-6}$ alkoxy.

In some embodiments of the present disclosure, $R_1$ is selected from 5- or 6-membered heterocyclyl, 5- or 6-membered aryl or 5- or 6-membered heteroaryl substituted with one or more —S(O)$_p$R$_6$.

In some embodiments of the present disclosure, $R_2$ is selected from hydrogen, halogen, $C_{1-6}$ alkyl, $C_{1-6}$ alkoxy, or halogen substituted $C_{1-6}$ alkoxy.

In some embodiments of the present disclosure, $R_3$ is selected from optionally substituted piperazinyl, optionally substituted morpholinyl, optionally substituted piperidyl, optionally substituted methyl or optionally substituted 1,2,3,6-tetrahydropyridyl, with a substitution on the optionally substituted methyl being optionally substituted piperidyl, in which said optionally substituted piperazinyl, optionally substituted morpholinyl, optionally substituted piperidyl, or optionally substituted 1,2,3,6-tetrahydropyridyl is optionally substituted with one or more substituents chosen from $C_{1-6}$ alkyl, hydroxyl, $C_{1-6}$ alkylamino, $C_{1-6}$ alkoxy, oxo (=O), $C_{1-6}$ acyl, morpholinyl, $C_{1-6}$ alkylmorpholinyl, piperazinyl, $C_{1-6}$ alkylpiperazinyl, $C_{1-6}$ acylpiperazinyl, hydroxyl $C_{1-6}$ alkylpiperazinyl, piperidyl or $C_{1-6}$ alkylaminopiperidyl.

In some embodiments of the present disclosure, $R_4$ is hydrogen or $C_{1-6}$ alkyl.

In some embodiments of the present disclosure, $R_5$ is chlorine or halogen substituted $C_{1-6}$ alkoxy.

In some embodiments of the present disclosure, $R_6$ is $C_{1-4}$ alkyl.

In some embodiments of the present disclosure, p is 2.

In some embodiments of the present disclosure, $R_1$ is any one of

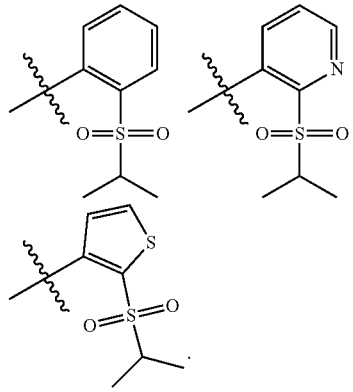

In some embodiments of the present disclosure, $R_2$ is selected from hydrogen, chlorine, methyl, methoxy, ethoxy, isopropoxy or difluoromethoxy.

In some embodiments of the present disclosure, $R_3$ is any one selected from

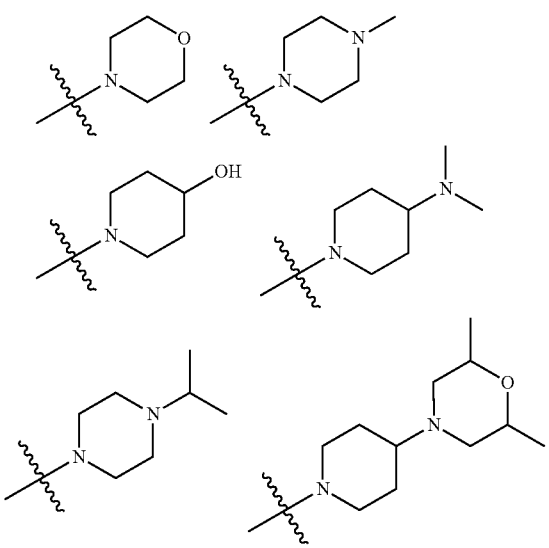

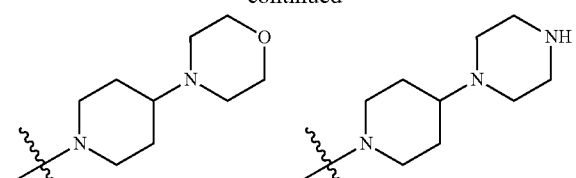
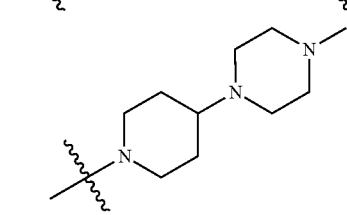
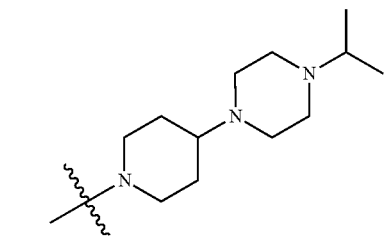
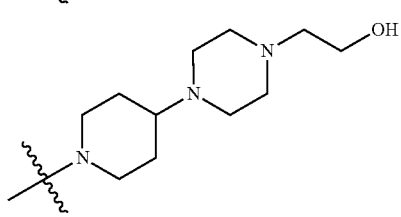
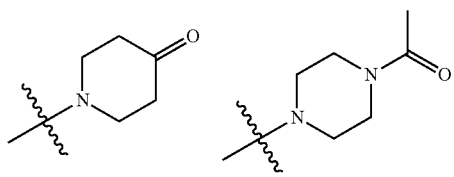
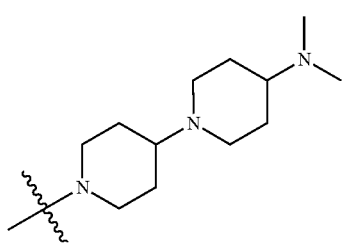
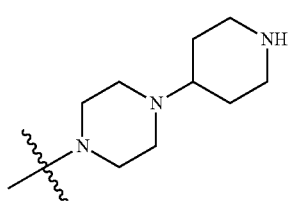
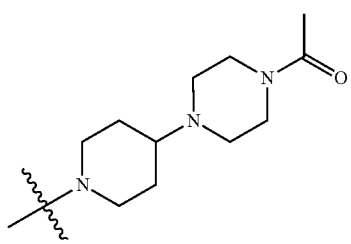
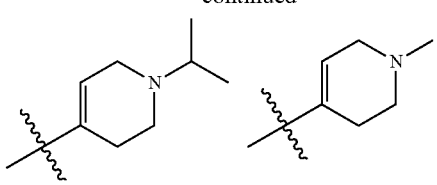
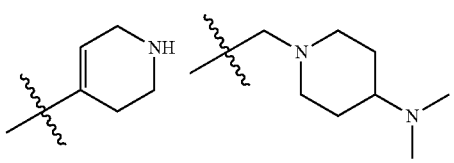
In some embodiments of the present disclosure, when $R_1$ is
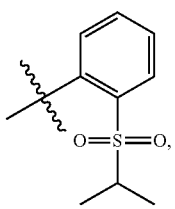 [SMILES: *c1ccccc1S(=O)(=O)C(C)C]
$R_3$ is any one of
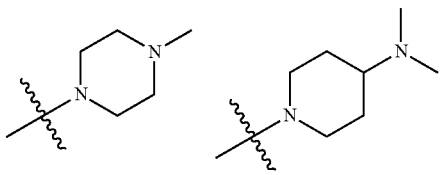
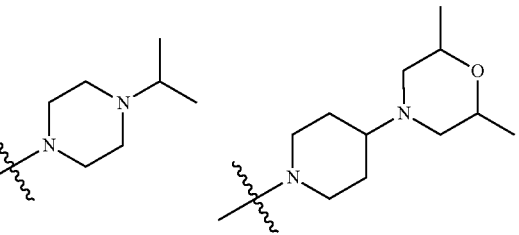
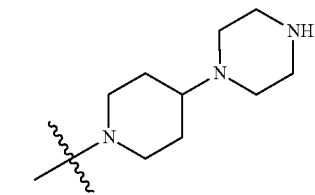
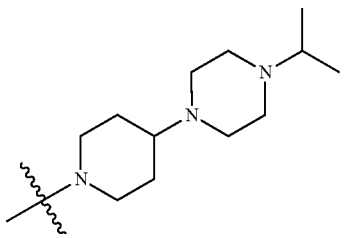
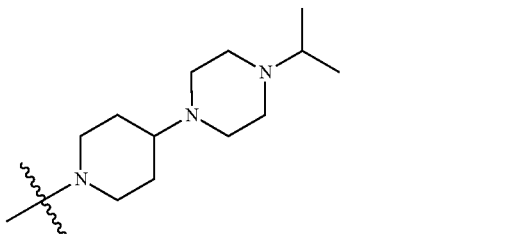

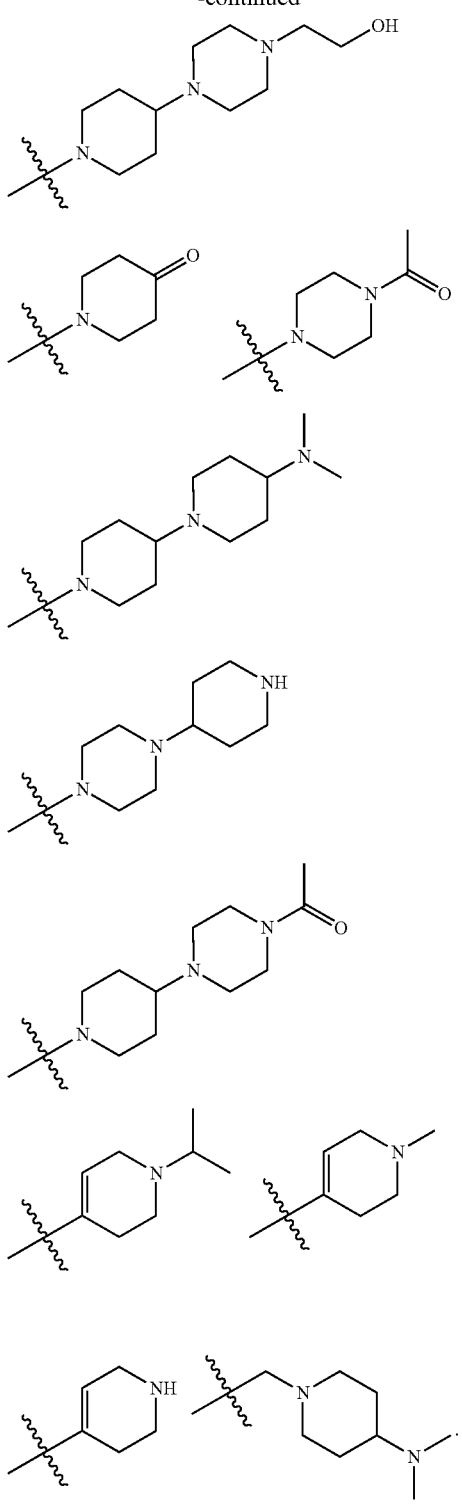

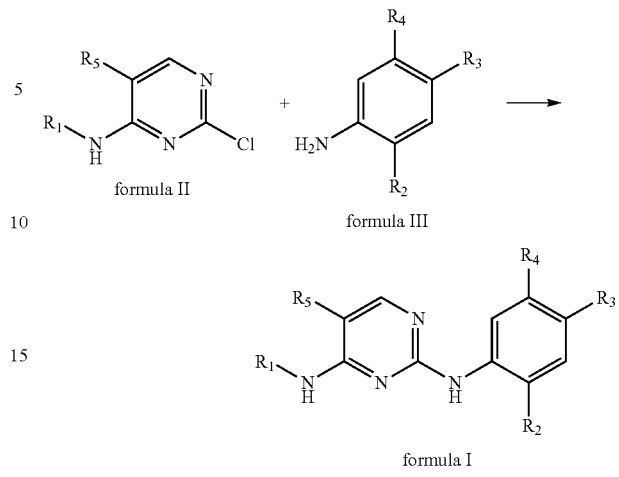

in which, $R_1$, $R_2$, $R_3$, $R_4$ and $R_5$ are defined as described in the present disclosure.

In some embodiments of the present disclosure, the compound of formula I can be synthesized by a displacement reaction between the compound of formula II and the compound of formula III, which is carried out by contacting such two compounds in an organic solvent in the presence of p-toluenesulfonic acid. In some embodiments of the present disclosure, the organic solvent can be n-butanol, which provides a suitable reaction condition for the compound of formula II and the compound of formula III, thereby contributing to improving yield of a target product and reaction efficiency, with side reaction reduced.

In some embodiments of the present disclosure, the compound of formula I is synthesized by a scheme below:

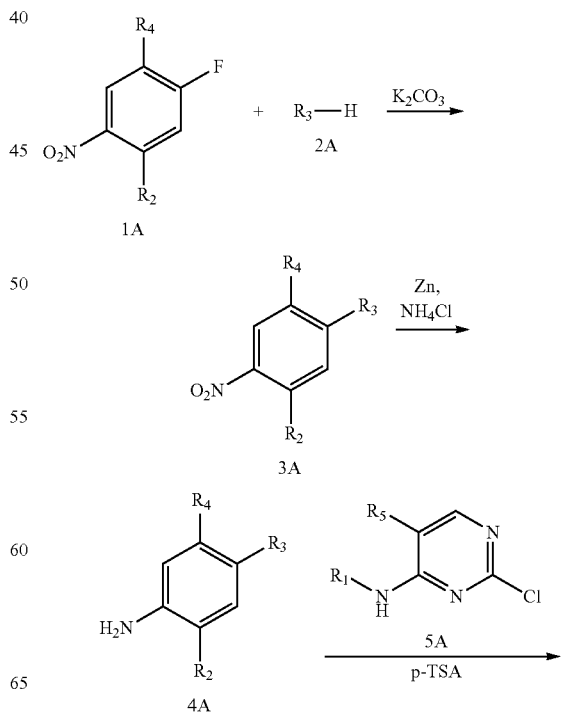

In some embodiments of the present disclosure, $R_4$ is hydrogen or methyl.

In some embodiments of the present disclosure, $R_5$ is chlorine or difluoromethoxy.

In some embodiments of the present disclosure, the present compound of formula I is synthesized by a scheme below:

-continued
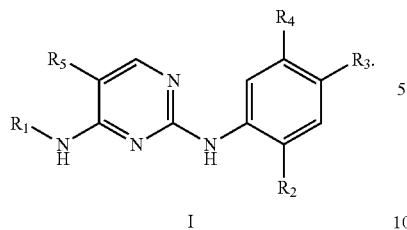
In some embodiments of the present disclosure, the compound of formula I-23 is synthesized by a scheme below:
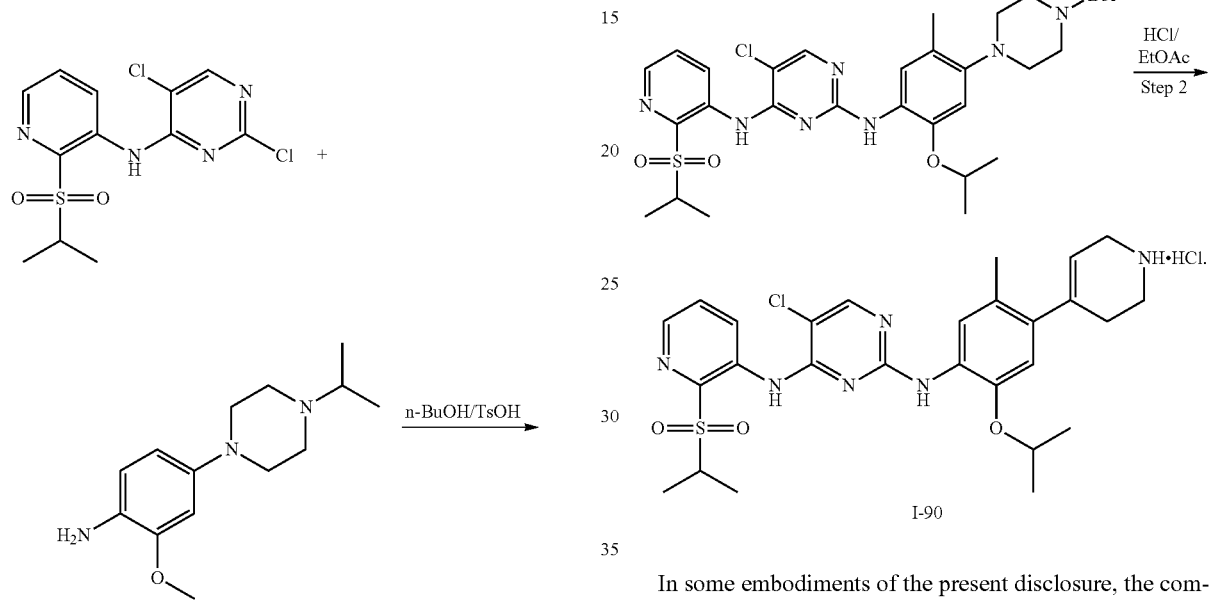
In some embodiments of the present disclosure, the compound of formula I-90 is synthesized by a scheme below:
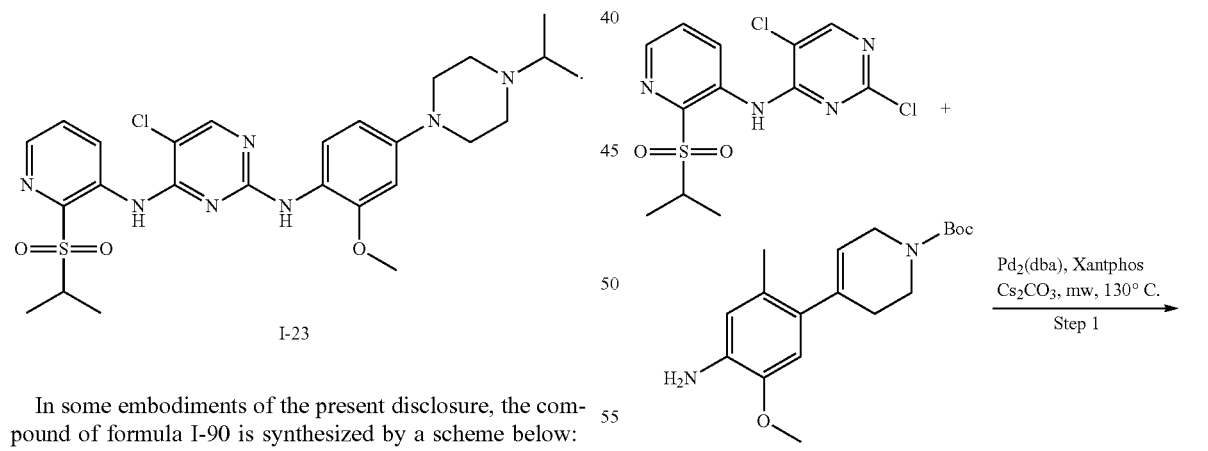
In some embodiments of the present disclosure, the compound of formula I-89 is synthesized by a scheme below
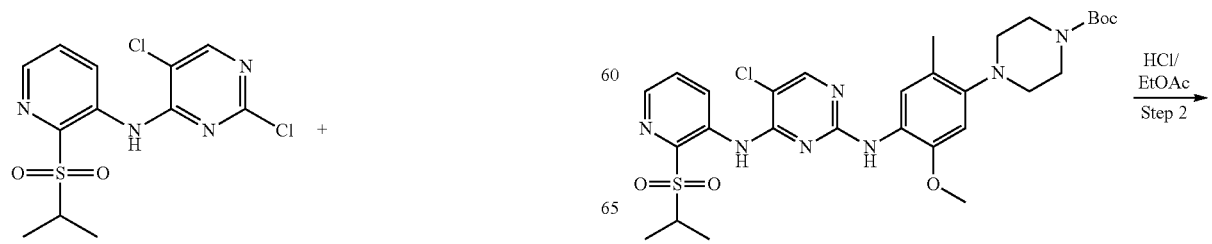

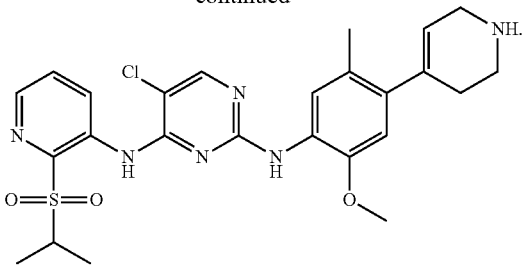

I-89

It is discovered by the present inventors that the compound of formula I can be synthesized rapidly and effectively by the method of the present disclosure, resulting in a target product with high yield and purity. The method is useful for industrialization owing to accessible raw materials, simple operation and post-treatment, and is environment-friendly as well.

In a third aspect, the present disclosure provides in embodiments a pharmaceutical composition, including a therapeutically effective amount of the compound descried in the first aspect.

The term "pharmaceutical composition" used herein includes one or more compounds of the present disclosure, a physiological/pharmaceutically acceptable salt or a prodrug thereof in combination with other chemical components such as a physiological/pharmaceutically acceptable carrier or excipient. The pharmaceutical composition is useful in administering to a subject, increasing absorption of active ingredients and improving their biological activities.

In some embodiments of the present disclosure, the pharmaceutical composition of the present disclosure includes the compound of formula I described above. In some embodiments of the present disclosure, the pharmaceutical composition is for inhibiting kinase, such as anaplastic lymphoma kinase, treating or preventing a cancer and/or suppressing proliferation of cancer cells. The cancer is lung cancer or anaplastic large cell non-Hodgkin lymphoma, for example the lung cancer is non-small cell lung cancer.

In some embodiments of the present disclosure, the pharmaceutical composition further includes a second therapeutic agent, in which said second therapeutic agent is different from the compound described above and said second therapeutic agent is useful in inhibiting kinase, such as anaplastic lymphoma kinase, treating or preventing a cancer or suppressing proliferation of cancer cells. In some embodiments of the present disclosure, the second therapeutic agent is administered in combination with the compound described above, such that the pharmaceutical composition is more useful in inhibiting kinase, such as anaplastic lymphoma kinase, treating or preventing a cancer or suppressing proliferation of cancer cells.

In some particular embodiments, the pharmaceutical composition further includes a pharmaceutically acceptable carrier, excipient, diluent, auxiliary, vehicle, or combination thereof.

In some particular embodiments, the pharmaceutical composition is in the form of tablets, capsules, injections, powder-injections, powders, syrups, solutions, suspensions or aerosols, thereby improving applicability of the pharmaceutical composition significantly. Moreover, the pharmaceutical composition described in the above embodiments can be existed in a suitable solid or liquid carrier or a diluent, or a suitable disinfector used for injection or instillation.

The various dosage forms of the present pharmaceutical composition can be prepared via general methods in the medical art. The present compound or the present pharmaceutical composition can be applied clinically to mammal, including human and animals via various administration routes, such as mouth, nose, skin, lung or gastrointestinal tract and so on. No matter how the compound or the pharmaceutical composition is administered, the best individual dosage depends on particular treatments. In general, the dosage starts from low dose and increases gradually until a most suitable dosage is achieved. For example, the compound or the pharmaceutical composition is administered orally.

In a fourth aspect, the present disclosure provides in embodiments use of the compound in the first aspect, the compound prepared by the method in the second aspect or the pharmaceutical composition in the third aspect in preparation a medicament.

In some particular embodiments, the medicament is for inhibiting kinase, such as anaplastic lymphoma kinase, treating or preventing a cancer or suppressing proliferation of cancer cells.

In some particular embodiments, the present compound of formula I inhibits anaplastic lymphoma kinase (ALK), particularly ALKL1196M kinase significantly, and suppresses proliferation of Karpas299 cells potently.

In some particular embodiments, the present compound of formula I also suppresses proliferation of Ba/F3 EML4-ALK cells potently.

In some particular embodiments, compared to positive control compounds Crizotinib and Ceritinib (LDK378), the present compounds outperform in water solubility according to Kinetic solubility tests.

In some particular embodiments, the present compound exhibits outstanding metabolic stability according to metabolic stability tests in vitro, thereby supporting its preclinical study greatly.

In some particular embodiments, the present compound has better membrane permeability over control compounds in a Caco-2 experiment, thus the present compound is easier to be absorbed in intestinal tracts with higher bioavailability than the control compounds.

The present compound can be used as an ALK inhibitor in preparation of an antitumor medicament for inhibiting anaplastic lymphoma kinase.

In some particular embodiments, the present compound of the formula I is for use in preparation of a medicament for treating a cancer, in which the cancer is lung cancer or anaplastic large cell non-Hodgkin lymphoma, for example, the cancer is non-small cell lung cancer.

Thus, the medicament prepared according to embodiments of the present disclosure can be used as an ALK inhibitor in treating one or more tumors related to activity of anaplastic lymphoma kinase (ALK) efficiently, said tumor including but not limited to lung cancer. The pyrimidine derivative disclosed herein represented in formula I, as an ALK inhibitor, can have a promising clinical and medical application.

In a fifth aspect, the present disclosure provides in embodiments that the compound or the pharmaceutical composition described above is for use in inhibiting kinase, such as anaplastic lymphoma kinase, treating or preventing a cancer or suppressing proliferation of cancer cells.

In a sixth aspect, the present disclosure provides in embodiments a method of inhibiting kinase, such as anaplastic lymphoma kinase, treating or preventing a cancer or suppressing proliferation of cancer cells. In some embodiments of the present disclosure, said method includes administering to a subject a therapeutically effective amount of the compound or the pharmaceutical composition described above.

In a seventh aspect, the present disclosure provides in embodiments a method of treating a tumor related to activity of anaplastic lymphoma kinase (ALK). In some embodiments of the present disclosure, said method includes administering to a subject a therapeutically effective amount of the compound or the pharmaceutical composition described above.

Additional aspects and advantages of the present disclosure will be set forth partly in the particular description and part of the disclosure will be apparent from such particular description, or from the practice of the present disclosure.

DETAILED DESCRIPTION

The embodiments of the present disclosure will be explained with reference to the following examples. It will be understood by those skilled in the art that the following examples are merely illustrative and should not be construed as limiting the scope of the present disclosure. The techniques or reaction conditions which are not particularly specified in the examples will be performed according to those described in the literature, or according to the product specifications. Reagents or apparatus, whose manufacturer information is not given, are commercially available products.

The present disclosure provides in examples a compound of formula I or a pharmaceutically acceptable salt, a hydrate, a solvate, a metabolite or a prodrug thereof, a method of preparing the same, an intermediate or a pharmaceutical composition including the same, or use of the compound or the pharmaceutical composition in preparation of a medicament.

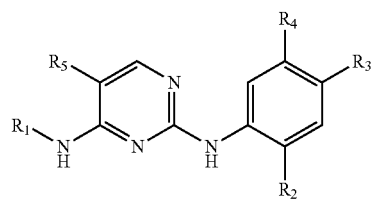

formula I

Example 1 Preparation Scheme of Compound I-17

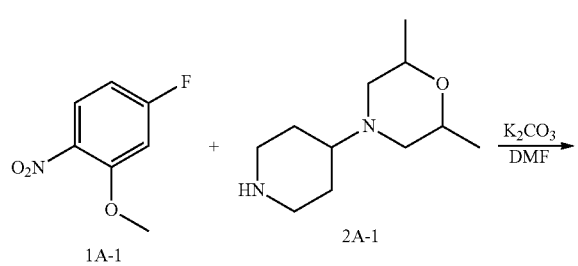

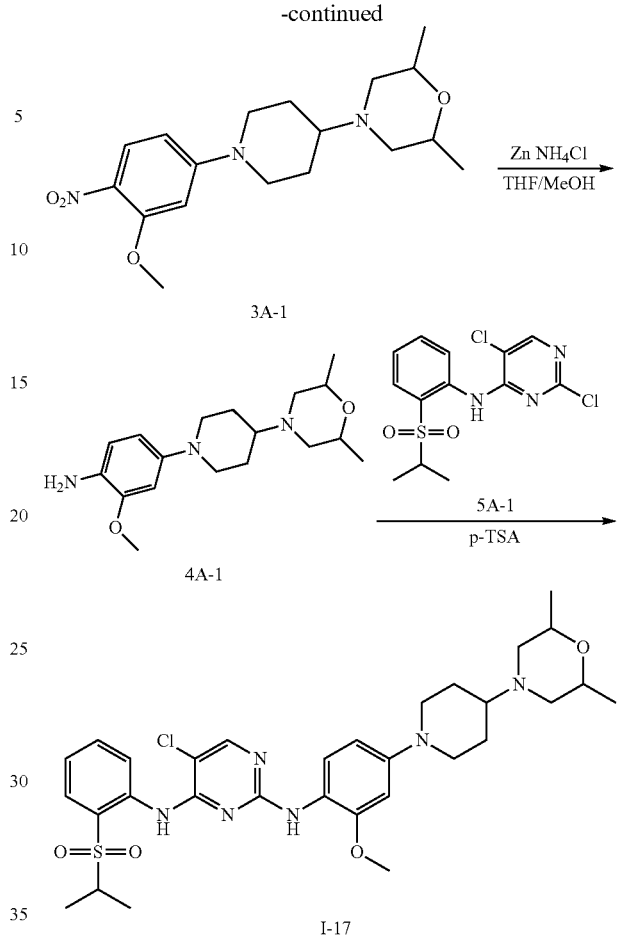

Step 1 Preparation of Compound 3A-1

To an anhydrous DMF solution (10 mL) was added compound 1A-1 (0.5 g, 2.92 mmol), compound 2A-1 (0.5 g, 2.52 mmol) and potassium carbonate (807 mg, 5.84 mmol), and then the mixture was heated to 80° C. and stirred for 5 hours. After TLC indicated the reaction was completed, the reaction mixture was extracted with ethyl acetate (100 mL), and washed with saturated aqueous sodium chloride three times, followed by phase separation. The organic phase was dried over anhydrous sodium sulfate, filtered and concentrated under reduced pressure to give a crude product 3A-1 (0.8 g, yield 78.4%), which was directly used for the next step without purification.

Step 2 Preparation of Compound 4A-1

The compound 3A-1 (0.8 g, 2.28 mmol) was dissolved in an aqueous solution of THF/MeOH (v/v=1:1, 20 mL in total) and saturated ammonium chloride (10 mL), with stirring for 10 min. Zinc powder (1.6 g) was added in portions, and the mixture was stirred at room temperature for 1 hour. After TLC indicated the reaction was completed, the reaction mixture was filtered and concentrated under reduced pressure to give a crude product, which was further isolated by column chromatography to obtain a compound 4A-1 (600 mg, yield 82.3%).

LCMS: t=0.079 min, 292.3 (M+H$^+$).

Step 3 Preparation of Compound I-17

To n-butanol (2 mL) was added compound 4A-1 (42 mg, 0.131 mmol) and compound 5A-1 (45 mg, 0.131 mmol), and then p-toluenesulfonic acid (23 mg, 0.132 mmol) was added under stirring. The mixture was heated to 100° C. and stirred for 5 hours. After TLC indicated the reaction was completed, the reaction mixture was concentrated under reduced pressure to give a crude product, which was further isolated by column chromatography to obtain a white solid product, compound I-17 (30 mg, yield 41.1%).

$^1$H NMR (400 MHz, cd$_3$od) δ 8.51 (d, J=8.3 Hz, 1H), 8.08 (s, 1H), 7.87 (d, J=8.0 Hz, 1H), 7.63 (dd. J=16.9, 8.0 Hz, 2H), 7.31 (t, J=7.7 Hz, 2H), 6.67 (d, J=2.2 Hz, 1H), 6.51 (dd, J=8.7, 2.1 Hz, 1H), 3.84 (s, 3H), 3.78-3.65 (m, 4H), 3.20 (m, 2H), 2.73 (dd, J=22.8, 11.1 Hz, 2H), 2.30-2.14 (m, 2H), 2.13-2.07 (m, 2H), 1.85-1.52 (m, 4H), 1.22 (dd, J=12.8, 6.5 Hz, 12H).

LCMS: t=0.730 min, 629.3 (M), 630.3 (M+1).

Example 2 Preparation Scheme of Compound I-12

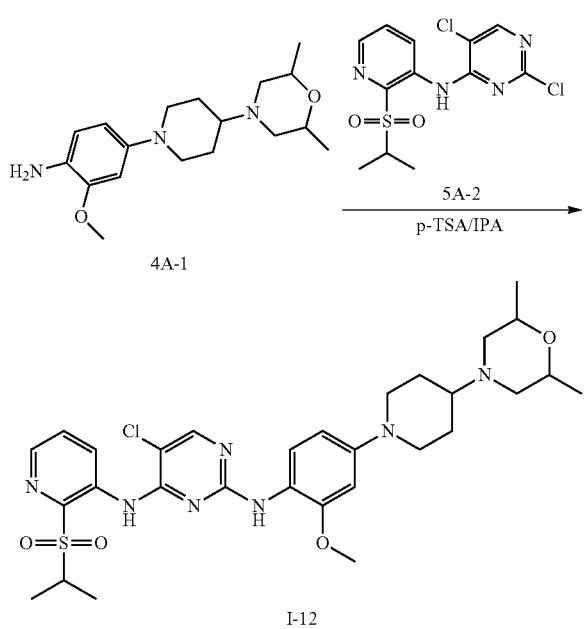

To n-butanol (2 mL) was added compound 4A-1 (41.85 mg, 0.131 mmol) and compound 5A-2 (45.48 mg, 0.131 mmol), and then p-toluenesulfonic acid (23 mg, 0.132 mmol) was added under stirring. The mixture was heated to 100° C. and stirred for 5 hours. After TLC indicated the reaction was completed, the reaction mixture was concentrated under reduced pressure to give a crude product, which was further purified and isolated by column chromatography to obtain an off-white solid product, compound I-12 (35 mg, yield 42.4%).

$^1$H NMR (400 MHz, cd$_3$od) δ 9.11 (d, J=8.6 Hz, 1H), 8.34 (dd, J=4.4, 1.3 Hz, 1H), 8.10 (s, 1H), 7.49 (dd, J=12.8, 6.5 Hz, 2H), 6.68 (d, J=2.4 Hz, 1H), 6.56 (dd, J=8.7, 2.5 Hz, 1H), 3.86-3.79 (m, 3H), 3.79-3.72 (m, 2H), 3.72-3.62 (m, 2H), 3.46 (d, J=7.2 Hz, 1H), 2.94 (d, J=11.0 Hz, 2H), 2.72 (t, J=11.5 Hz, 2H), 2.37 (d, J=11.4 Hz, 2H), 2.04 (d, J=12.2 Hz, 2H), 1.94 (t, J=10.9 Hz, 2H), 1.66 (ddd, J=24.2, 12.2, 3.8 Hz, 3H), 1.30 (t, J=4.8 Hz, 6H), 1.16 (d, J=6.3 Hz, 6H).

LCMS: t=0.718 min, 630.3 (M).

Example 3 Preparation Scheme of Compound I-4

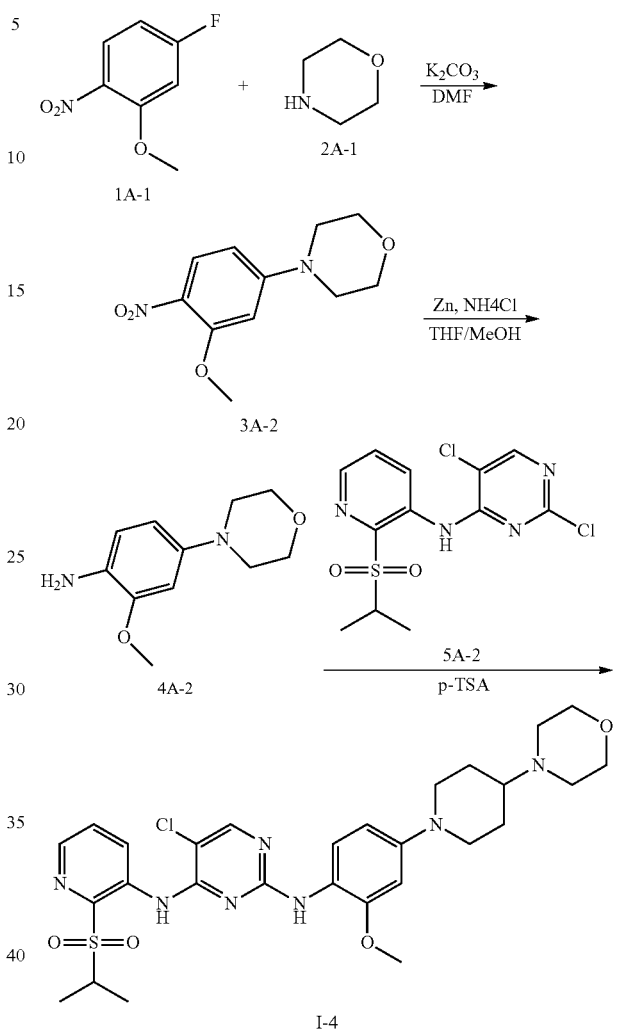

Step 1 Preparation of Compound 3A-2

To an anhydrous DMF solution (10 mL) was added compound 1A-1 (0.5 g, 2.92 mmol), compound 2A-2 (254.5 mg, 2.92 mmol) and potassium carbonate (1.21 g, 8.77 mmol), and then the mixture was heated to 80° C. and stirred for 5 hours. After TLC indicated the reaction was completed, the reaction mixture wad extracted with ethyl acetate (100 mL), and washed with saturated aqueous sodium chloride three times, followed by phase separation. The organic phase was dried over anhydrous sodium sulfate, filtered and concentrated under reduced pressure to give a crude product 3A-2 (566 mg, yield 81.3%), which was directly used for the next step without purification.

Step 2 Preparation of Compound 4A-2

The compound 3A-2 (0.54 g, 2.28 mmol) was dissolved in an aqueous solution of THF/MeOH (v/v=1:1, 20 mL in total) and saturated ammonium chloride (10 mL), with stirring for 10 min. Zinc powder (1.6 g) was added in portions, and the mixture was stirred at room temperature for 1 hour. After TLC indicated the reaction was completed, the reaction mixture was filtered and concentrated under reduced pressure to give a crude product, which was further isolated by column chromatography to obtain a compound 4A-2 (420 mg, yield 88.97%).

Step 3 Preparation of Compound I-4

To n-butanol (2 mL) was added compound 4A-2 (30 mg, 0.144 mmol) and compound 5A-2 (50 mg, 0.144 mmol), and then p-toluenesulfonic acid (24 mg, 0.145 mmol) was added under stirring. The mixture was heated to 100° C. and stirred for 5 hours. After TLC indicated the reaction was completed, the reaction mixture was concentrated under reduced pressure to give a crude product, which was further purified and isolated by column chromatography to obtain an off-white solid product, compound I-4 (27 mg, yield 36.1%).

$^1$H NMR (400 MHz, cd$_3$od) δ 9.10 (d, J=8.6 Hz, 1H), 8.34 (dd, J=4.4, 1.3 Hz, 1H), 8.10 (s, 1H), 7.55-7.45 (m, 2H), 6.67 (s, 1H), 6.55 (d, J=7.3 Hz, 1H), 3.85 (dd, J=8.7, 3.9 Hz, 4H), 3.83-3.74 (m, 4H), 3.16 (s, 4H), 1.30 (d, J=6.9 Hz, 6H).

LCMS: t=0.927 min, 518.15 (M), 519.2 (M+1)

Example 4 Preparation Scheme of Compound I-1

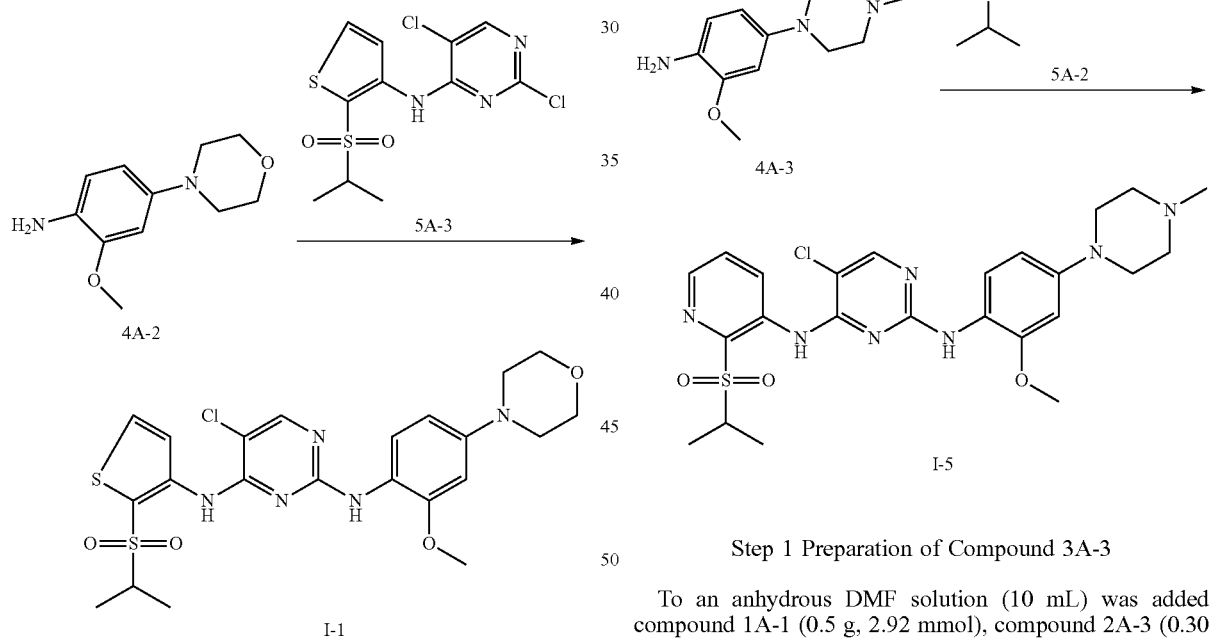

To n-butanol (2 mL) was added compound 4A-2 (30 mg, 0.144 mmol) and compound 5A-3 (50.7 mg, 0.144 mmol), and then p-toluenesulfonic acid (24.8 mg, 0.144 mmol) was added under stirring. The mixture was heated to 100° C. and stirred for 5 hours. After TLC indicated the reaction was completed, the reaction mixture was concentrated under reduced pressure to give a crude product, which was further purified and isolated by column chromatography to obtain an off-white solid product, compound I-1 (25 mg, yield 33.1%).

$^1$H NMR (400 MHz, cd$_3$od) δ 8.10 (s, 1H), 8.06 (s, 1H), 7.81 (d, J=5.5 Hz, 1H), 7.54 (d, J=8.6 Hz, 1H), 6.67 (d, J=2.4 Hz, 1H), 6.56 (dd, J=8.7, 2.2 Hz, 1H), 3.86 (dd, J=13.1, 8.4 Hz, 4H), 3.82 (s, 3H), 3.36 (dt, J=13.6, 6.8 Hz, 1H), 3.20-3.08 (m, 4H), 1.30 (t, J=7.8 Hz, 6H).

LCMS: t=0.799 min, 523.1 (M), 524.2 (M+1)

Example 5 Preparation Scheme of Compound I-5

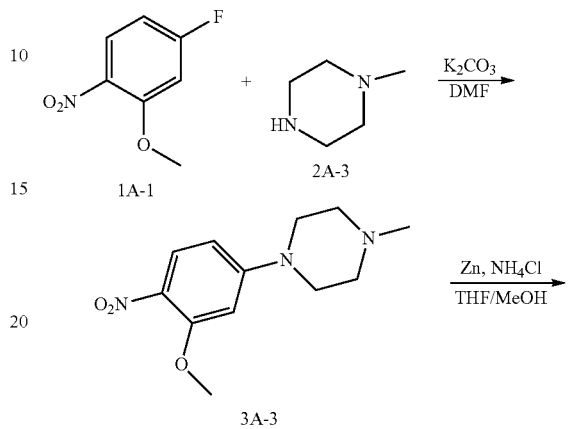

Step 1 Preparation of Compound 3A-3

To an anhydrous DMF solution (10 mL) was added compound 1A-1 (0.5 g, 2.92 mmol), compound 2A-3 (0.30 g, 2.92 mmol) and potassium carbonate (1.21 g, 8.77 mmol), and then the mixture was heated to 80° C. and stirred for 5 hours. After TLC indicated the reaction was completed, the reaction mixture wad extracted with ethyl acetate (100 mL), and washed with saturated aqueous sodium chloride three times, followed by phase separation. The organic phase was dried over anhydrous sodium sulfate, filtered and concentrated under reduced pressure to give a crude product 3A-3 (0.61 g, yield 83.3%), which was directly used for the next step without purification.

Step 2 Preparation of Compound 4A-3

The compound 3A-3 (0.57 g, 2.28 mmol) was dissolved in an aqueous solution of THF/MeOH (v/v=1:1, 20 mL in total) and saturated ammonium chloride (10 mL), with stirring for 10 min. Zinc powder (1.6 g) was added in portions, and the mixture was stirred at room temperature for 1 hour. After TLC indicated the reaction was completed, the reaction mixture was filtered and concentrated under reduced pressure to give a crude product, which was further isolated by column chromatography to obtain a compound 4A-3 (406 mg, yield 80.8%).

Step 3 Preparation of Compound I-5

To n-butanol (2 mL) was added compound 4A-3 (30 mg, 0.135 mmol) and compound 5A-2 (47 mg, 0.135 mmol), and then p-toluenesulfonic acid (23.3 mg, 0.135 mmol) was added under stirring. The mixture was heated to 100° C. and stirred for 5 hours. After TLC indicated the reaction was completed, the reaction mixture was concentrated under reduced pressure to give a crude product, which was further purified and isolated by column chromatography to obtain an off-white solid product, compound I-5 (59 mg, yield 81.8%).

$^1$H NMR (400 MHz, cd$_3$od) δ 9.09 (d, J=8.2 Hz, 1H), 8.33 (dd, J=4.3, 1.2 Hz, 1H), 8.09 (s, 1H), 7.54 (d, J=8.7 Hz, 1H), 7.48 (dd. J=8.7, 4.3 Hz, 1H), 6.67 (d, J=2.2 Hz, 1H), 6.54 (dd, J=8.7, 2.4 Hz, 1H), 3.89-3.73 (m, 4H), 3.27 (dd, J=9.3, 4.9 Hz, 4H), 2.89-2.73 (m, 4H), 2.49 (s, 3H), 1.30 (d, J=6.9 Hz, 6H).

LCMS: t=0.662 min, 532.3 (M), 534.3 (M+1).

Example 6 Preparation Scheme of Compound I-13

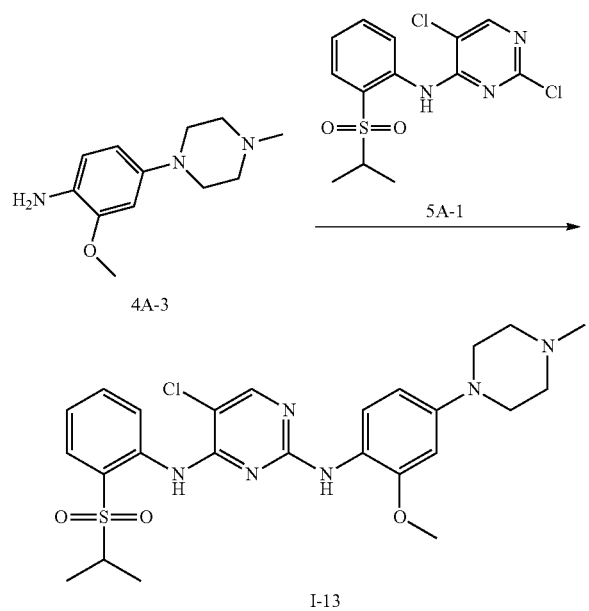

To n-butanol (2 mL) was added compound 4A-3 (30 mg, 0.135 mmol) and compound 5A-1 (47 mg, 0.135 mmol), and then p-toluenesulfonic acid (23.3 mg, 0.135 mmol) was added under stirring. The mixture was heated to 100° C. and stirred for 5 hours. After TLC indicated the reaction was completed, the reaction mixture was concentrated under reduced pressure to give a crude product, which was further purified and isolated by column chromatography to obtain an off-white solid product, compound I-13 (56 mg, yield 77.8%).

$^1$H NMR (400 MHz, cd$_3$od) δ 8.49 (d, J=8.4 Hz, 1H), 8.07 (s, 1H), 7.86 (dd, J=8.0, 1.3 Hz, 1H), 7.67 (d, J=8.7 Hz, 1H), 7.60 (dd, J=11.5, 4.3 Hz, 1H), 7.30 (t, J=7.6 Hz, 1H), 6.67 (s, 1H), 6.49 (dd, J=8.7, 2.1 Hz, 1H), 3.84 (s, 3H), 3.29-3.20 (m, 4H), 2.97-2.80 (m, 4H), 2.55 (s, 3H), 1.23 (d, J=6.8 Hz, 6H).

LCMS: t=0.685 min, 531.3 (M), 532.3 (M+1)

Example 7 Preparation Scheme of Compound I-2

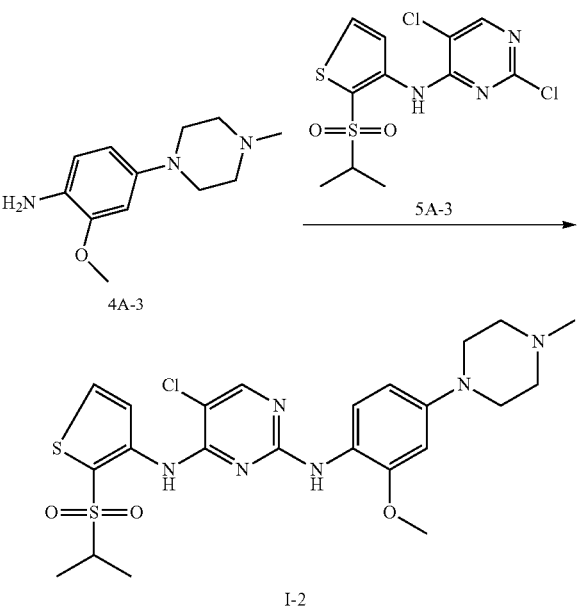

To n-butanol (2 mL) was added compound 4A-3 (30 mg, 0.135 mmol) and compound 5A-3 (48 mg, 0.135 mmol), and then p-toluenesulfonic acid (23 mg, 0.132 mmol) was added under stirring. The mixture was heated to 100° C. and stirred for 5 hours. After TLC indicated the reaction was completed, the reaction mixture was concentrated under reduced pressure to give a crude product, which was further purified and isolated by column chromatography to obtain an off-white solid product, compound I-2 (25 mg, yield 34.3%).

$^1$H NMR (400 MHz, cd$_3$od) δ 8.11 (s, 1H), 8.05 (s, 1H), 7.81 (d, J=5.5 Hz, 1H), 7.57 (d, J=8.6 Hz, 1H), 6.68 (d, J=2.3 Hz, 1H), 6.57 (dd, J=8.7, 2.4 Hz, 1H), 3.83 (s, 3H), 3.42-3.34 (m, 1H), 3.29 (s, 4H), 2.89 (s, 4H), 2.55 (s, 3H), 1.30 (d, J=6.7 Hz, 6H).

LCMS: t=0.690 min, 537.2 (M), 538.2 (M+1).

Example 8 Preparation Scheme of Compound I-8

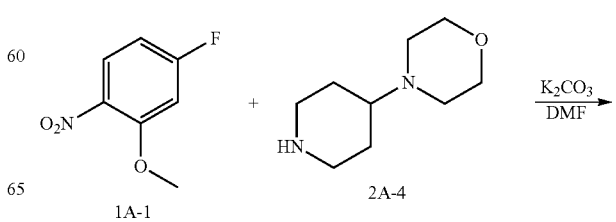

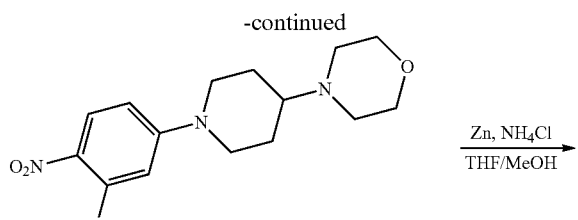

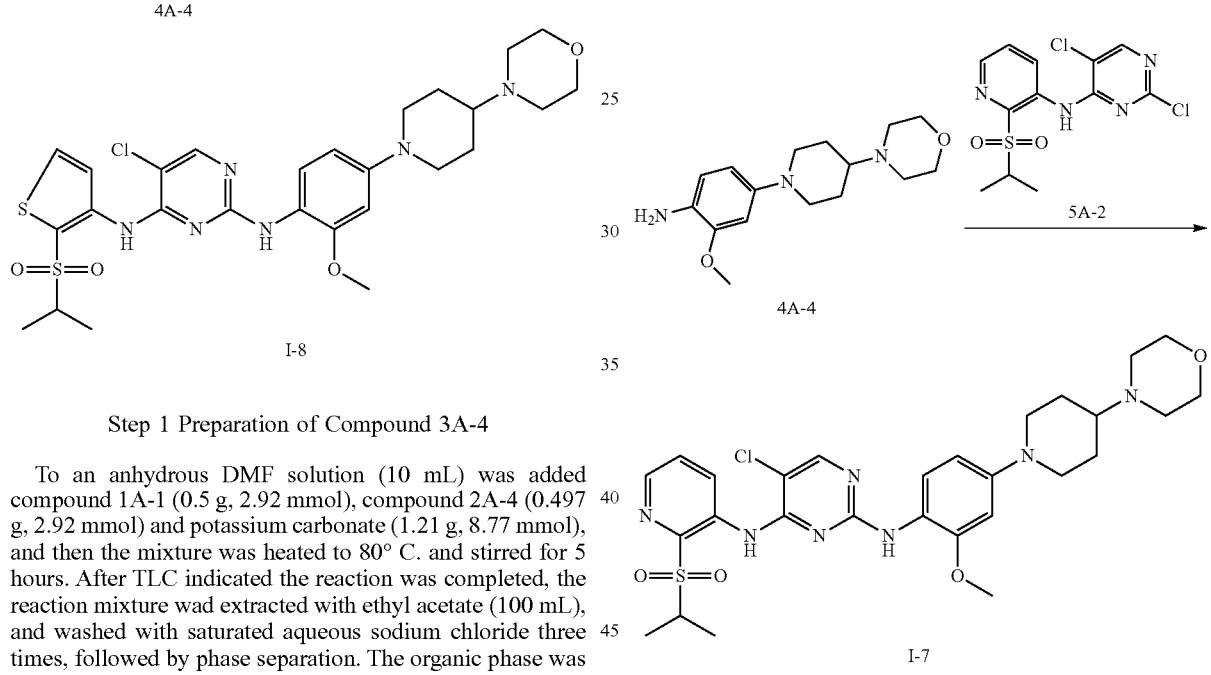

Step 1 Preparation of Compound 3A-4

To an anhydrous DMF solution (10 mL) was added compound 1A-1 (0.5 g, 2.92 mmol), compound 2A-4 (0.497 g, 2.92 mmol) and potassium carbonate (1.21 g, 8.77 mmol), and then the mixture was heated to 80° C. and stirred for 5 hours. After TLC indicated the reaction was completed, the reaction mixture wad extracted with ethyl acetate (100 mL), and washed with saturated aqueous sodium chloride three times, followed by phase separation. The organic phase was dried over anhydrous sodium sulfate, filtered and concentrated under reduced pressure to give a crude product 3A-4 (0.756 g, yield 80.5%), which was directly used for the next step without purification.

Step 2 Preparation of Compound 4A-4

The compound 3A-4 (0.73 g, 2.28 mmol) was dissolved in an aqueous solution of THF/MeOH (v/v=1:1, 20 mL in total) and saturated ammonium chloride (10 mL), with stirring for 10 min. Zinc powder (1.6 g) was added in portions, and the mixture was stirred at room temperature for 1 hour. After TLC indicated the reaction was completed, the reaction mixture was filtered and concentrated under reduced pressure to give a crude product, which was further isolated by column chromatography to obtain a compound 4A-4 (536 mg, yield 80.98%).

Step 3 Preparation of Compound I-8

To n-butanol (2 mL) was added compound 4A-4 (40 mg, 0.137 mmol) and compound 5A-3 (48 mg, 0.137 mmol), and then p-toluenesulfonic acid (24 mg, 0.137 mmol) was added under stirring. The mixture was heated to 100° C. and stirred for 5 hours. After TLC indicated the reaction was completed, the reaction mixture was concentrated under reduced pressure to give a crude product, which was further purified and isolated by column chromatography to obtain an off-white solid product, compound I-8 (25 mg, yield 30%).

$^1$H NMR (400 MHz, cd$_3$od) δ 8.20 (s, 1H), 8.04 (d, J=4.9 Hz, 2H), 7.48 (d, J=8.3 Hz, 1H), 7.14 (s, 1H), 6.99 (d, J=8.2 Hz, 1H), 4.11 (d, J=13.3 Hz, 2H), 3.97 (t, J=12.4 Hz, 2H), 3.94-3.81 (m, 5H), 3.60 (d, J=11.9 Hz, 3H), 3.45 (dt, J=13.6, 6.8 Hz, 1H), 3.28-3.21 (m, 2H), 2.43 (d, J=12.7 Hz, 2H), 2.17 (d, J=11.8 Hz, 2H), 1.30 (dd, J=15.3, 5.5 Hz, 6H).

LCMS: t=0.693 min, 607.3 (M), 608.3 (M+1), 609.3 (M+2).

Example 9 Preparation Scheme of Compound I-7

To n-butanol (2 mL) was added compound 4A-4 (40 mg, 0.137 mmol) and compound 5A-2 (47 mg, 0.137 mmol), and then p-toluenesulfonic acid (24 mg, 0.137 mmol) was added under stirring. The mixture was heated to 100° C. and stirred for 5 hours. After TLC indicated the reaction was completed, the reaction mixture was concentrated under reduced pressure to give a crude product, which was further purified and isolated by column chromatography to obtain an off-white solid product, compound I-7 (23 mg, yield 27.8%).

$^1$H NMR (400 MHz, cd$_3$od) δ 9.11 (d, J=8.0 Hz, 1H), 8.34 (dd, J-=4.4, 1.4 Hz, 1H), 8.10 (s, 1H), 7.49 (dd, J=12.8, 6.5 Hz, 2H), 6.68 (d, J=2.5 Hz, 1H), 6.56 (dd, J=8.7, 2.5 Hz, 1H), 3.88-3.80 (m, 4H). 3.75 (dd, J=13.4, 9.0 Hz, 6H), 2.83-2.60 (m, 6H), 2.42 (L J=11.4 Hz, 1H), 2.07 (d, J=12.2 Hz, 2H), 1.66 (ddd, J=24.2, 12.4, 4.0 Hz, 2H), 1.29 (t, J=7.0 Hz, 6H).

LCMS: t=0.682 min, 602.2 (M), 603.2 (M+1).

Example 10 Preparation Scheme of Compound I-6

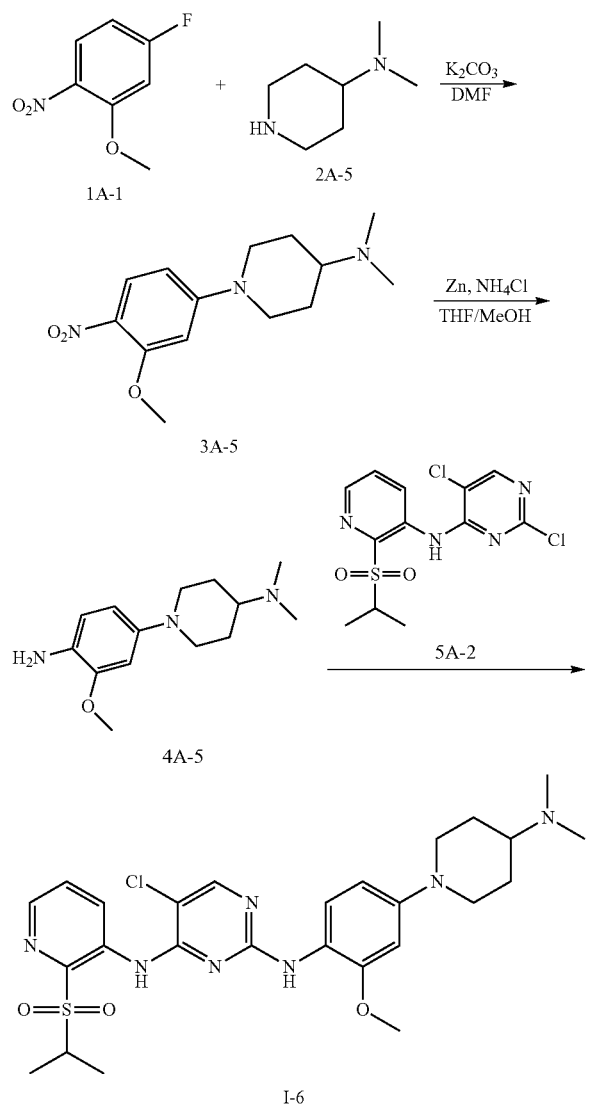

Step 1 Preparation of Compound 3A-5

To an anhydrous DMF solution (10 mL) was added compound 1A-1 (0.5 g, 2.92 mmol), compound 2A-5 (0.375 g, 2.92 mmol) and potassium carbonate (1.21 g, 8.77 mmol), and then the mixture was heated to 80° C. and stirred for 5 hours. After TLC indicated the reaction was completed, the reaction mixture wad extracted with ethyl acetate (100 mL), and washed with saturated aqueous sodium chloride three times, followed by phase separation. The organic phase was dried over anhydrous sodium sulfate, filtered and concentrated under reduced pressure to give a crude product 3A-5 (0.684 g, yield 83.8%), which was directly used for the next step without purification.

Step 2 Preparation of Compound 4A-5

The compound 3A-5 (0.64 g, 2.28 mmol) was dissolved in an aqueous solution of THF/MeOH (v/v=1:1, 20 mL in total) and saturated ammonium chloride (10 mL), with stirring for 10 min. Zinc powder (1.6 g) was added in portions, and the mixture was stirred at room temperature for 1 hour. After TLC indicated the reaction was completed, the reaction mixture was filtered and concentrated under reduced pressure to give a crude product, which was further isolated by column chromatography to obtain a compound 4A-5 (450 mg, yield 78.7%).

Step 3 Preparation of Compound I-6

To n-butanol (2 mL) was added compound 4A-5 (50 mg, 0.200 mmol) and compound 5A-2 (70 mg, 0.200 mmol), and then p-toluenesulfonic acid (35 mg, 0.200 mmol) was added under stirring. The mixture was heated to 100° C. and stirred for 5 hours. After TLC indicated the reaction was completed, the reaction mixture was concentrated under reduced pressure to give a crude product, which was further purified and isolated by column chromatography to obtain an off-white solid product, compound I-6 (78 mg, yield 69.4%).

$^1$H NMR (400 MHz, cd$_3$od) δ 9.11 (d, J=6.9 Hz, 1H), 8.36-8.31 (m, 1H), 8.09 (d, J=3.6 Hz, 1H), 7.58-7.45 (m, 2H), 6.67 (t, J=2.8 Hz, 1H), 6.57-6.50 (m, 1H), 3.92-3.76 (m, 6H), 3.40-3.31 (m, 1H), 2.90 (s, 6H), 2.79 (m, 2H), 2.18 (m, 2H), 1.87 (m, 2H), 1.29 (t, J=6.6 Hz, 6H).

LCMS: t=0.807 min, 559.2 (M), 560.2 (M+1)

Example 11 Preparation Scheme of Compound I-14

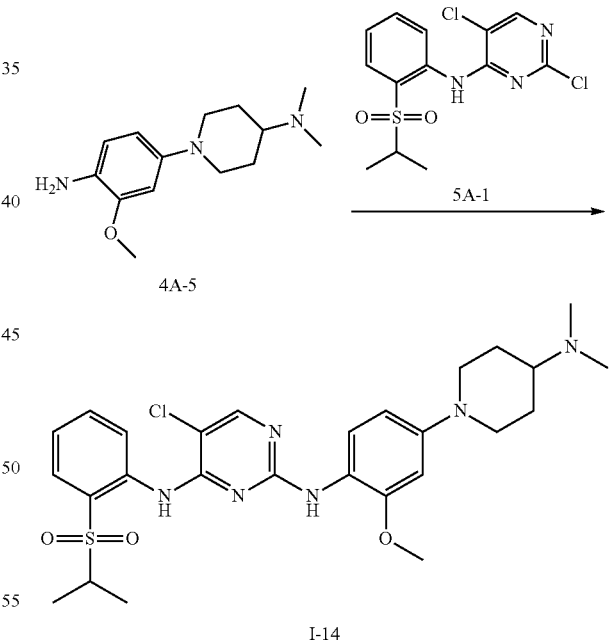

To n-butanol (2 mL) was added compound 4A-5 (50 mg, 0.200 mmol) and compound 5A-1 (69 mg, 0.200 mmol), and then p-toluenesulfonic acid (35 mg, 0.200 mmol) was added under stirring. The mixture was heated to 100° C. and stirred for 5 hours. After TLC indicated the reaction was completed, the reaction mixture was concentrated under reduced pressure to give a crude product, which was further purified and isolated by column chromatography to obtain an off-white solid product, compound I-14 (58 mg, yield 51.7%).

¹H NMR (400 MHz, cd₃od) δ 8.52 (d, J=8.4 Hz, 1H), 8.08 (s, 1H), 7.87 (dd, J=8.0, 1.5 Hz, 1H), 7.66 (d, J=8.7 Hz, 1H), 7.62 (t, J=7.2 Hz, 1H), 7.31 (t, J=7.2 Hz, 1H), 6.68 (s, 1H), 6.51 (dd, J=8.7, 2.5 Hz, 1H), 3.82-3.79 (m, 5H), 3.27-3.17 (m, 1H), 2.85 (s, 6H), 2.78-2.72 (m, 3H), 2.16-2.11 (m, 2H), 1.84-1.79 (m, 2H), 1.24 (d, J=6.8 Hz, 6H).

LCMS: t=0.692 min, 559.3 (M).

Example 12 Preparation Scheme of Compound I-3

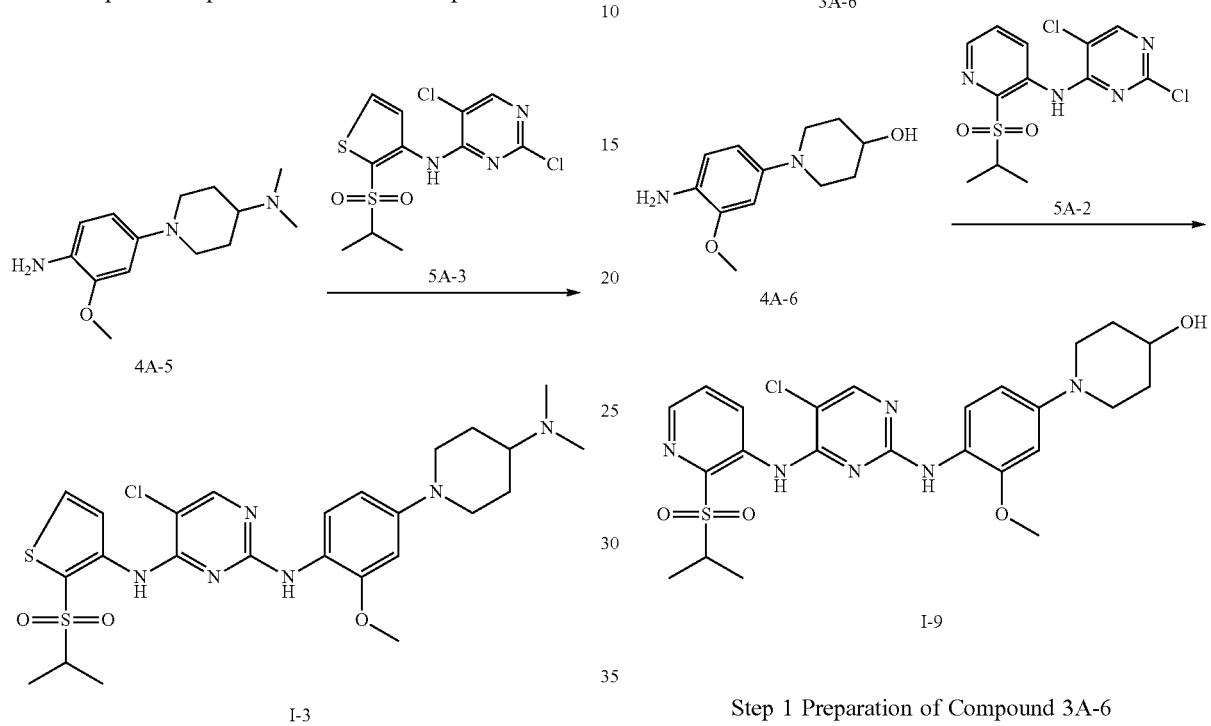

To n-butanol (2 mL) was added compound 4A-5 (30 mg, 0.120 mmol) and compound 5A-3 (42 mg, 0.120 mmol), and then p-toluenesulfonic acid (21 mg, 0.121 mmol) was added under stirring. The mixture was heated to 100° C. and stirred for 5 hours. After TLC indicated the reaction was completed, the reaction mixture was concentrated under reduced pressure to give a crude product, which was further purified and isolated by column chromatography to obtain an off-white solid product, compound I-3 (20 mg, yield 29.4%).

¹H NMR (400 MHz, cd₃od) δ 8.31 (s, 1H), 8.22 (d, J=10.3 Hz, 1H), 8.04 (d, J=4.8 Hz, 1H), 7.59-7.41 (m, 1H), 7.19 (s, 1H), 7.03 (d, J=7.7 Hz, 1H), 4.00-3.86 (m, 5H), 3.74-3.54 (m, 1H), 3.44 (m, 3H), 2.95 (s, 6H), 2.53-2.29 (m, 2H), 2.18 (m, 2H), 1.31 (t, J=10.4 Hz, 6H).

LCMS: t=0.689 min, 565.3 (M), 566.3 (M+1).

Example 13 Preparation Scheme of Compound I-9

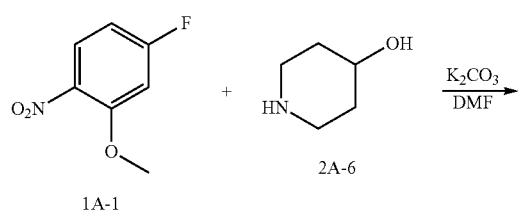

Step 1 Preparation of Compound 3A-6

To an anhydrous DMF solution (10 mL) was added compound 1A-1 (0.5 g, 2.92 mmol), compound 2A-6 (0.295 g, 2.92 mmol) and potassium carbonate (1.21 g, 8.77 mmol), and then the mixture was heated to 80° C. and stirred for 5 hours. After TLC indicated the reaction was completed, the reaction mixture wad extracted with ethyl acetate (100 mL), and washed with saturated aqueous sodium chloride three times, followed by phase separation. The organic phase was dried over anhydrous sodium sulfate, filtered and concentrated under reduced pressure to give a crude product 3A-6 (0.6 g, yield 81.4%), which was directly used for the next step without purification.

Step 2 Preparation of Compound 4A-6

The compound 3A-6 (0.58 g, 2.28 mmol) was dissolved in an aqueous solution of THF/MeOH (v/v=1:1, 20 mL in total) and saturated ammonium chloride (10 mL), with stirring for 10 min. Zinc powder (1.6 g) was added in portions, and the mixture was stirred at room temperature for 1 hour. After TLC indicated the reaction was completed, the reaction mixture was filtered and concentrated under reduced pressure to give a crude product, which was further isolated by column chromatography to obtain a compound 4A-6 (411 mg, yield 80.4%).

Step 3 Preparation of Compound I-9

To n-butanol (2 mL) was added compound 4A-6 (30 mg, 0.135 mmol) and compound 5A-2 (47 mg, 0.135 mmol), and then p-toluenesulfonic acid (24 mg, 0.135 mmol) was added under stirring. The mixture was heated to 100° C. and stirred for 5 hours. After TLC indicated the reaction was completed, the reaction mixture was concentrated under reduced pressure to give a crude product, which was further purified and isolated by column chromatography to obtain an off-white solid product, compound I-9 (41 mg, yield 57%).

$^1$H NMR (400 MHz, cd$_3$od) δ 8.65 (dd, J=5.4, 4.3 Hz, 2H), 8.32 (s, 1H), 7.82-7.68 (m, 2H), 7.47 (d, J=2.4 Hz, 1H), 7.21 (dd, J=8.7, 2.3 Hz, 1H), 4.12 (m, 1H), 4.04-3.91 (m, 4H), 3.84 (m, 2H), 3.65 (m, 2H), 2.39-2.23 (m, 2H), 2.12-2.03 (m, 2H), 1.36-1.22 (m, 6H).

LCMS: t=0.679 min, 533.2 (M), 534.3 (M+1).

Example 14 Preparation Scheme of Compound I-16

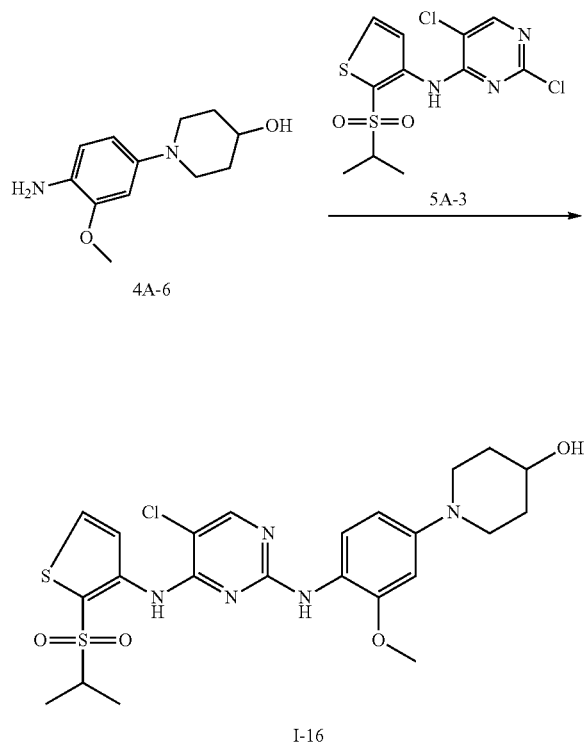

To n-butanol (2 mL) was added compound 4A-6 (30 mg, 0.135 mmol) and compound 5A-3 (47 mg, 0.135 mmol), and then p-toluenesulfonic acid (24 mg, 0.135 mmol) was added under stirring. The mixture was heated to 100° C. and stirred for 5 hours. After TLC indicated the reaction was completed, the reaction mixture was concentrated under reduced pressure to give a crude product, which was further purified and isolated by column chromatography to obtain an off-white solid product, compound I-16 (28 mg, yield 38.5%).

$^1$H NMR (400 MHz, cd$_3$od) δ 8.10 (s, 1H), 8.05 (s, 1H), 7.80 (d, J=5.5 Hz, 1H), 7.51 (d, J=8.7 Hz, 1H), 6.69 (d, J=2.5 Hz, 1H), 6.59 (dd, J=8.7, 2.5 Hz, 1H), 3.82 (s, 3H), 3.80-3.72 (m, 1H), 3.64-3.50 (m, 2H), 3.35 (dd, J=13.6, 6.8 Hz, 1H), 2.98-2.83 (m, 2H), 2.05-1.91 (m, 2H), 1.75-1.58 (m, 2H), 1.31 (d, J=6.8 Hz, 6H).

LCMS: t=0.734 min, 538.2 (M), 539.2 (M+1)

Example 15 Preparation Scheme of Compound I-10

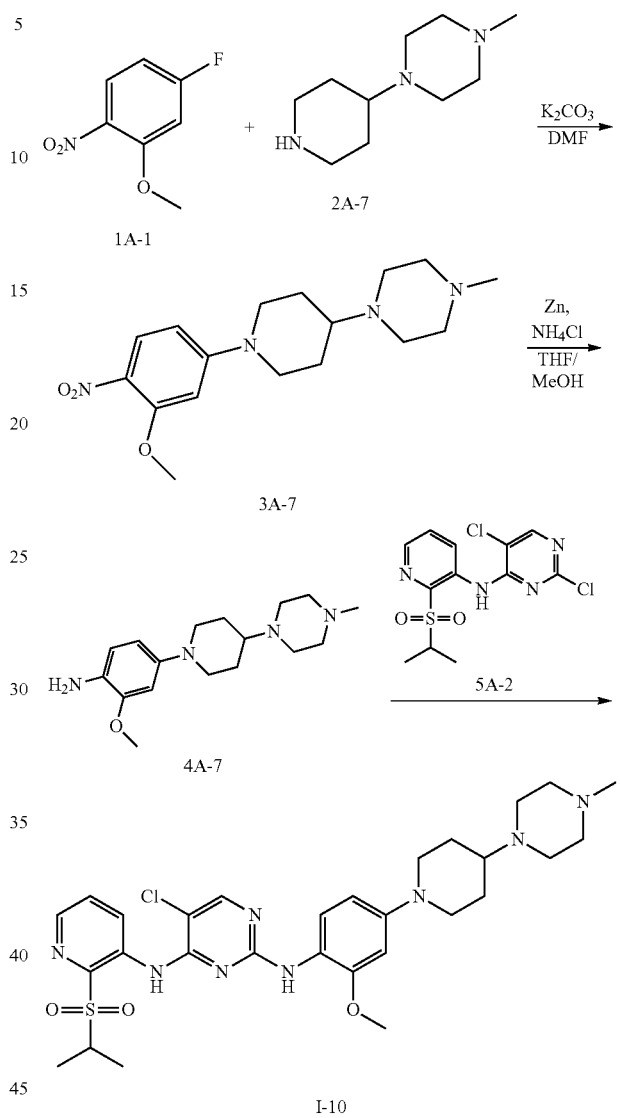

Step 1 Preparation of Compound 3A-7

To an anhydrous DMF solution (10 mL) was added compound 1A-1 (0.5 g, 2.92 mmol), compound 2A-7 (0.53 g, 2.92 mmol) and potassium carbonate (1.21 g, 8.77 mmol), and then the mixture was heated to 80° C. and stirred for 5 hours. After TLC indicated the reaction was completed, the reaction mixture wad extracted with ethyl acetate (100 mL), and washed with saturated aqueous sodium chloride three times, followed by phase separation. The organic phase was dried over anhydrous sodium sulfate, filtered and concentrated under reduced pressure to give a crude product 3A-7 (0.826 g, yield 84.5%), which was directly used for the next step without purification.

Step 2 Preparation of Compound 4A-7

The compound 3A-7 (0.76 g, 2.28 mmol) was dissolved in an aqueous solution of THF/MeOH (v/v=1:1, 20 mL in total) and saturated ammonium chloride (10 mL), with stirring for 10 min. Zinc powder (1.6 g) was added in portions, and the mixture was stirred at room temperature for 1 hour. After TLC indicated the reaction was completed, the reaction mixture was filtered and concentrated under reduced pressure to give a crude product, which was further isolated by column chromatography to obtain a compound 4A-7 (566 mg, yield 81.8%).

Step 3 Preparation of Compound I-10

To n-butanol (2 mL) was added compound 4A-7 (40 mg, 0.131 mmol) and compound 5A-2 (45.6 mg, 0.131 mmol), and then p-toluenesulfonic acid (23 mg, 0.132 mmol) was added under stirring. The mixture was heated to 100° C. and stirred for 5 hours. After TLC indicated the reaction was completed, the reaction mixture was concentrated under reduced pressure to give a crude product, which was further purified and isolated by column chromatography to obtain an off-white solid product, compound I-10 (30 mg, yield 37.11%).

$^1$H NMR (400 MHz, cd$_3$od) δ 9.10 (d, J=8.3 Hz, 1H), 8.33 (d, J=4.3 Hz, 1H), 8.09 (d, J=2.3 Hz, 1H), 7.57-7.41 (m, 2H), 6.66 (d, J=2.3 Hz, 1H), 6.54 (dd, J=8.7, 2.5 Hz, 1H), 3.92-3.62 (m, 6H), 3.21-2.81 (m, 7H), 2.73 (dd, J=24.5, 12.5 Hz, 3H), 2.65 (s, 3H), 2.04 (d, J=11.9 Hz, 2H), 1.71 (dt, J=11.7, 8.6 Hz, 2H), 1.29 (t, J=6.8 Hz, 6H).

LCMS: t=0.665 min, 615.3 (M), 616.2 (M+1)

Example 16 Preparation Scheme of Compound I-11

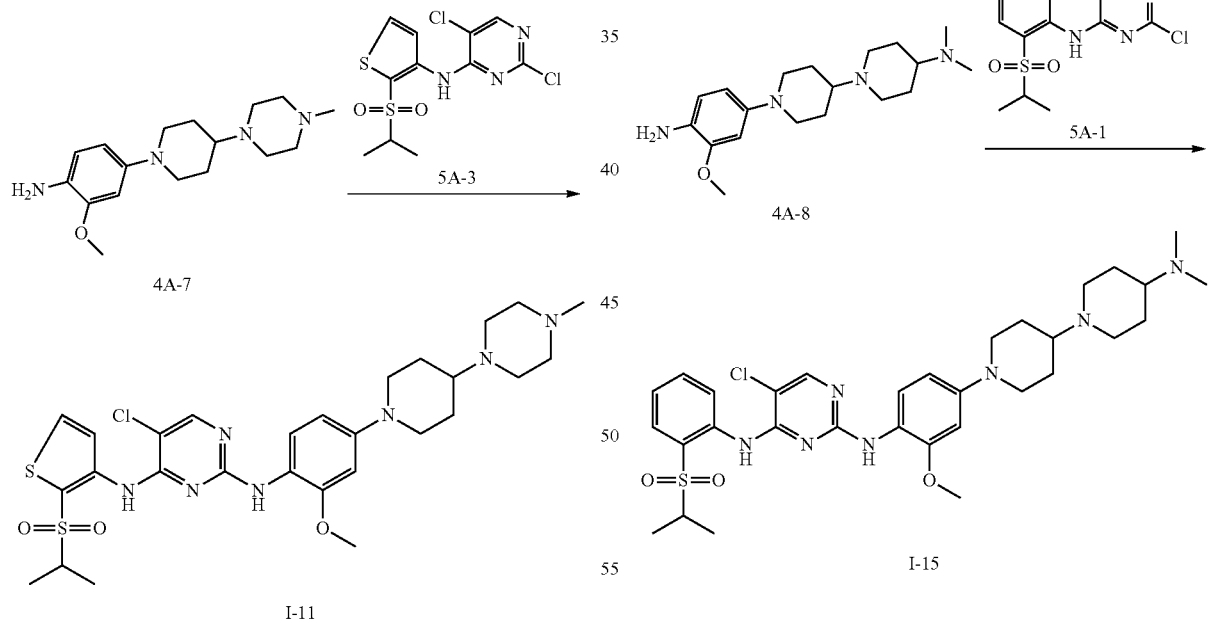

To n-butanol (2 mL) was added compound 4A-7 (40 mg, 0.131 mmol) and compound 5A-3 (46 mg, 0.131 mmol), and then p-toluenesulfonic acid (23 mg, 0.132 mmol) was added under stirring. The mixture was heated to 100° C. and stirred for 5 hours. After TLC indicated the reaction was completed, the reaction mixture was concentrated under reduced pressure to give a crude product, which was further purified and isolated by column chromatography to obtain an off-white solid product, compound I-11 (18 mg, yield 22%).

Example 17 Preparation Scheme of Compound I-15

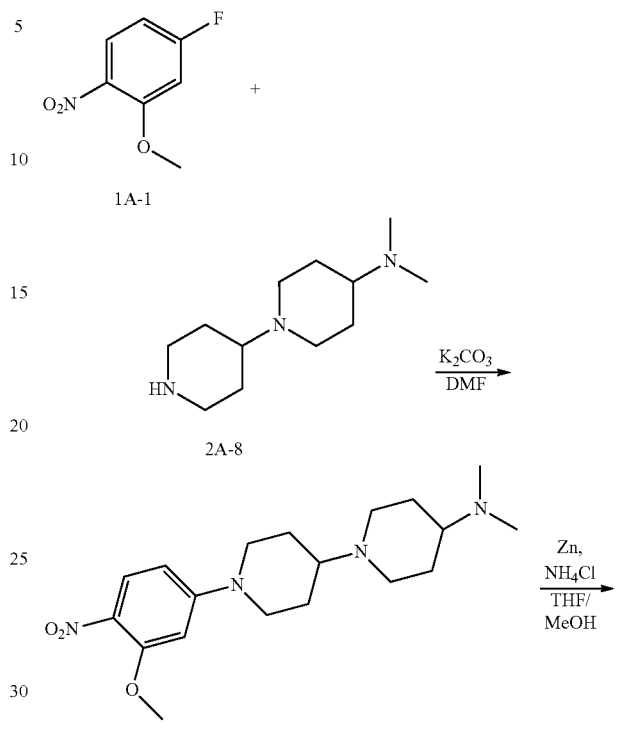

Step 1 Preparation of Compound 3A-8

To an anhydrous DMF solution (10 mL) was added compound 1A-1 (0.5 g, 2.92 mmol), compound 2A-8 (0.617 g, 2.92 mmol) and potassium carbonate (1.21 g, 8.77 mmol), and then the mixture was heated to 80° C. and stirred for 5 hours. After TLC indicated the reaction was completed, the reaction mixture wad extracted with ethyl acetate (100 mL), and washed with saturated aqueous sodium chloride three times, followed by phase separation. The organic phase was dried over anhydrous sodium sulfate, filtered and concentrated under reduced pressure to give a crude product 3A-8 (0.856 g, yield 80.8%), which was directly used for the next step without purification.

Step 2 Preparation of Compound 4A-8

The compound 3A-8 (0.83 g, 2.28 mmol) was dissolved in an aqueous solution of THF/MeOH (v/v=1:1, 20 mL in total) and saturated ammonium chloride (10 mL), with stirring for 10 min. Zinc powder (1.6 g) was added in portions, and the mixture was stirred at room temperature for 1 hour. After TLC indicated the reaction was completed, the reaction mixture was filtered and concentrated under reduced pressure to give a crude product, which was further isolated by column chromatography to obtain a compound 4A-8 (650 mg, yield 85.4%).

Step 3 Preparation of Compound I-15

To n-butanol (2 mL) was added compound 4A-8 (40 mg, 0.120 mmol) and compound 5A-2 (42 mg, 0.120 mmol), and then p-toluenesulfonic acid (21 mg, 0.120 mmol) was added under stirring. The mixture was heated to 100° C. and stirred for 5 hours. After TLC indicated the reaction was completed, the reaction mixture was concentrated under reduced pressure to give a crude product, which was further purified and isolated by column chromatography to obtain an off-white solid product, compound I-15 (20 mg, yield 25.8%).

Example 18 Preparation Scheme of Compound I-18

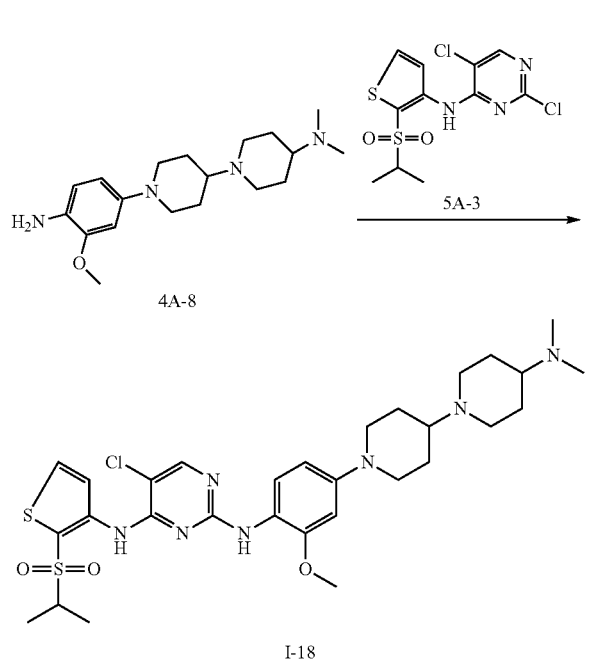

To n-butanol (2 mL) was added compound 4A-8 (40 mg, 0.120 mmol) and compound 5A-3 (42 mg, 0.120 mmol), and then p-toluenesulfonic acid (21 mg, 0.120 mmol) was added under stirring. The mixture was heated to 100° C. and stirred for 5 hours. After TLC indicated the reaction was completed, the reaction mixture was concentrated under reduced pressure to give a crude product, which was further purified and isolated by column chromatography to obtain an off-white solid product, compound I-18 (16 mg, yield 20.5%).

Example 19 Preparation of 5-chlorine-$N^2$-(4-(4-(isopropylpyrazin-1-yl)-2-methoxyphenyl)-$N^4$-(2-(isopropylsulfonyl) pyridin-3-yl) pyrimidine-2,4-diamine (Compound I-23)

Preparation Scheme

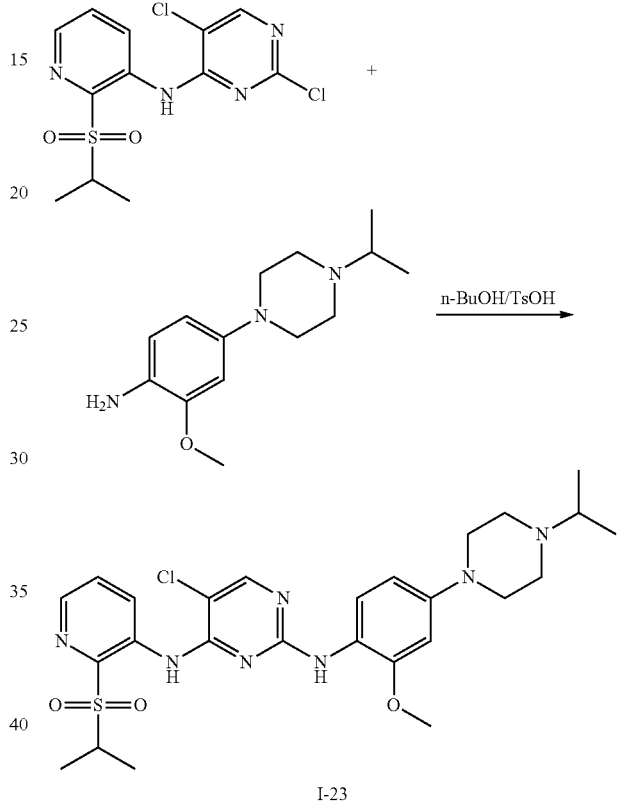

To n-butanol (n-BuOH, 2.5 mL) was added 2,5-dichloro-N-(2-(isopropylsulfonyl) pyridin-3-yl) pyrimidine-4-amine (183 mg, 0.527 mmol) and 4-(4-isopropylpyrazin-1-yl)-2-methoxyaniline (131 mg, 0.527 mmol), and then p-toluenesulfonic acid (91 mg, 0.527 mmol) was added. The mixture was heated to 120° C. and stirred for 3 hours. After LCMS indicated the reaction was completed, the reaction mixture was cooled to room temperature, then diluted with ethyl acetate (25 mL), washed with water and saturated aqueous sodium chloride, dried over anhydrous sodium sulfate, filtered and concentrated to give a crude product, which was further purified and isolated by column chromatography to obtain a yellow solid product, compound I-23 (159 mg, yield 53.8%).

$^1$H NMR (400 MHz, CDCl$_3$): δ 10.06 (s, 1H), 9.18 (d, J=8.4 Hz, 1H), 8.36 (s, 1H), 8.14 (s, 1H), 7.88 (d, J=8.0 Hz, 1H), 7.43 (s, 1H), 7.19 (s, 1H), 6.56 (s, 1H), 6.50 (d, J=8.0 Hz, 1H), 3.86 (s, 4H), 3.23 (s, 4H), 2.76 (s, 5H), 1.37 (d, J=6.4 Hz, 6H), 1.14 (d, J=4.4 Hz, 6H).

LCMS: t=3.17 min, 560.1 (M+H$^+$).

During preparation of the compound I-23, said 4-(4-isopropylpyrazin-1-yl)-2-methoxyaniline, re resented in formula 1, was synthesized by a route below

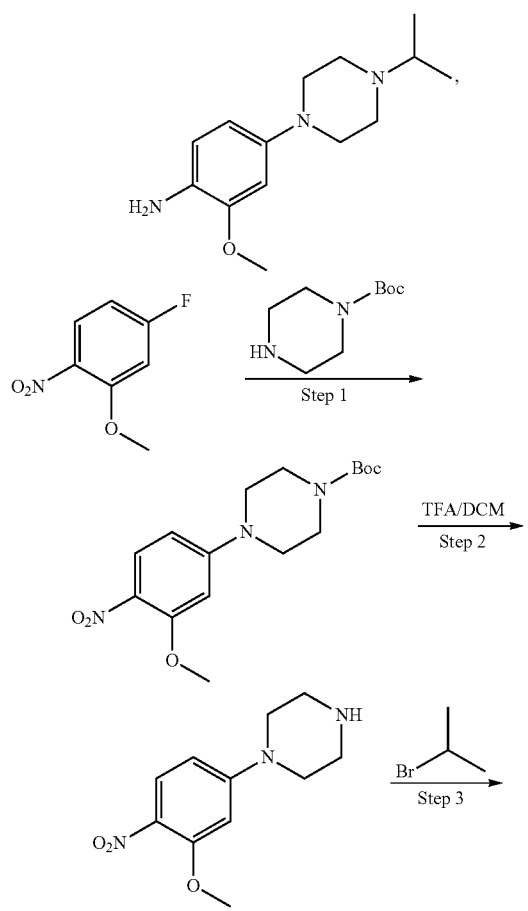

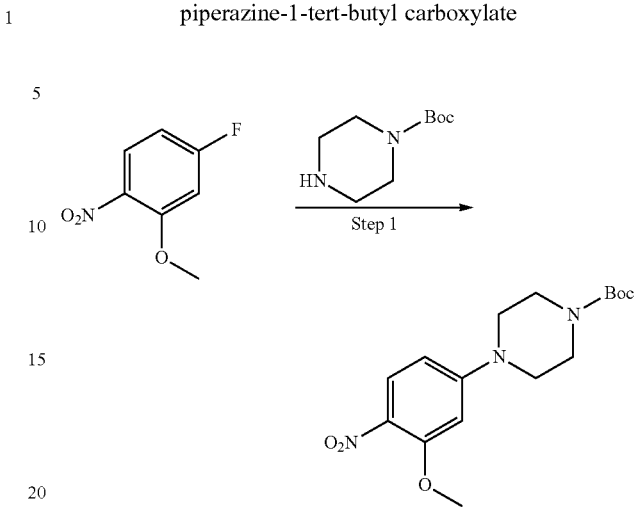

Step 1 Preparation of 4-(3-methoxy-4-nitrophenyl) piperazine-1-tert-butyl carboxylate Compound 4-fluoro-2-methoxy-1 nitrobenzene (3 g, 17.53 mmol) was dissolved in DMF (10 mL), and tert-butyl piperazine-1-carboxylate (3.59 g, 19.28 mmol) and cesium carbonate (17.14 g, 52.6 mmol) were added under stirring. The mixture was heated to 80° C. and reacted overnight. After TLC indicated the reaction was completed, the reaction mixture was cooled to room temperature, diluted with 100 mL water, and extracted with DCM/i-PrOH (3:1) (50 mL×3). The combined organic phase was washed with saturated aqueous sodium chloride, dried over anhydrous sodium sulfate, filtered and evaporated to remove solvent, thus obtaining a yellow oily product (5.4 g, yield 91%).

LCMS: t=3.88 min, 282.0 (M-55).

Step 2 Preparation of 1-(3-methoxy-4-nitrophenyl) piperazine

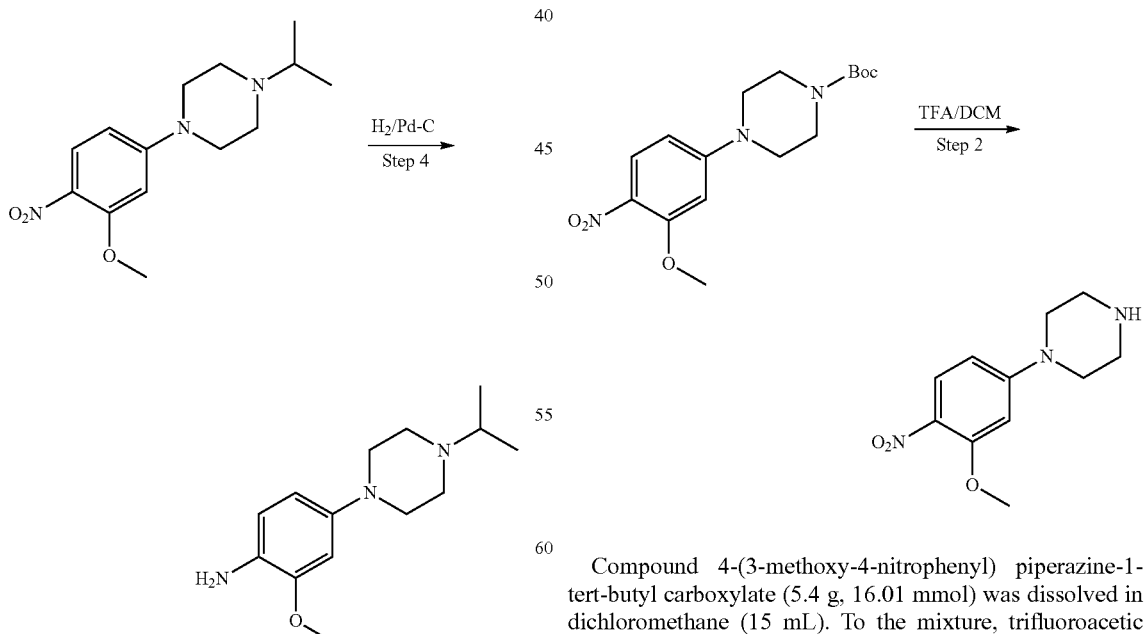

Compound 4-(3-methoxy-4-nitrophenyl) piperazine-1-tert-butyl carboxylate (5.4 g, 16.01 mmol) was dissolved in dichloromethane (15 mL). To the mixture, trifluoroacetic acid (5 mL) was added slowly at room temperature under stirring. The reaction mixture was stirred overnight at room temperature, and evaporated rotarily to remove solvent, thus obtaining a black oily product (3.8 g, yield 100%).

Step 3 Preparation of 1-isopropyl-4-(3-methoxy-4-nitrophenyl) piperazine

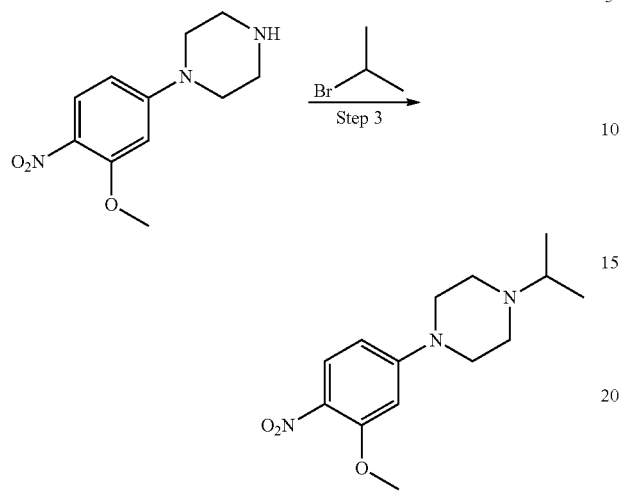

Compound 1-(3-methoxy-4-nitrophenyl) piperazine trifluoroacetate salt (3.8 g, 16 mmol) was dissolved in DMF (15 mL), and potassium carbonate (6.64 g, 48.0 mmol) and isopropyl bromide (4.53 ml, 32.0 mmol) were added under stirring. The mixture was heated to 80° C. and stirred for 4 hours. After TLC indicated the reaction was completed, the reaction mixture was cooled to room temperature, diluted with water, and extracted with EtOAc. The organic phase was washed with water, dried over anhydrous sodium sulfate, filtered and evaporated to give a crude product, which was further purified and isolated by column chromatography to obtain a green oily product (4.2 g, yield 52%).

LCMS: t=1.57 min, 280.1 (M+H$^+$).

Step 4 Preparation of 4-(4-isopropyl piperazin-1-yl)-2-methoxyaniline

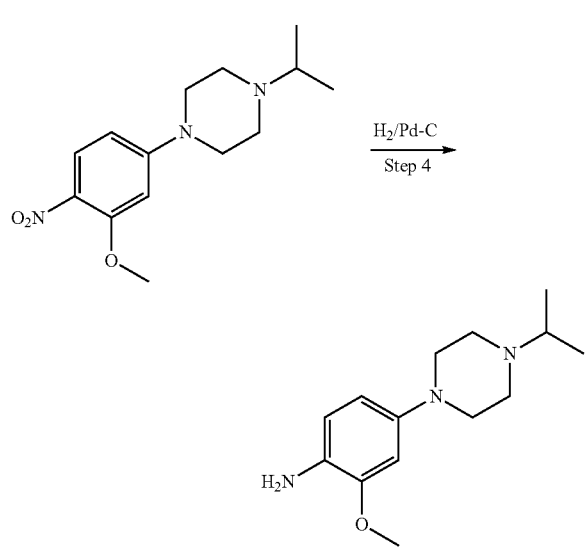

Compound 1-isopropyl-4-(3-methoxy-4-nitrophenyl) piperazine (4.2 g, 11.73 mmol) was dissolved in methanol (50 mL), followed by purged with nitrogen and then added with palladium on carbon (125 mg). After nitrogen was replaced with hydrogen, the reaction mixture was stirred under hydrogen atmosphere at room temperature overnight. After TLC indicated the reaction was completed, palladium on carbon was removed by filtration and the mixture was concentrated under reduced pressure to give a black oily product (0.4 g, yield 13%).

LCMS: t=0.43 min, 250.1 (M+H$^+$).

Example 20 Preparation of 5-chloro-N$^2$-(4-(4-(dimethylamino) piperidin-1-yl)-2-isopropoxyphenyl-N$^4$-(2-(isopropylsulfonyl) pyridin-3-yl) pyrimidine-2,4-diamine (Compound I-91)

Preparation Scheme

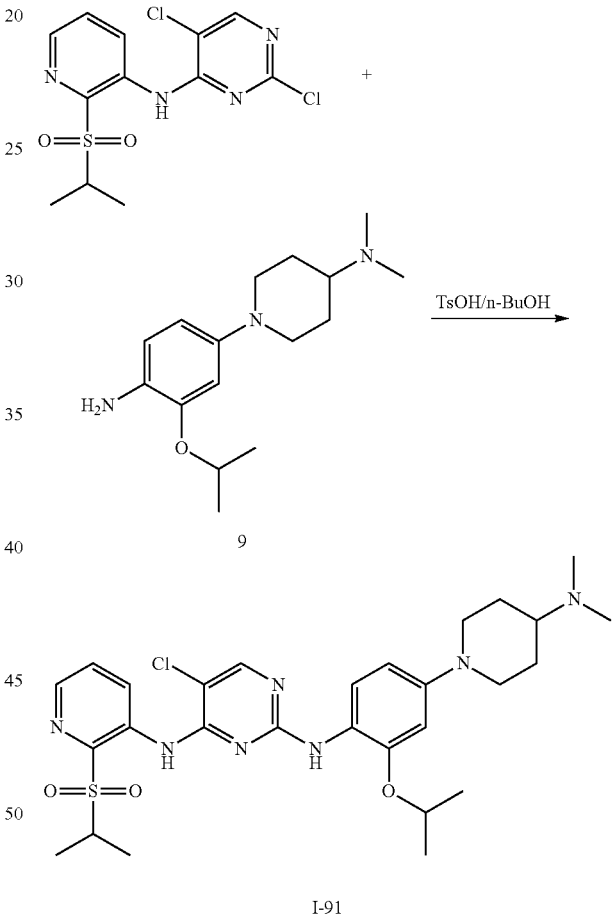

To n-butanol (1.5 mL) was added 2,5-dichloro-N-(2-(isopropylsulfonyl) pyridin-3-yl) pyrimidine-4-amine (150 mg, 0.43 mmol) and 1-(4-amino-3-isopropoxyphenyl)-N,N-dimethylpiperidine-4-amine (compound 9) (120 mg, 0.43 mmol), and then added with p-toluenesulfonic acid (74 mg, 0.43 mmol). The mixture was heated to 115° C. and stirred for 5 hours. After TLC indicated the reaction was completed, the reaction mixture was cooled to room temperature, evaporated under decreased pressure to remove solvent, and dissolved with dichlorohexane. The resulting crude product was washed with saturated sodium bicarbonate and saturated aqueous sodium chloride, dried over anhydrous sodium sulfate, filtered and concentrated to give a product which was further isolated and purified by column chromatography to obtain a light green solid product, compound I-91 (100 mg, yield 39.4%).

$^1$H NMR (400 MHz, CDCl$_3$): δ 10.04 (s, 1H), 9.17 (d, J=8.8 Hz, 1H), 8.38 (d, J=4.4 Hz, 1H), 8.15 (s, 1H), 7.96 (d, J=8.8 Hz, 1H), 7.45 (dd, J=8.8, 4.4 Hz, 1H), 7.31 (s, 1H), 6.53 (s, 1H), 6.46 (d, J=9.2 Hz, 1H), 4.75-4.44 (m, 2H), 3.69 (d, J=12.0 Hz, 3H), 3.15 (s, 2H), 2.78 (s, 6H), 2.26 (d, J-=9.6 Hz, 2H), 2.00-1.86 (m, 2H), 1.37 (t, J=5.6 Hz, 12H).

LCMS: t=3.39 min, 588.2 (M+H$^+$), 294.7 (M/2+H$^+$).

During preparation of the compound I-91, said 1-(4-amino-3-isopropoxyphenyl)-N,N-dimethylpiperidine-4-amine (compound 9) was synthesized by a route below

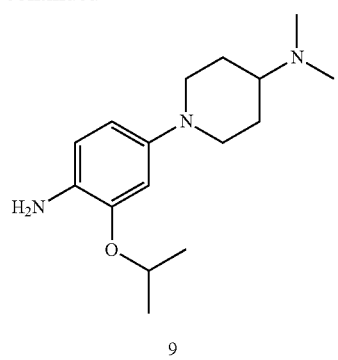

9

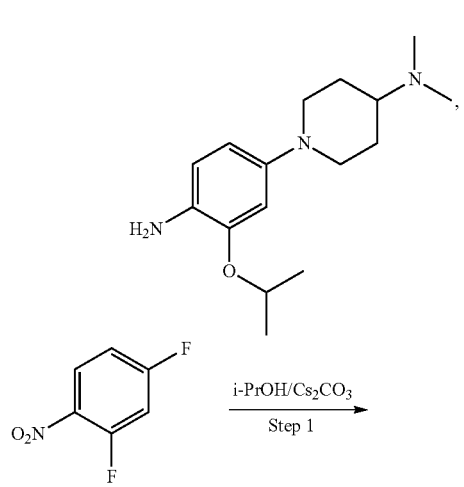

Step 1 Preparation of 2-isopropoxy-4-fluoro-1-nitrobenzene

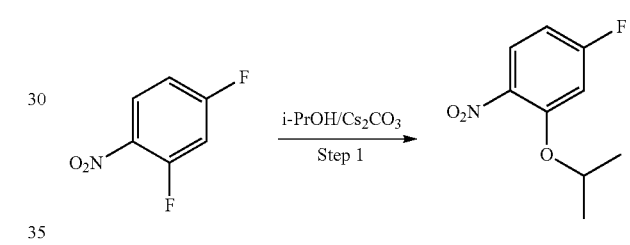

To isopropanol (60 mL) was added compound 2,4-difluoro-1-nitrobenzene (5.0 g, 31.43 mmol) and cesium carbonate (30.64 g, 94.29 mmol). The mixture was heated to 80° C. and stirred overnight. After TLC indicated the reaction was completed, the mixture was diluted with water and extracted with DCM. The combined organic phase was dried over anhydrous sodium sulfate, filtered and evaporated to remove solvent, thus obtaining a crude product which was further isolated and purified by column chromatography to give a white solid (5.2 g, yield 83%).

Step 2 Preparation of 1-(3-isopropoxy-4-nitrophenyl)-N,N-dimethylpiperidine-4-amine

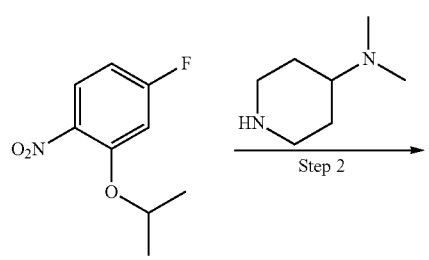

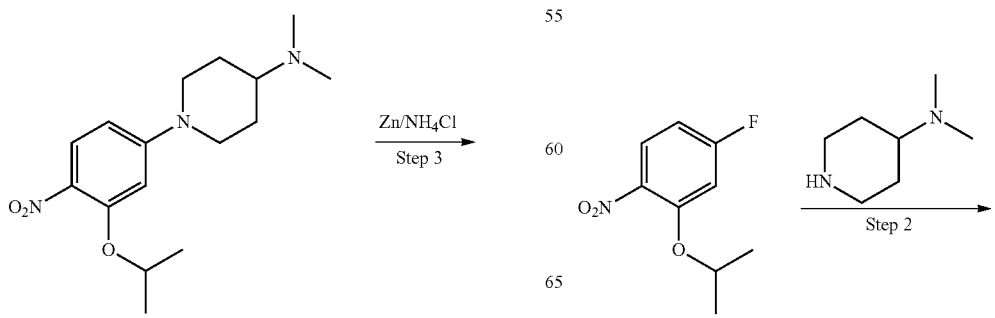

-continued

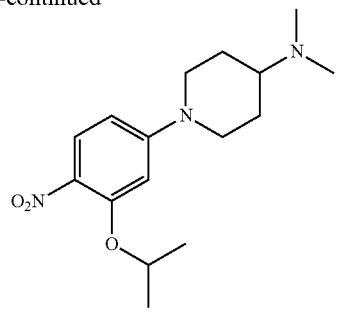

To DMF (60 mL) was added compound 4-fluoro-2-isopropoxy-1-nitrobenzene (5 g, 25.1 mmol), and then N,N-dimethylpiperidine-4-amine hydrochloride (3.54 g, 27.61 mmol) and potassium carbonate (10.41 g, 75.31 mmol). The mixture was heated to 82° C. and stirred overnight. After TLC indicated the reaction was completed, the mixture was cooled to room temperature, diluted with water and extracted with ethyl acetate. The organic phase was washed with saturated aqueous sodium chloride, dried over anhydrous sodium sulfate, filtered and concentrated to give a white product (6.2 g, yield 80%).

LCMS: t=2.476 min, 308.1 (M+H$^+$).

Step 3 Preparation of 1-(4-amino-3-isopropoxy phenyl)-N,N-dimethylpiperidine-4-amine

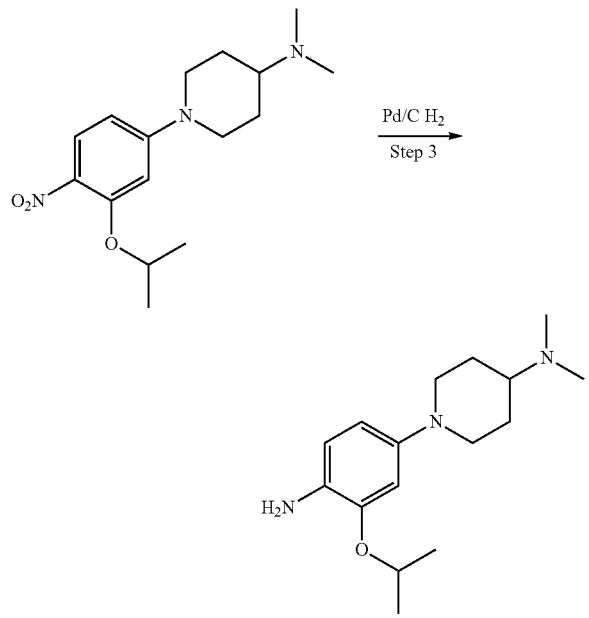

To 15 mL methanol was added compound 1-(3-isopropoxy-4-nitrophenyl)-N,N-dimethylpiperidine-4-amine (1.7 g, 5.53 mmol) and palladium on carbon (580 mg). After gas replacement with hydrogen, the mixture was stirred under hydrogen atmosphere at room temperature overnight. After TLC indicated the reaction was completed, the mixture was filtrated and evaporated to remove methanol, thus obtaining a black oily product (1.45 g, yield 90%).

LCMS: t=0.43 min, 278.1 (M+H$^+$).

Example 21 Preparation of 5-chloro-N$^2$-(4-(4-(dimethylamino) piperidin-1-yl)-2-ethoxyphenyl-N$^4$-(2-(isopropylsulfonyl) pyridin-3-yl) pyrimidine-2,4-diamine (Compound I-92)

Preparation Scheme

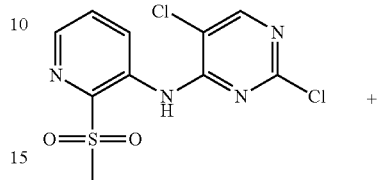

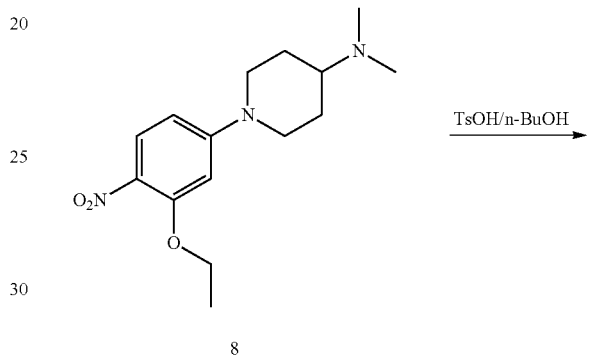

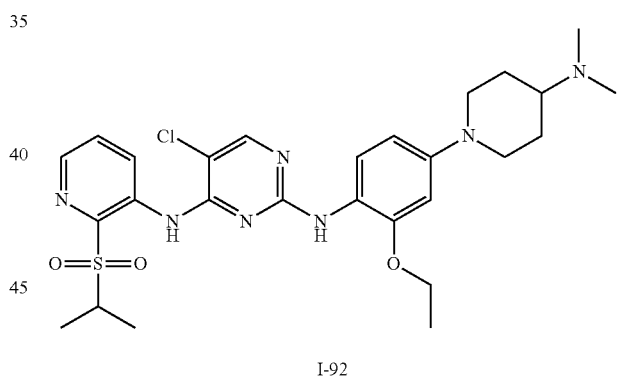

I-92

To n-butanol (1.5 mL) was added 2,5-dichloro-N-(2-(isopropylsulfonyl) pyridin-3-yl) pyrimidine-4-amine (150 mg, 0.43 mmol) and 1-(4-amino-3-ethoxy phenyl)-N,N-dimethylpiperidine-4-amine (compound 8) (114 mg, 0.43 mmol), and then p-toluenesulfonic acid (74 mg, 0.43 mmol). The mixture was heated to 115° C. and stirred for 5 hours. After TLC indicated the reaction was completed, the reaction mixture was cooled to room temperature, evaporated under decreased pressure to remove solvent, and then dissolved in dichlorohexane. The resulting crude product was washed with saturated sodium bicarbonate and saturated aqueous sodium chloride, dried over anhydrous sodium sulfate, filtered and concentrated to give a product which was further isolated and purified by column chromatography to obtain a light green solid product, compound I-92 (90 mg, yield 36.3%).

¹H NMR (400 MHz, cd₃od) δ 9.08 (d, J=8.4 Hz, 1H), 8.34 (d, J=4.1 Hz, 1H), 8.10 (s, 1H), 7.69 (d, J=8.1 Hz, 1H), 7.49 (dd. J=8.6, 4.3 Hz, 1H), 7.22 (d, J=8.0 Hz, 1H), 6.66 (d, J=2.2 Hz, 1H), 4.05 (dd, J=13.9, 6.9 Hz, 2H), 3.81 (dd, J=13.5, 6.8 Hz, 2H), 3.22 (m, 1H), 2.84 (s, 6H), 2.78 (m, 2H), 2.17 (m, 2H), 1.83 (m, 2H), 1.38-1.27 (m, 6H).

LCMS: t=3.37 min, 574.1 (M+H⁺).

During preparation of the compound I-92, said 1-(4-amino-3-ethoxy phenyl)-N,N-dimethylpiperidine-4-amine (compound 8) was synthesized by a route below:

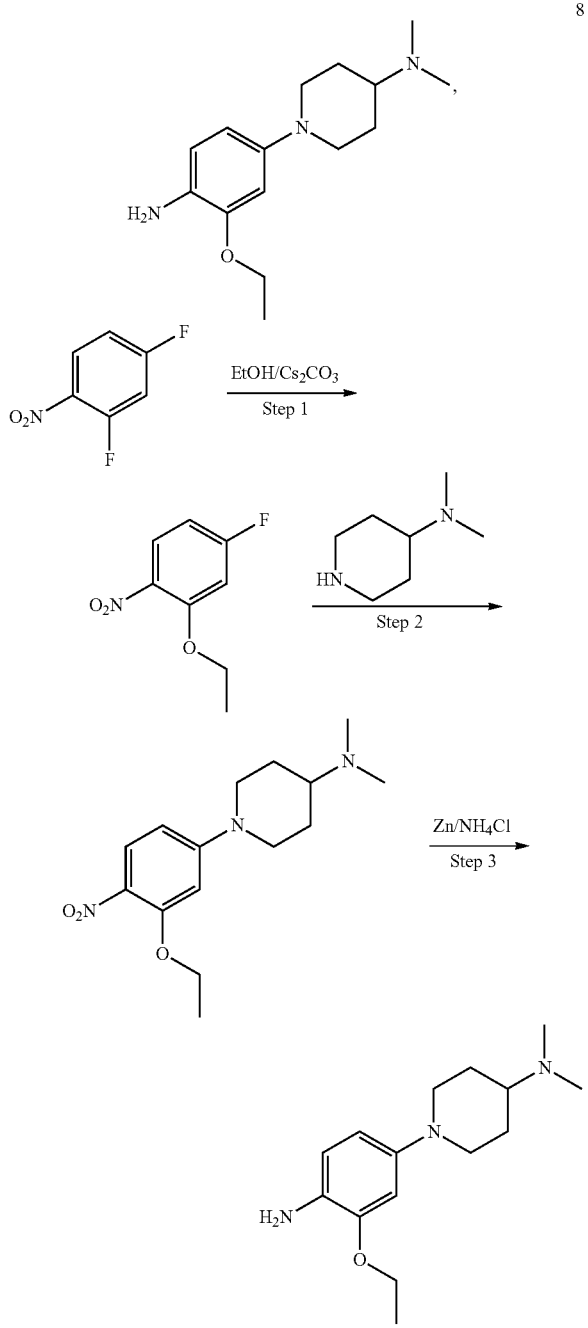

Step 1 Preparation of 2-ethyoxy-4-fluoro-1-nitrobenzene

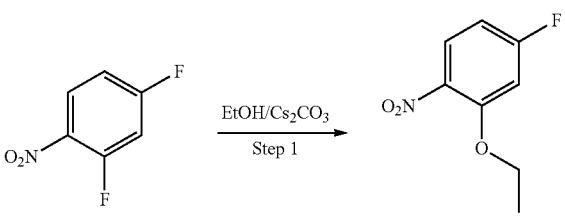

To ethanol (70 mL) was added compound 2,4-difluoro-1-nitrobenzene (5.0 g, 31.44 mmol), and cesium carbonate (30.66 g, 94.34 mmol). The mixture was heated and stirred overnight. After TLC indicated the reaction was completed, the mixture was evaporated to dryness, diluted with water, and extracted with ethyl acetate. The combined organic phase was dried over anhydrous sodium sulfate, filtered and evaporated to remove solvent, thus obtaining a crude product. The crude product was further isolated and purified by column chromatography to obtain a white solid (5.5 g, yield 95%).

Step 2 Preparation of 1-(3-ethyoxy-4-nitrophenyl)-N,N-dimethylpiperidine-4-amine

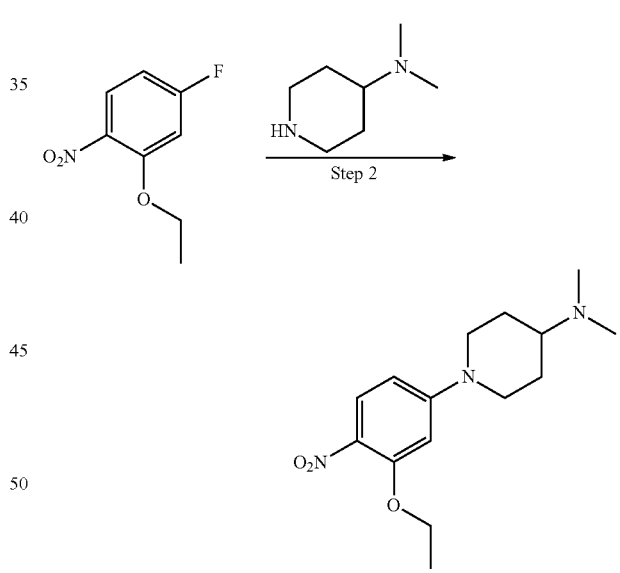

To DMF (60 mL) was added compound 4-fluoro-2-ethyoxy-1-nitrobenzene (5 g, 27 mmol), N,N-dimethylpiperidine-4-amine hydrochloride (3.81 g, 29.7 mmol) and potassium carbonate (11.2 g, 781.01 mmol). The mixture was heated to 82° C. and stirred overnight. After TLC indicated the reaction was completed, the mixture was diluted with water, and extracted with ethyl acetate twice. The combined organic phase was washed with saturated aqueous sodium chloride, dried over anhydrous sodium sulfate, filtered and evaporated to remove solvent, thus obtaining a white product (6.2 g, yield 78%).

LCMS: t=2.602 min, 294.1 (M+H⁺).

Step 3 Preparation of 1-(4-amino-3-ethoxy phenyl)-N,N-dimethylpiperidine-4-amine

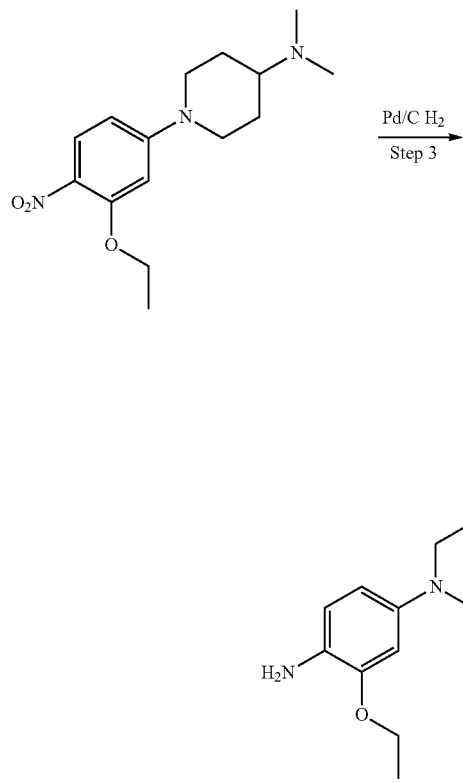

To 15 mL methanol was added compound 1-(3-ethyoxy-4-nitrobenzene)-N,N-dimethylpiperidine-4-amine (2.22 g, 7.57 mmol) and palladium on carbon (300 mg). After gas replacement with hydrogen three times, the mixture was stirred under hydrogen atmosphere at room temperature overnight. After TLC indicated the reaction was completed, the mixture was filtrated to remove the palladium on carbon, and concentrated under decreased pressure to give a black oily product (1.54 g, yield 75%).

LCMS: t=0.430 min, 264.1 (M+H$^+$).

Example 22 Preparation of 5-chloro-N$^2$-(2-isopropoxy-5-methyl-4-(1,2,3,6-tetrahydropiperidin-4-yl) phenyl)-N$^4$-(2-isopropylsulfonyl) pyridin-3-yl) pyrimidine-2,4-diamine (Formula I-90)

Preparation Scheme

Step 1 Preparation of 4-(4-((5-chloro-4-((2-(isopropylsulfonyl) pyridin-3-yl) amino) pyrimidin-2-yl) amino)-5-isopropoxy-2-methylphenyl)-3,6-dihydropiperidine-1 (2H)-tert-butyl carboxylate To a 10 mL microwave tube was added 2,5-dichloro-N-(2-isopropylsulfonyl) pyridin-3-yl) pyrimidine-4-amine (0.37 g, 1.07 mmol), 4-(4-amino-5-isopropoxy-2-methylphenyl)-3,6-dihydropiperidine-1 (2H)-tert-butyl carboxylate (0.41 g, 1.17 mmol), cesium carbonate (1.04 g, 3.20 mmol), Pd$_2$(dba)$_3$ (49.0 mg, 0.053 mmol) and Xantphos (62.0 mg, 0.107 mmol), and then added with 3 mL 1,4-dioxane. After gas replacement with nitrogen three times, the mixture was heated to 130° C. and reacted via microwave for 40 minutes. After TLC indicated the reaction was completed, the reaction mixture was cooled to room temperature, diluted with water, and extracted with ethyl acetate twice. The obtained organic phase was washed with saturated aqueous sodium chloride, dried over anhydrous sodium sulfate, filtered and concentrated to give a crude product which was further isolated and purified by column chromatography (PE:EtOAc=3:1) to obtain a white solid (260 mg, yield 37%).

LCMS: t=7.97 min, 657.2 (M+H$^+$).

Step 2 Preparation of 5-chloro-N$^2$-(2-isopropoxy-5-methyl-4-(1,2,3,6-tetrahydropiperidin-4-yl) phenyl)-N$^4$-(2-(isopropoxysulfonyl) pyridin-3-yl) pyrimidine-2,4-diamine To hydrochloric acid/ethyl acetate (4 M) was added 4-(4-((5-chloro-4-((2-isopropylsulfonyl) pyridin-3-yl)

amino) pyrimidin-2-yl) amino)-5-isopropoxy-2-methylphenyl)-3,6-dihydropiperidine-1 (2H)-tert-butyl carboxylate (260 mg, 0.396 mmol), and the mixture was stilled overnight. After TLC indicated the reaction was completed, the mixture was concentrated under reduced pressure to give a crude product, which was further slurried with ethyl acetate to obtain a light yellow solid product, formula I-90 (100 mg, yield 43%).

$^1$H NMR (400 MHz, CDCl$_3$): δ 10.77 (s, 2H), 10.09 (s, 1H), 9.56 (s, 1H), 8.98 (s, 1H), 8.48 (s, 1H), 8.15 (s, 1H), 7.58 (s, 1H), 7.41 (s, 1H), 6.73 (s, 1H), 5.65 (s, 1H), 4.58 (s, 1H), 4.11-3.78 (m, 3H), 3.50 (s, 2H), 2.75 (s, 2H), 2.19 (s, 3H), 1.52-1.25 (m, 12H).

LCMS: t=3.44 min, 557.1 (M+H$^+$).

During preparation of the compound I-90, said 4-(4-amino-5-isopropoxy-2-methylphenyl)-3,6-dihydropiperidine-1 (2H)-tert-butyl carboxylate (compound 6) was synthesized by a route below

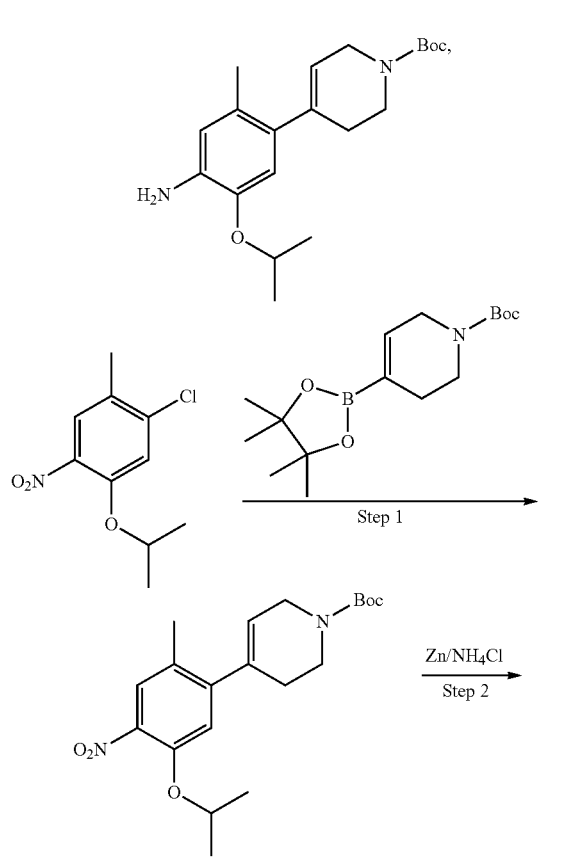

Step 1 Preparation of 4-(5-isopropoxy-2-methyl-4-nitrobenzene)-3,6-dihydropiperidine-1 (2H)-tert-butyl carboxylate

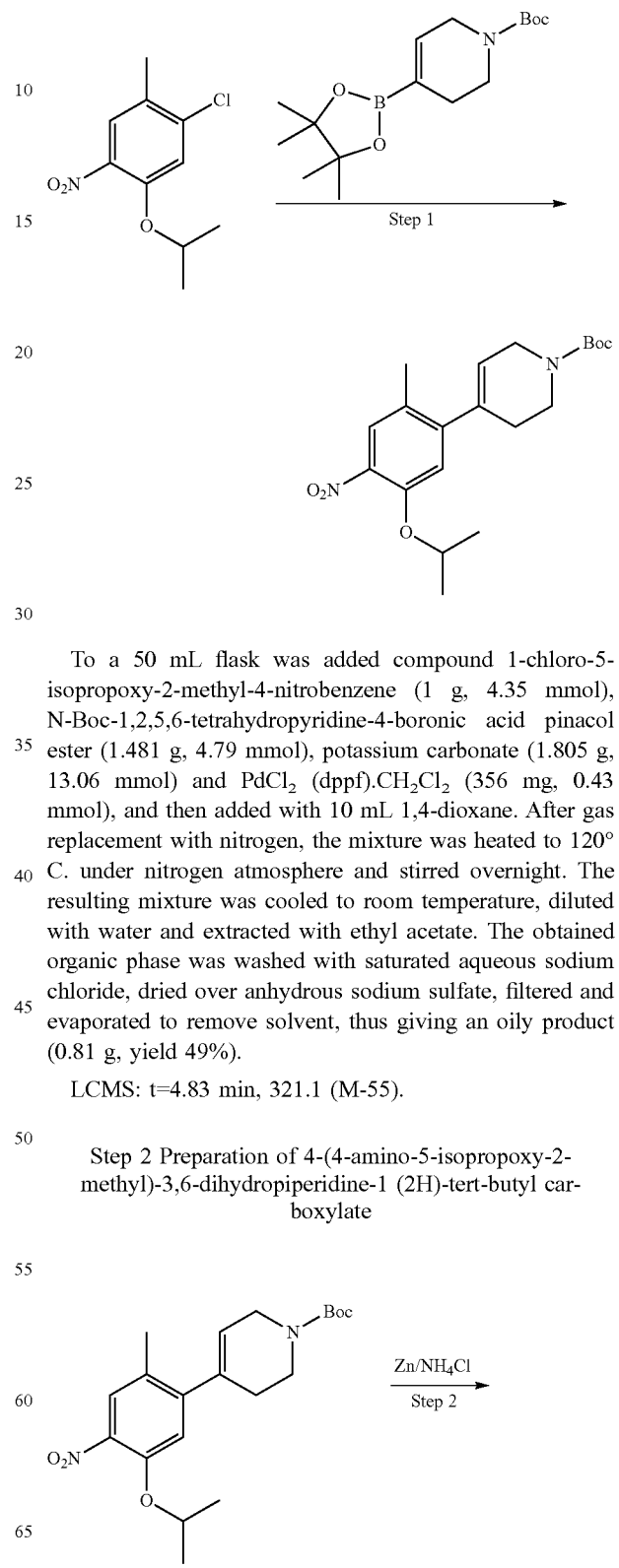

To a 50 mL flask was added compound 1-chloro-5-isopropoxy-2-methyl-4-nitrobenzene (1 g, 4.35 mmol), N-Boc-1,2,5,6-tetrahydropyridine-4-boronic acid pinacol ester (1.481 g, 4.79 mmol), potassium carbonate (1.805 g, 13.06 mmol) and PdCl$_2$ (dppf).CH$_2$Cl$_2$ (356 mg, 0.43 mmol), and then added with 10 mL 1,4-dioxane. After gas replacement with nitrogen, the mixture was heated to 120° C. under nitrogen atmosphere and stirred overnight. The resulting mixture was cooled to room temperature, diluted with water and extracted with ethyl acetate. The obtained organic phase was washed with saturated aqueous sodium chloride, dried over anhydrous sodium sulfate, filtered and evaporated to remove solvent, thus giving an oily product (0.81 g, yield 49%).

LCMS: t=4.83 min, 321.1 (M-55).

Step 2 Preparation of 4-(4-amino-5-isopropoxy-2-methyl)-3,6-dihydropiperidine-1 (2H)-tert-butyl carboxylate

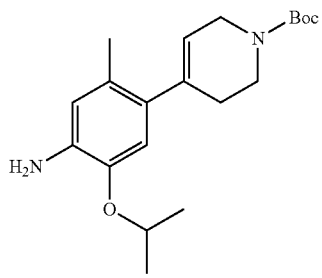

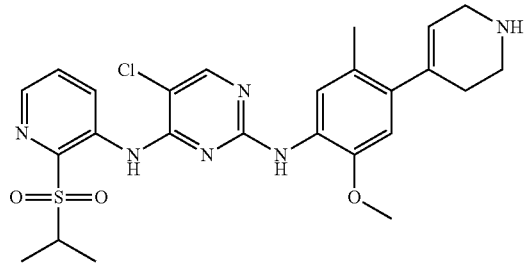

I-89

To 15 mL methanol was added compound 4-(5-isopropoxy-2-methyl-4-nitrophenyl)-3,6-dihydropiperidine-1 (2-hydrogen)-tert-butyl carboxylate (0.81 g, 2.152 mmol) and ammonium chloride (1.151 g, 21.52 mmol). Zinc powder (1.40 g, 21.538 mmol) was added in portions under room temperature. The mixture was refluxed under heating, stirred overnight and cooled to room temperature. The resulting mixture was filtered, evaporated rotarily to dryness, dissolved with dichloromethane and washed with saturated sodium bicarbonate. The obtained crude was further dried over anhydrous sodium sulfate, filtered and concentrated to give a solid (0.26 g, yield 97%).

LCMS: t=3.97 min, 347.1 (M+H$^+$).

Example 23 Preparation of 5-chloro-N$^4$-(2-isopropylsulfonyl) pyridin-3-yl)-N$^2$-(2-methoxy-5-methyl-4-(1,2,3,6-tetrahydropiperidin-4-yl) phenyl) pyrimidine-2,4-diamine (Compound I-89)

Preparation Scheme

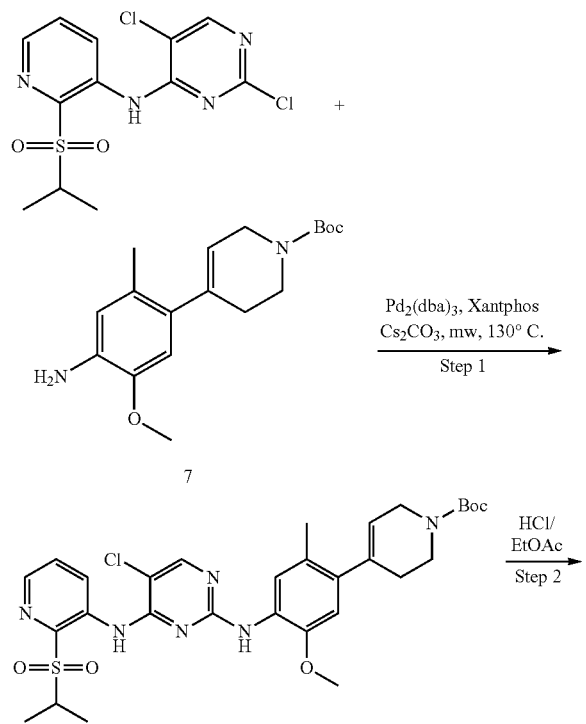

Step 1 Preparation of 4-(4-((5-chloro-4-((2-(isopropylsulfonyl) pyridin-3-yl) amino) pyrimidin-2-yl) amino)-5-methoxy-2-methylphenyl)-3,6-dihydropiperidine-1 (2H)-tert-butyl carboxylate To a 10 mL microwave tube was added compound 4-(4-amino-5-methoxy-2-methylphenyl)-3,6-dihydropiperidine-1 (2H)-tert-butyl carboxylate (0.726 g, 2.281 mmol), 2,5-dichloro-N-(2-(isopropylsulfonyl) pyridin-3-yl) pyrimidine-4-amine (0.72 g, 2.074 mmol), cesium carbonate (2.027 g, 6.22 mmol), Pd$_2$(dba)$_3$ (0.095 g, 0.104 mmol) and Xantphos (0.120 g, 0.207 mmol), and then added with 10 mL 1,4-dioxane. After gas replacement with nitrogen, the mixture was heated via microwave for 40 minutes, and then cooled to room temperature. The mixture was diluted with EtOAc, washed with saturated aqueous sodium chloride, dried over anhydrous sodium sulfate, filtered and concentrated to give a crude product which was further isolated and purified by column chromatography to obtain a white solid (200 mg, yield 14%).

Step 2 Preparation of 5-chloro-N$^4$-(2-(isopropylsulfonyl) pyridin-3-yl)-N$^2$-(2-methoxy-5-methyl-4-(1,2,3,6-tetrahydropiperidin-4-yl) phenyl) pyrimidine-2,4-diamine To 1 mL EtOAc was added compound 4-(4-((5-chloro-4-((2-(isopropylsulfonyl) pyridin-3-yl) amino) pyrimidin-2-yl) amino)-5-methoxy-2-methylphenyl)-3,6-dihydropiperidine-1 (2H)-tert-butyl carboxylate (0.2 g, 0.318 mmol), and 4 mL HCl/EtOAc (4M) was added slowly at room temperature. The mixture was stirred overnight, and then concentrated, slurried with ethyl acetate, and isolated by HPLC preparative chromatography to give a light yellow solid product, compound I-89 (100 mg, yield 51.6%).

$^1$H NMR (400 MHz, cd$_3$od) δ 9.11 (d, J=8.5 Hz, 1H), 8.38 (d, J=4.3 Hz, 1H), 8.16 (s, 1H), 7.75 (s, 1H), 7.58 (dd, J=8.7, 4.4 Hz, 1H), 6.75 (s, 1H), 5.65 (s, 1H), 3.90-3.77 (m, 6H), 3.46 (t, J=6.0 Hz, 2H), 2.63 (d, J=1.8 Hz, 2H), 2.18 (s, 3H), 1.31 (d, J=6.9 Hz, 6H).

LCMS: t=3.29 min, 531.1 (M+H$^+$), 265.2 (M/2+H$^+$).

During preparation of the compound I-89, said 4-(4-amino-5-methoxy-2-methylphenyl)-3,6-dihydropiperidine-1 (2H)-tert-butyl carboxylate (compound 7) was synthesized by a route below

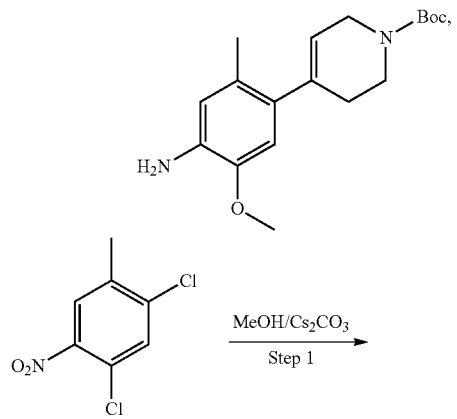

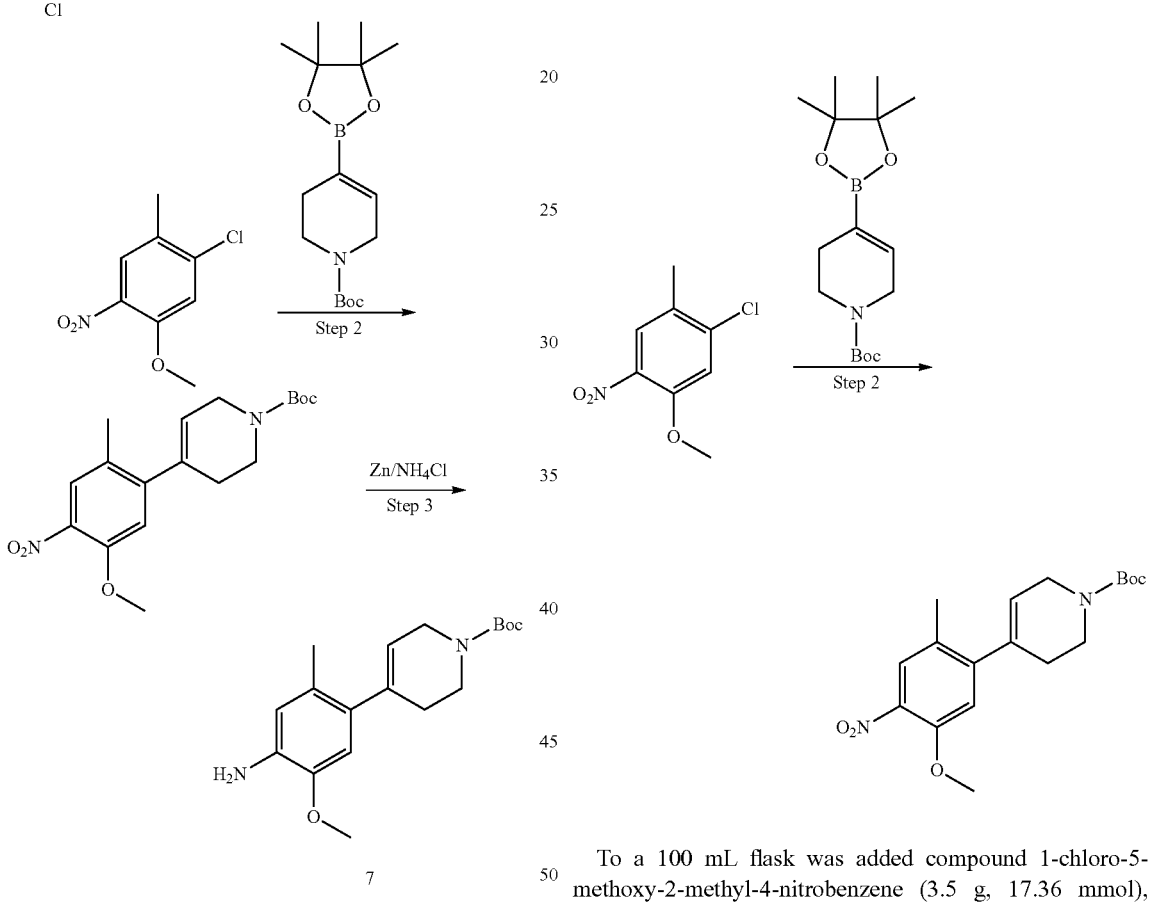

Step 1 Preparation of 1-chloro-5-methoxy-2-methyl-4-nitrobenzene

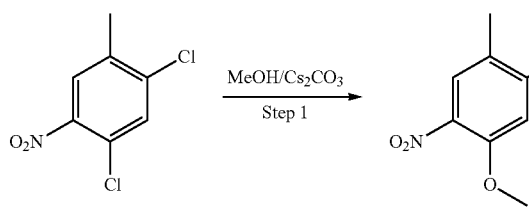

To methanol (20 mL) was added compound 1,5-dichloro-2-methyl nitrobenzene (2 g, 9.71 mmol) and cesium carbonate (9.49 g, 29.12 mmol), and the mixture was reacted for 3 hours at room temperature. After TLC indicated the reaction was completed, the mixture was diluted with water (80 mL), and extracted with DCM (100 mL×2). The combined organic phase was washed with saturated aqueous sodium chloride (50 mL), dried over anhydrous sodium sulfate, filtered and evaporated to remove solvent, thus obtaining a white product (1.76 g, yield 90%).

Step 2 Preparation of 4-(5-methoxy-2-methyl-4-nitrophenyl)-3,6-dihydropiperidine-1 (2H)-tert-butyl carboxylate To a 100 mL flask was added compound 1-chloro-5-methoxy-2-methyl-4-nitrobenzene (3.5 g, 17.36 mmol), N-Boc-1,2,5,6-tetrahydropyridine-4-boronic acid pinacol ester (5.90 g, 19.10 mmol), potassium carbonate (7.20 g, 52.1 mmol) and Pd(Ph$_3$P)$_4$ (1.003 g, 0.868 mmol), and then added with 20 mL 1,4-dioxane. After gas replacement with nitrogen, the mixture was heated under nitrogen atmosphere to 120° C. and stirred overnight. After TLC indicated the reaction was completed, the mixture was evaporated rotarily to remove solvent, diluted with water, and extracted with EtOAc. The obtained organic phase was washed with saturated aqueous sodium chloride, dried over anhydrous sodium sulfate, filtered and evaporated to dryness to give a crude product which was further isolated by column chromatography to give a white solid product (3 g, yield 49%).

LCMS: t=4.507 min, 293.0 (M-55).

Step 3 Preparation of 4-(4-amino-5-methoxy-2-methylphenyl)-3,6-dihydropiperidine-1 (2H)-tert-butyl carboxylate

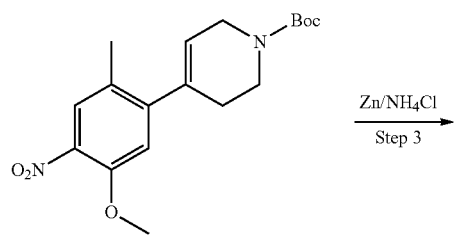

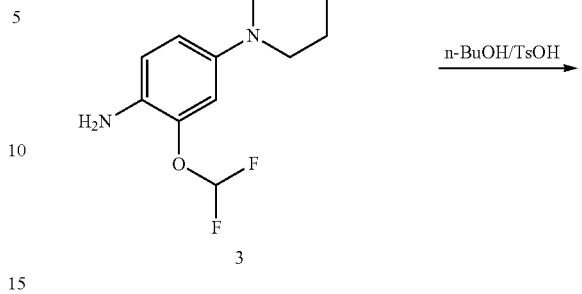

To 10 mL methanol was added compound 4-(5-methoxy-2-methyl-4-nitrophenyl)-3,6-dihydropiperidine-1 (2H)-tert-butyl carboxylate (0.8 g, 2.296 mmol) and ammonium chloride (0.614 g, 11.48 mmol) at room temperature, and then zinc powder (0.751 g, 11.48 mmol) was added in portions. The mixture was reluxed under heating for 2 hours. After TLC indicated the reaction was completed, the mixture was cooled to room temperature, evaporated to dryness, dissolved with EtOAc and washed with sodium bicarbonate. The resulting crude product was dried over anhydrous sodium sulfate, filtered and evaporated to dryness, thus obtaining a white solid product (0.72 g. yield 98.6%).

LCMS: t=3.489 min, 319.1 (M+H$^+$).

Example 24 Preparation of 5-chloro-N$^2$-(2-(difluoromethoxy)-4-(4-(dimethylamino) piperidin-1-yl) phenyl)-N$^4$-(2-(isopropylsulfonyl) pyridin-3-yl) pyrimidine-2,4-diamine (Compound I-100)

Preparation Scheme

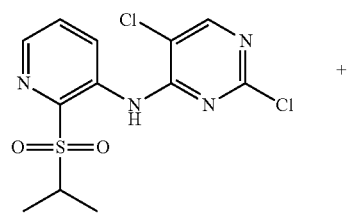 +

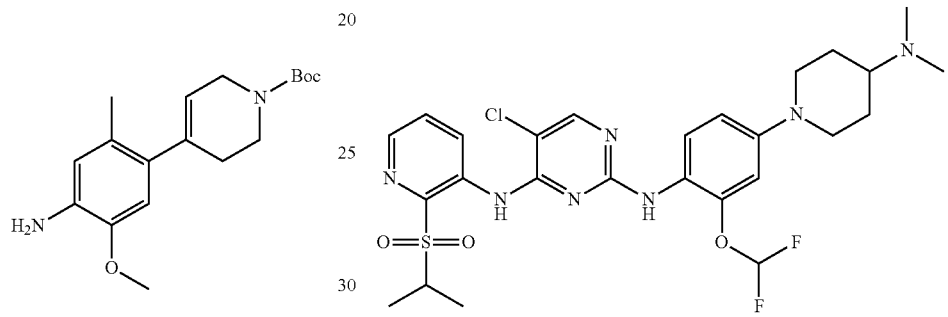

I-100

To n-butanol (1.5 mL) was added 2,5-dichloro-N-(2-(isopropylsulfonyl) pyridin-3-yl) pyrimidine-4-amine (150 mg, 0.432 mmol) and 1-(4-amino-3-(difluoromethoxy) phenyl)-N,N-dimethylpiperidine-4-amine (compound 3) (123 mg, 0.432 mmol), and then added with p-toluenesulfonic acid (74 mg, 0.432 mmol). The mixture was heated to 115° C. and stirred for 5 hours. After TLC indicated the reaction was completed, the mixture was cooled to room temperature, evaporated under decreased pressure to remove solvent, dissolved with dichlorohexane and washed with saturated sodium bicarbonate and saturated aqueous sodium chloride. The resulting crude product was dried over anhydrous sodium sulfate, filtered and concentrated, isolated and purified by column chromatography to give a brownish red solid product, compound I-100 (110 mg, yield 43%).

$^1$H NMR (400 MHz, CDCl$_3$): δ 10.11 (s, 1H), 9.11 (d, J=8.8 Hz, 1H), 8.37 (dd, J=4.4, 1.3 Hz, 1H), 8.15 (s, 1H), 7.86 (d, J=8.8 Hz, 1H), 7.41 (dd, J=8.8, 4.4 Hz, 1H), 6.95 (s, 1H), 6.78 (dd. J=8.8, 2.6 Hz, 1H), 6.75 (s, 1H), 6.50 (t, J=73.6 Hz, 1H), 3.90 (dq, J=13.6, 7.2 Hz, 1H), 3.67 (t, J=12.4 Hz, 2H), 2.75 (dd, J=1.8, 12.2 Hz, 2H), 2.42 (s, 6H), 2.03 (d, J=12.8 Hz, 2H), 1.76-1.66 (m, 2H), 1.38 (d, J=6.8 Hz, 6H).

LCMS: t=3.50 min, 596.2 (M+H$^+$).

During preparation of the compound I-100, said 1-(4-amino-3-(difluoromethoxy) phenyl)-N,N-dimethylpiperidine-4-amine (compound 3) was synthesized by a route below

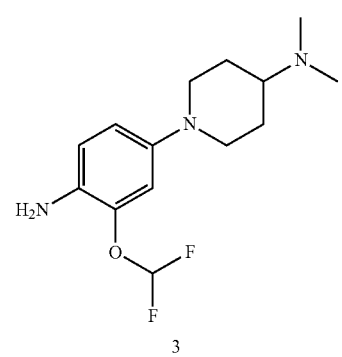

3

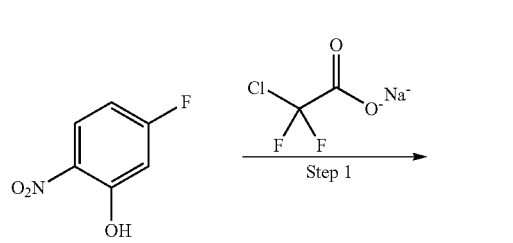

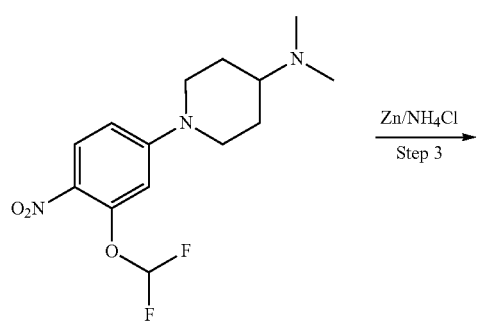

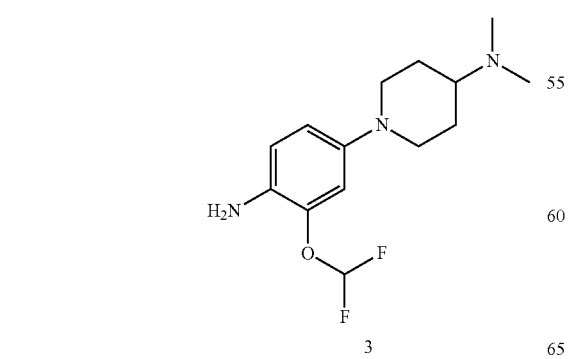

3

Step 1 Preparation of
4-chloro-2-difluoromethoxy)-1-nitrobenzene

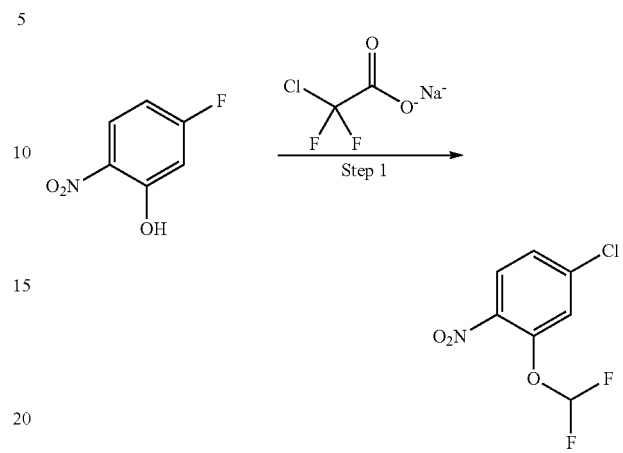

Compound 2-fluorine-2-nitrophenol (4 g, 25.5 mmol) was dissolved in DMF (50 mL)/H$_2$O (10 mL), and then added with 2-chloro-2,2-sodium difluoroacetate (11.65 g, 46 mmol) and potassium carbonate (10.56 g, 76 mmol). After gas replacement with nitrogen, the mixture was heated under nitrogen atmosphere to 100° C. and stirred for 5 hours. After TLC indicated the reaction was completed, the reaction mixture was cooled to room temperature, diluted with water, and extracted with ethyl acetate. The obtained organic phase was washed with saturated aqueous sodium chloride, dried over anhydrous sodium sulfate, filtered and evaporated to dryness, and further isolated by column chromatography (petroleum ether) to a yellow oily product (2.5 g, yield 47%).

Step 2 Preparation of 1-(3-(difluoromethoxy)-4-nitrophenyl)-N,N-dimethylpiperidine-4-amine

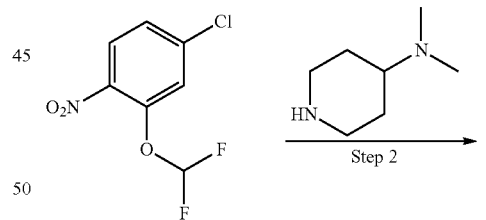

Compound 2-(difluoromethoxy)-4-chloro-1-nitrobenzene (2.5 g, 12.07 mmol) was dissolved in DMF (20 mL), and N,N-dimethylpiperidine-4-amine hydrochloride (2.428 g, 12.07 mmol) and potassium carbonate (5.00 g, 36.2 mmol) was added under stirring. The mixture was heated to 80° C. and stirred overnight. After TLC indicated the reaction was completed, the reaction mixture was cooled to room temperature, diluted with water, and extracted with ethyl acetate. The obtained organic phase was washed with saturated aqueous sodium chloride, dried over anhydrous sodium sulfate, filtered and concentrated, and further isolated by column chromatography (DCM:MeOH=30:1) to a yellow oily product (1.4 g, yield 34%).

LCMS: t=2.68 min, 316.0 (M+H+).

Step 3 Preparation of 1-(4-amino-3-(difluoromethoxy) phenyl)-N,N-dimethylpiperidine-4-amine

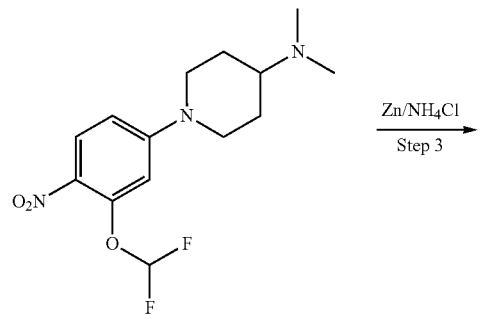

To methanol (10 mL) was added compound 1-(3-(difluoromethoxy)-4-nitrophenyl)-N,N-dimethylpiperidine-4-amine (0.7 g, 2.220 mmol), and ammonium chloride (1.188 g, 22.20 mmol) was added under stirring. Zinc powder (1.451 g, 22.20 mmol) was added in portions, and the mixture was refluxed under heating for 3 hours. After TLC indicated the reaction was completed, the reaction mixture was cooled to room temperature, filtered and concentrated. The resulting crude product was dissolved with DCM, washed with sodium bicarbonate, dried over anhydrous sodium sulfate, filtered and concentrated to give a brown oily product (0.5 g, yield 77%), i.e., the intermediate 3 of the present example.

LCMS: t=0.48 min, 286.1 (M+H+).

Example 25 Preparation of 5-chloro-N2-(4-(1-isopropyl-1,2,3,6-tetrahydropyridin-4-yl)-2-methoxy-5-methylphenyl)-N4-(2-(isopropylsulfonyl) pyridin-3-yl) pyrimidine-2,4-diamine (Compound I-80)

Preparation Scheme

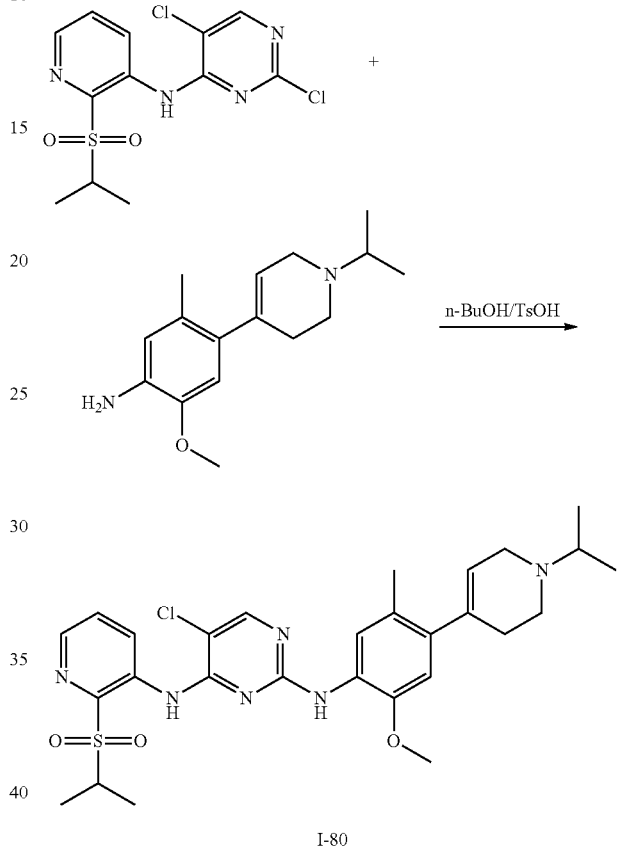

I-80

To n-BuOH (2.5 mL) was added 2,5-dichloro-N-(2-(isopropylsulfonyl) pyridin-3-yl) pyrimidine-4-amine (183 mg, 0.527 mmol) and 4-(1-isopropyl-1,2,3,6-tetrahydropyridin-4-yl)-2-methoxy-5-methylaniline (137 mg, 0.527 mmol), and then added with p-toluenesulfonic acid (91 mg, 0.527 mmol). The mixture was heated to 120° C. and stirred for 3 hours. After LCMS indicated the reaction was completed, the reaction mixture was cooled to room temperature, diluted with ethyl acetate (25 mL) and washed with water and saturated aqueous sodium chloride. The obtained crude product was dried over anhydrous sodium sulfate, filtered and concentrated, and further isolated by column chromatography (DCM/MeOH (v/v=40:1 to 20:1)) to obtain a yellow solid product, compound I-80 (186 mg, yield 61.8%).

1H NMR (400 MHz, CDCl3): δ 10.08 (s, 1H), 9.18 (d, J=8.3 Hz, 1H), 8.37 (d, J=3.4 Hz, 1H), 8.18 (s, 1H), 7.96 (s, 1H), 7.53-7.42 (m, 2H), 6.76 (s, 1H), 5.59 (s, 1H), 3.99-3.86 (m, 2H), 3.83 (s, 3H), 3.74-3.69 (m 3H), 3.34 (s, 3H), 2.17 (s, 3H), 1.47 (d, J=6.6 Hz, 6H), 1.38 (d, J=6.9 Hz, 6H).

LCMS: t=3.42 min, 571.1 (M+H+).

Example 26 Preparation of 5-chloro-$N^2$-(4-(4-(dimethylamino) piperidin-1-yl)-2-isopropoxy phenyl)-$N^4$-(2-(isopropylsulfonyl) thiophen-3-yl) pyrimidine-2,4-diamine (Compound I-82)

Preparation Scheme

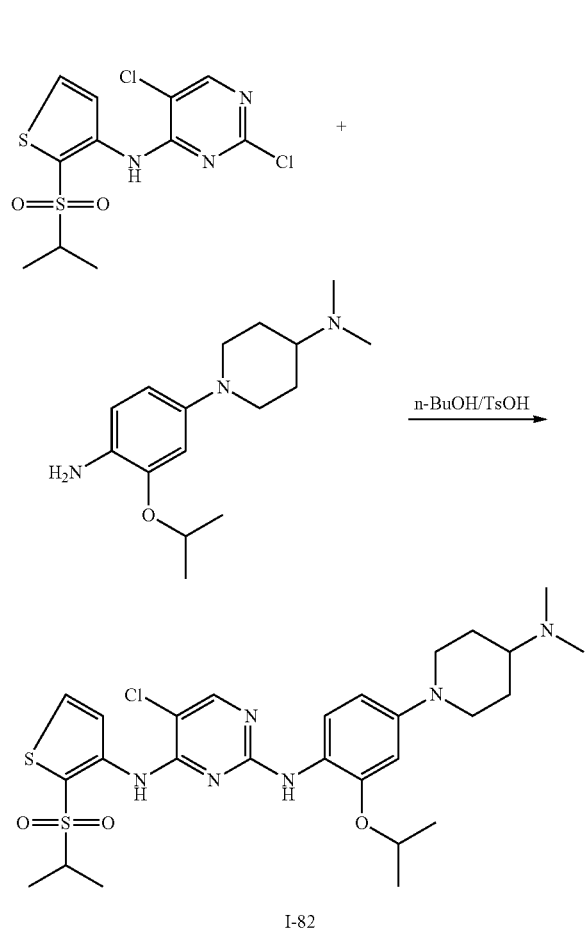

I-82

To n-BuOH (2.5 mL) was added 2,5-dichloro-N-(2-(isopropylsulfonyl) thiophen-3-yl) pyrimidine-4-amine (186 mg, 0.528 mmol) and intermediate 9 (147 mg, 0.530 mmol), and then added with p-toluenesulfonic acid (91 mg, 0.528 mmol). The mixture was heated to 120° C. and stirred for 3 hours. After LCMS indicated the reaction was completed, the reaction mixture was cooled to room temperature, then diluted with ethyl acetate (25 mL), washed with water and saturated aqueous sodium chloride. The obtained crude product was dried over anhydrous sodium sulfate, filtered and concentrated, and further isolated by column chromatography (DCM/MeOH (v/v=40:1 to 20:1)) to obtain a yellow solid product (220 mg, yield 70.2%).

$^1$H NMR (400 MHz, CDCl$_3$): δ 9.40 (s, 1H), 8.27 (d, J=5.2 Hz, 1H), 8.11 (s, 1H), 7.99 (d, J=8.4 Hz, 1H), 7.78 (d, J=8.0 Hz, 1H), 7.64 (d, J=5.6 Hz, 1H), 7.18 (d, J=7.6 Hz, 1H), 6.55 (s, 1H), 6.52 (d, J=9.2 Hz, 1H), 4.56 (dt, J=11.6, 6.0 Hz, 1H), 3.66 (d, J=12.0 Hz, 2H), 3.32 (dt, J=13.6, 6.8 Hz, 1H), 2.73 (t, J=11.2 Hz, 3H), 2.58 (s, 6H), 2.17-2.01 (m, 2H), 1.90-1.73 (m, 2H), 1.37 (t, J=6.8 Hz, 12H).

LCMS: t=3.38 min, 593.1 (M+H$^+$).

Example 27 Preparation of 5-chloro-$N^4$-(2-(isopropylsulfonyl) pyridin-3-yl)-$N^2$-(2-methoxy-4-(1-methyl-1,2,3,6-tetrahydropyridin-4-yl) phenyl) pyrimidine-2,4-diamine (Compound I-84)

Preparation scheme:

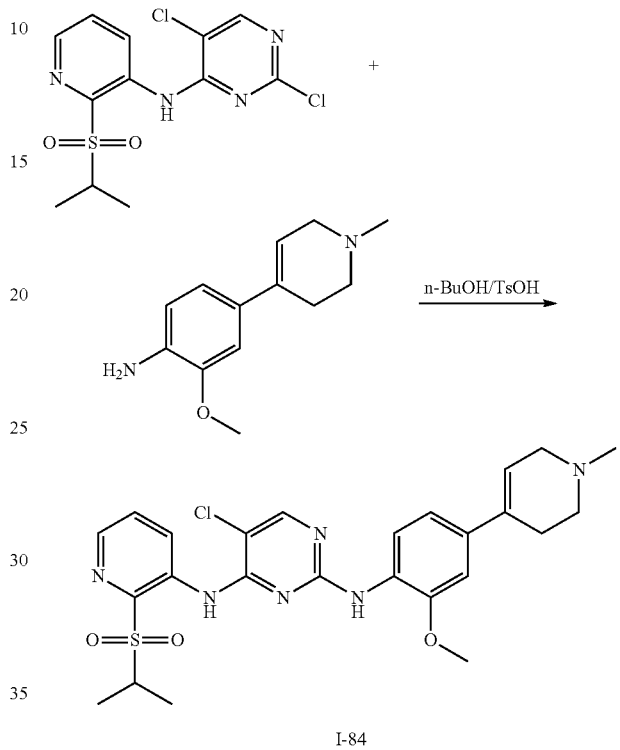

I-84

To n-BuOH (2.5 mL) was added 2,5-dichloro-N-(2-(isopropylsulfonyl) pyridin-3-yl) pyrimidine-4-amine (183 mg, 0.527 mmol) and 2-methoxy-4-(1-methyl-1,2,3,6-tetrahydropiperidin-4-yl) aniline (compound 4) (115 mg, 0.527 mmol), and then added with p-toluenesulfonic acid (91 mg, 0.527 mmol). The mixture was heated to 120° C. and stirred for 3 hours. After LCMS indicated the reaction was completed, the reaction mixture was cooled to room temperature, then diluted with ethyl acetate (25 mL), washed with water and saturated aqueous sodium chloride. The obtained crude product was dried over anhydrous sodium sulfate, filtered and concentrated, and further isolated by column chromatography (DCM/MeOH (v/v=40:1 to 20:1)) to obtain a yellow solid product, compound I-84 (115 mg, yield 41.2%).

$^1$H NMR (400 MHz, CDCl$_3$): δ 10.06 (s, 1H), 9.17 (d, J=8.8 Hz, 1H), 9.11 (dd, J=18.8, 6.0 Hz, 1H), 8.52-8.45 (m, 1H), 8.39 (d, J=4.4 Hz, 1H), 8.28-8.19 (m, 1H), 8.08 (d, J=8.8 Hz, 1H), 7.48 (d, J=3.6 Hz, 1H), 6.97-6.90 (m, 1H), 6.03 (s, 1H), 3.91 (s, 3H), 3.13 (d, J=2.8 Hz, 2H), 2.69 (t, J=5.6 Hz, 3H), 2.60 (s, 2H), 2.42 (s, 3H), 1.39 (t, J=6.2 Hz, 6H).

LCMS: t=3.25 min, 529.1 (M+H$^+$).

During preparation of the compound I-84, said 2-methoxy-4-(1-methyl-1,2,3,6-tetrahydropiperidin-4-yl) aniline (compound 4) was synthesized by a route below:

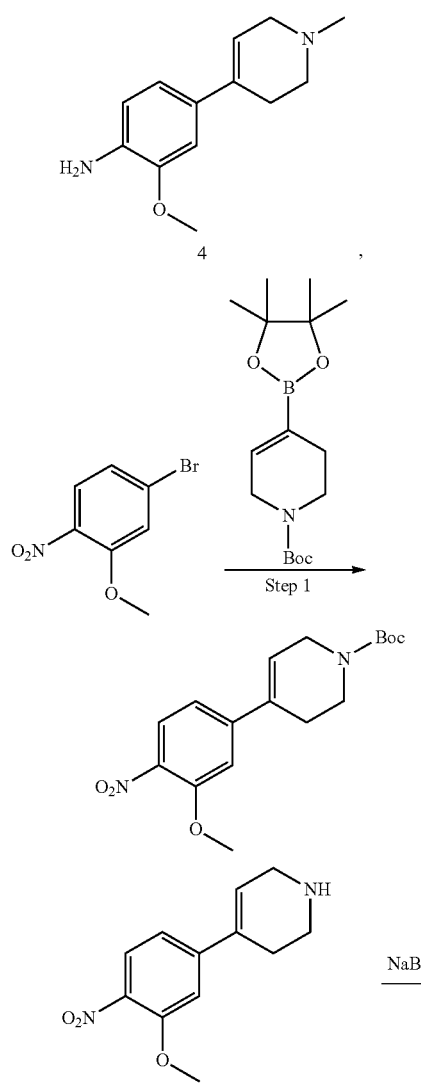

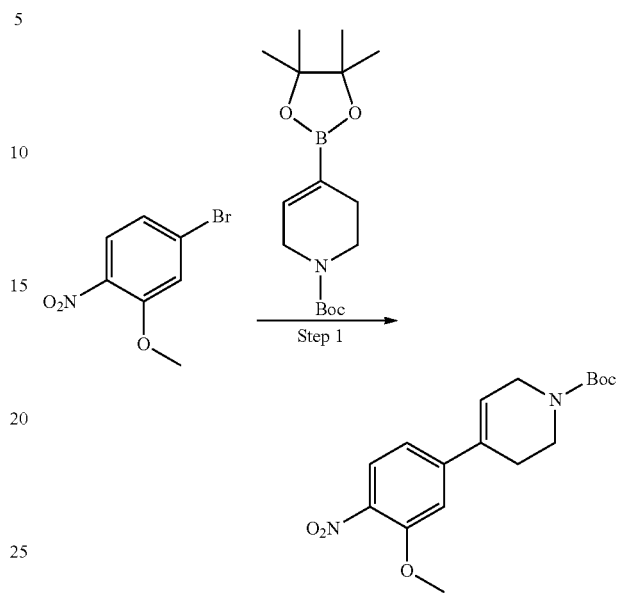

Step 1 Preparation of 4-(3-methoxy-4-nitrophenyl)-3,6-dihydropiperidine-1 (2H)-tert-butyl carboxylate To a 100 mL flask was added compound 4-bromo-2-methoxy-1-nitrobenzene (1.5 g, 6.46 mmol), N-Boc-1,2,5,6-tetrahydropyridine-4-boronic acid pinacol ester (2.199 g, 7.11 mmol), potassium carbonate (2.68 g, 19.39 mmol) and Pd(Ph₃P)₄ (0.374 g, 0.323 mmol), and then added with 1,4-dioxane. After gas replacement with nitrogen, the mixture was heated under nitrogen atmosphere to 90° C. and stirred overnight. After TLC indicated the reaction was completed, the reaction mixture was evaporated to remove solvent, diluted with water and extracted with dichloromethane. The obtained organic phase was dried over anhydrous sodium sulfate, filtered and further isolated and purified by column chromatography to give a white solid product (1.72 g, yield 65%).

LCMS: t=4.30 min, 279.0 (M-55).

Step 2 Preparation of 4-(3-methoxy-4-nitrophenyl)-1,2,3,6-tetrahydropiperidine trifluoroacetate

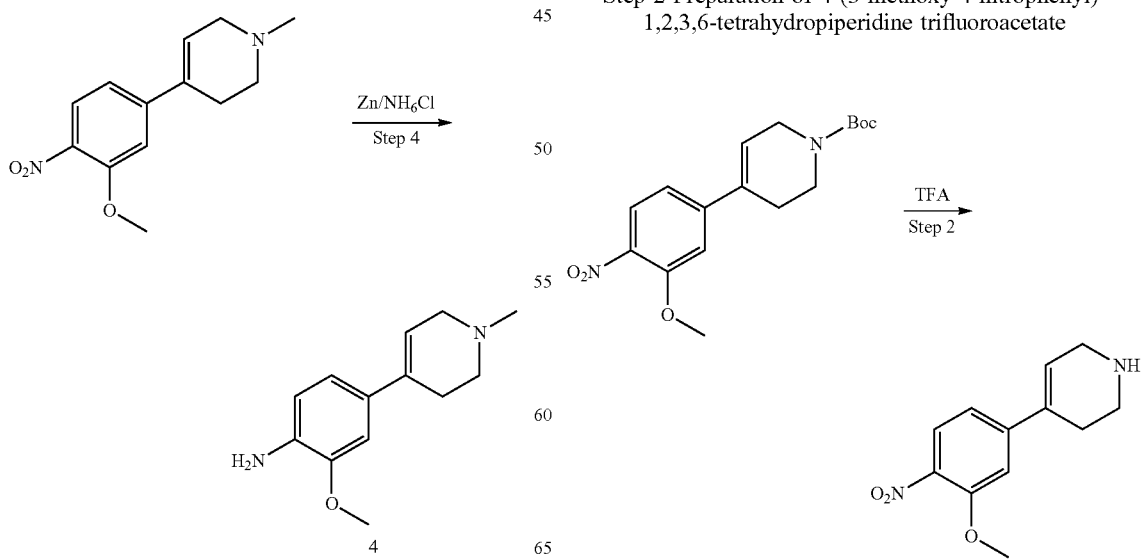

To 10 mL dichloromethane was added compound 4-(3-methoxy-4-nitrophenyl)-5,6-dihydropiperidine-1(2H)-tert-butyl carboxylate (1.72 g, 5.14 mmol), and TFA (4 mL) was added drop wise at room temperature. The mixture was stirred overnight. After the reaction was completed, the mixture was evaporated to remove trifluoroacetic acid, thus obtaining an oily product (1.79 g, yield 100%).

Step 3 Preparation of 4-(3-methoxy-4-nitrophenyl)-1-methyl-1,2,3,6-tetrahydropiperidine

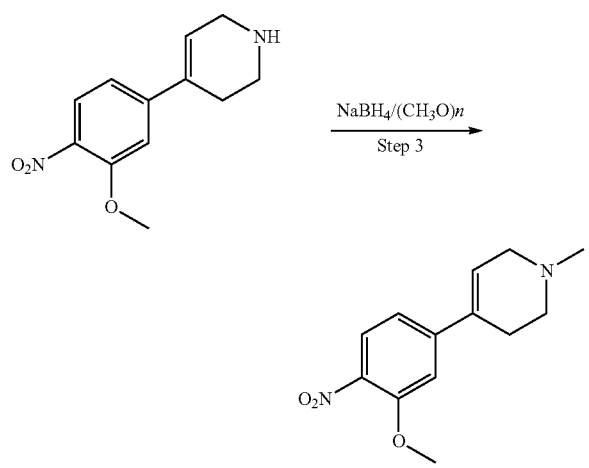

To 10 mL methanol was added compound 4-(3-methoxy-4-nitrophenyl)-1,2,3,6-tetrahydropiperidine trifluoroacetate (0.6 g, 1.723 mmol), and then added with paraformaldehyde (0.155 g, 5.17 mmol). The mixture was stirred at room temperature for 0.5 hours. Sodium cyano-borohydride (0.325 g, 5.17 mmol) was added in portions, and the resulting mixture was stirred at room temperature overnight. After TLC indicated the reaction was completed, the mixture was diluted with 50 mL water and extracted with EtOAc (30 mL×2). The combined organic phase was dried over anhydrous sodium sulfate, filtered and evaporated to remove solvent, and further isolated by column chromatography to give an oily product (0.2 g, yield 47%).

LCMS: t=1.57 min, 249.0 (M+H$^+$).

Step 4 Preparation of 2-methoxy-4-(1-methyl-1,2,3,6-tetrahydropiperidin-4-yl) aniline

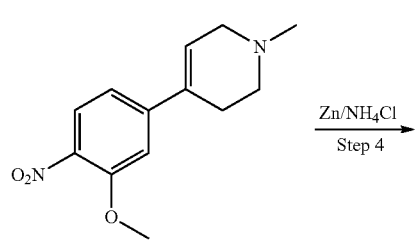

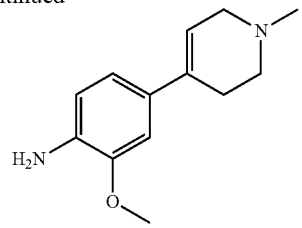

To 15 mL methanol was added compound 4-(3-methoxy-4-nitrophenyl)-1-methyl-1,2,3,6-tetrahydropiperidine (0.2 g, 0.806 mmol), and then added with ammonium chloride (0.215 g, 4.03 mmol). Zinc powder (0.263 g, 4.03 mmol) was added in portions under stirring at room temperature, and the mixture was refluxed under heating overnight. After TLC indicated the reaction was completed, the mixture was filtered under decreased pressure and evaporated to remove solvent. The obtained crude product was dissolved with DCM, washed with sodium bicarbonate, dried over anhydrous sodium sulfate, filtered and evaporated to give a solid product (157 mg, yield 90%).

LCMS: t=0.45 min, 219.0 (M+H$^+$).

Example 28 Preparation of 5-chloro-N$^2$-(4-(1-isopropyl-1,2,3,6-tetrahydropyridin-4-yl)-2-methoxyphenyl)-N$^4$-(2-(isopropylsulfonyl) pyridin-3-yl) pyrimidine-2,4-diamine (Compound I-85)

Scheme

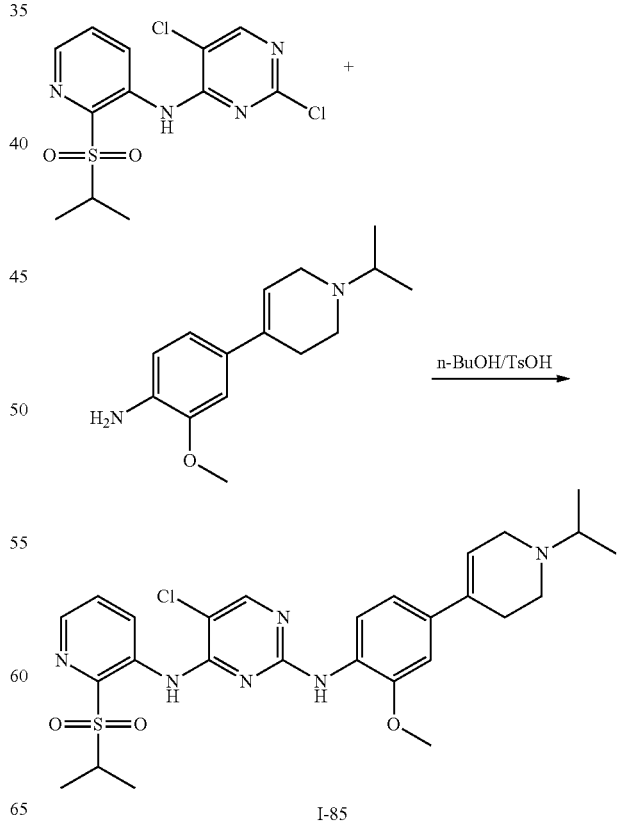

I-85

To n-BuOH (2.5 mL) was added 2,5-dichloro-N-(2-(isopropylsulfonyl) pyridin-3-yl) pyrimidine-4-amine (183 mg, 0.527 mmol) and 4-(1-isopropyl-1,2,3,6-tetrahydropiperidin-4-yl)-2-methoxyaniline (compound 11) (130 mg, 0.527 mmol), and then added with p-toluenesulfonic acid (91 mg, 0.527 mmol). The mixture was heated to 120° C. and stirred for 3 hours. After LCMS indicated the reaction was completed, the reaction mixture was cooled to room temperature, diluted with ethyl acetate (25 mL), and washed with water and saturated aqueous sodium chloride. The obtained crude product was dried over anhydrous sodium sulfate, filtered and concentrated, and further isolated and purified by column chromatography to give a yellow solid product, compound I-85 (52 mg, yield 17.7%).

$^1$H NMR (400 MHz, CDCl$_3$): δ 10.06 (s, 1H), 9.12 (s, 1H), 8.41 (s, 1H), 8.16 (d, J=21.2 Hz, 1H), 7.54 (s, 1H), 6.91 (s, 1H), 5.97 (s, 1H), 5.29-5.16 (m, 1H), 3.91 (s, 3H), 3.72-3.58 (m, 3H), 3.25-3.02 (m, 5H), 1.36 (L, J=39.6 Hz, 12H).

LCMS: t=3.43 min, 557.2 (M+H$^+$).

During preparation of the compound I-85, said 4-(1-isopropyl-1,2,3,6-tetrahydropiperidin-4-yl)-2-methoxyaniline (compound 11) was synthesized by a route below

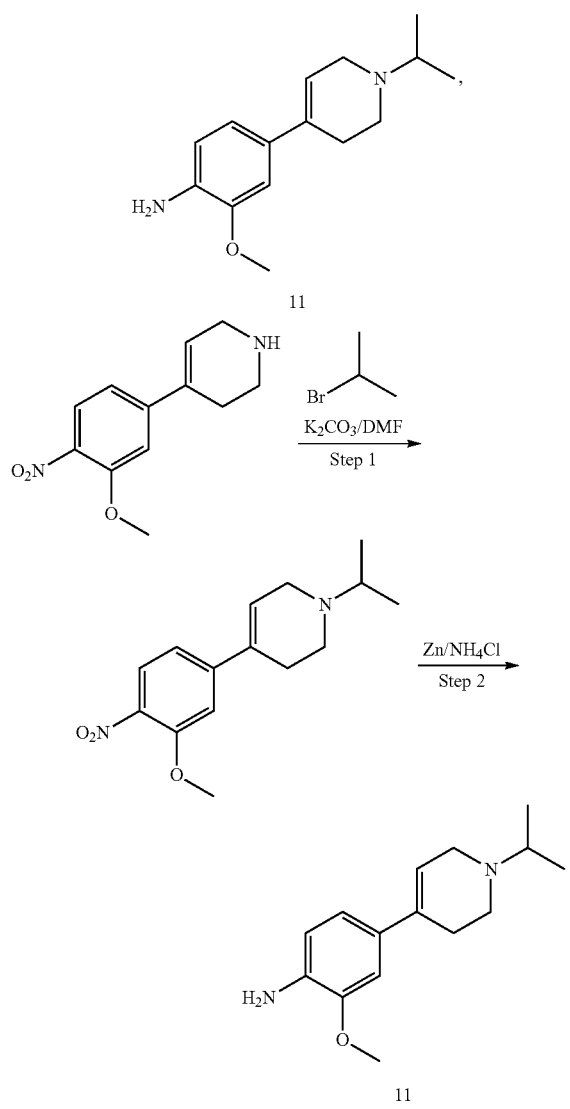

Step 1 Preparation of 1-isopropyl-4-(3-methoxy-4-nitrophenyl)-1,2,3,6-tetrahydropiperidine

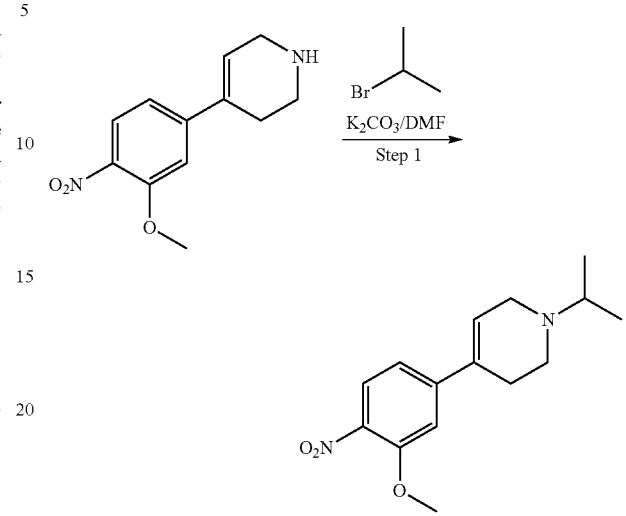

To 15 mL DMF was added compound 4-(3-methoxy-4-nitrophenyl)-1,2,3,6-tetrahydropiperidine trifluoroacetate (1.2 g, 3.45 mmol), and then added with potassium carbonate (1.905 g, 13.78 mmol) and isopropyl bromide (0.642 ml, 6.89 mmol) successively. The mixture was heated to 80° C. and stirred overnight. After TLC indicated the reaction was completed, the reaction mixture was diluted with water and extracted with EtOAc. The obtained organic phase was washed with saturated aqueous sodium chloride, dried over anhydrous sodium sulfate, filtered and evaporated to dryness, and further isolated and purified by column chromatography to give an oily product (0.3 g, yield 27%).

LCMS: t=2.40 min, 277.0 (M+H$^+$).

Step 2 Preparation of 4-(1-isopropyl-1,2,3,6-tetrahydropiperidin-4-yl)-2-methoxyaniline

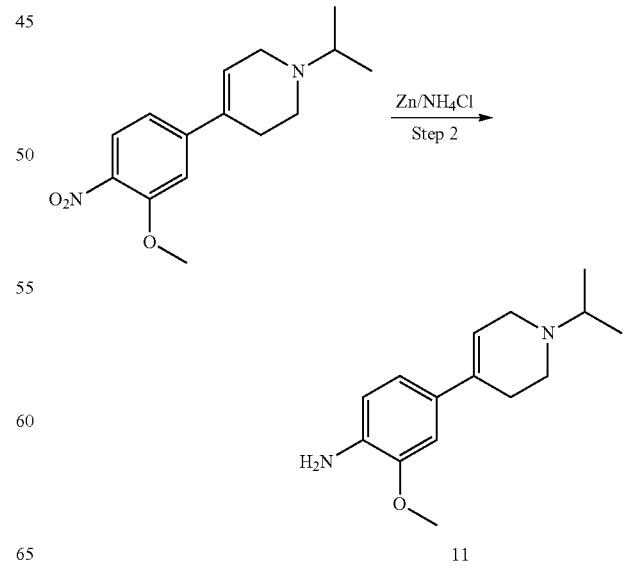

To methanol (15 mL) was added compound 1-isopropyl-4-(3-methoxy-4-nitrophenyl)-1,2,3,6-tetrahydropiperidine (0.3 g, 1.086 mmol), and then added with ammonium chloride (0.410 g, 7.67 mmol). Zinc powder (15.21 g, 233 mmol) was added in portions at room temperature, and the mixture was refluxed under heating for 3 hours. After TLC indicated the reaction was completed, the reaction mixture was cooled to room temperature, filtered and evaporated to dryness. The obtained crude product was dissolved with DCM, washed with sodium bicarbonate, dried over anhydrous sodium sulfate, filtered and concentrated to give a yellow oily product (0.26 g, yield 97%).

LCMS: t=0.55 min, 247.1 (M+H$^+$).

Example 29 Preparation of 5-chloro-N$^2$-(4-(1-isopropyl-1,2,3,6-tetrahydropyridin-4-yl)-2-methoxyphenyl)-N$^4$-(2-(isopropylsulfonyl) thiophen-3-yl) pyrimidine-2,4-diamine (Compound I-86)

Preparation Scheme

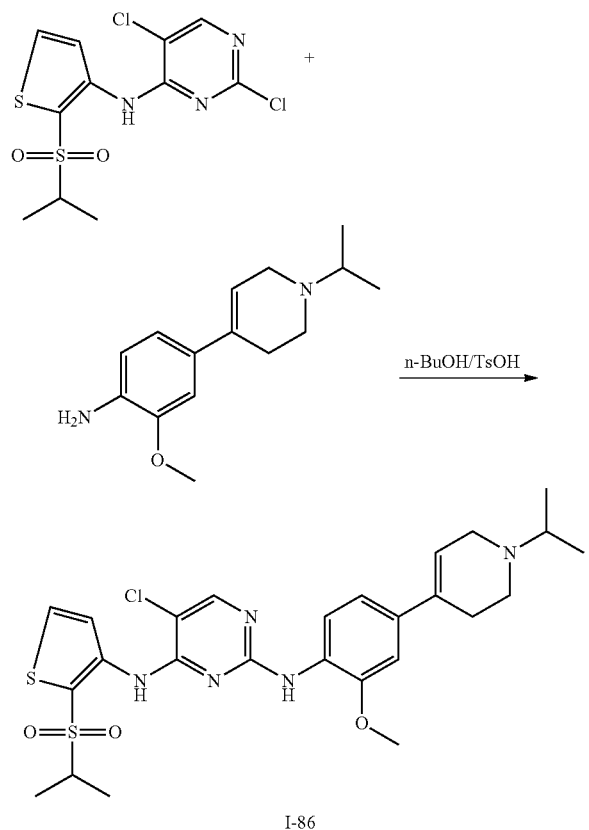

I-86

To n-BuOH (2.5 mL) was added 2,5-dichloro-N-(2-(isopropylsulfonyl) thiophen-3-yl) pyrimidine-4-amine (185 mg, 0.525 mmol) and compound 11 (130 mg, 0.528 mmol), and then added with p-toluenesulfonic acid (91 mg, 0.528 mmol). The mixture was heated to 120° (and stirred for 3 hours. After LCMS indicated the reaction was completed, the reaction mixture was cooled to room temperature, diluted with ethyl acetate (25 mL), and washed with water and saturated aqueous sodium chloride. The obtained crude product was dried over anhydrous sodium sulfate, filtered and concentrated, and further isolated and purified by column chromatography to give a yellow solid product, compound I-86 (65 mg, yield 22%).

$^1$H NMR (400 MHz, CDCl$_3$): δ 9.42 (s, 1H), 8.15 (s, 1H), 7.73 (s, 1H), 7.57 (s, 1H), 7.07-6.83 (m, 1H), 5.97 (s, 1H), 3.90 (s, 3H), 3.76 (s, 2H), 3.58 (s, 1H), 3.33-3.30 (m, 3H), 2.04 (s, 1H), 1.70 (s, 1H), 1.58-1.27 (m, 6H).

LCMS: t=3.63 min, 562.1 (M+H$^+$).

Example 30 Preparation of 5-chloro-N$^2$-(4-(4-(isopropylpiperazin-1-yl)-2-methoxy-5-methylphenyl)-N$^4$-(2-(isopropylsulfonyl) pyridin-3-yl) pyrimidine-2,4-diamine (Compound I-88)

Preparation Scheme

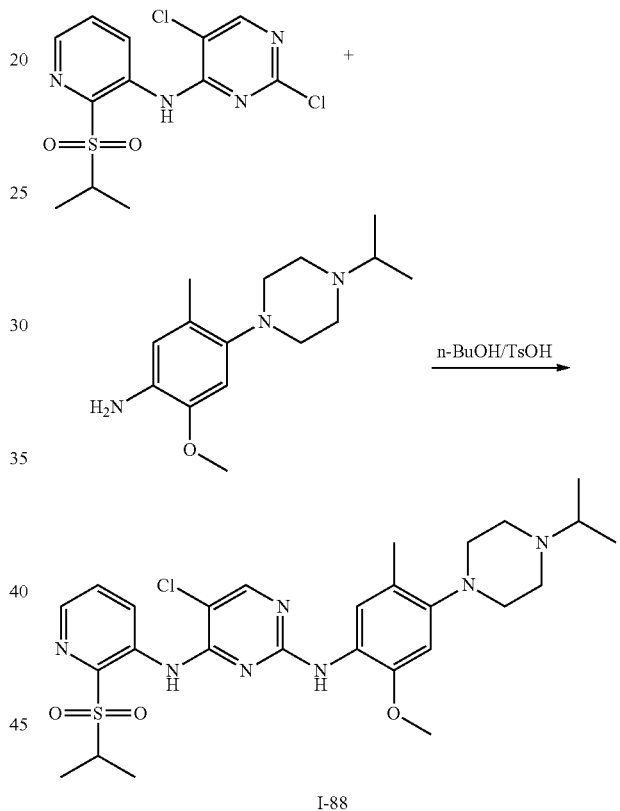

I-88

To n-BuOH (2.5 mL) was added 2,5-dichloro-N-(2-(isopropylsulfonyl) pyridin-3-yl) pyrimidine-4-amine (183 mg, 0.527 mmol) and 4-(4-isopropylpiperazin-1-yl)-2-methoxy-5-methylaniline (compound 10) (139 mg, 0.527 mmol), and then added with p-toluenesulfonic acid (91 mg, 0.527 mmol). The mixture was heated to 120° C. and stirred for 3 hours. After LCMS indicated the reaction was completed, the reaction mixture was cooled to room temperature, diluted with ethyl acetate (25 mL), and washed with water and saturated aqueous sodium chloride. The obtained crude product was dried over anhydrous sodium sulfate, filtered and concentrated, and further isolated and purified by column chromatography to give a yellow solid product, compound I-88 (171 mg, yield 56.5%).

$^1$H NMR (400 MHz, CDCl$_3$): δ 10.07 (s, 1H), 9.20 (d, J=8.4 Hz, 1H), 8.36 (d, J=4.0 Hz, 1H), 8.16 (s, 1H), 7.88 (s, 1H), 7.44 (dd, J=8.4, 4.4 Hz, 1H), 7.30 (s, 1H), 6.70 (s, 1H), 3.96-3.87 (m, 1H), 3.85 (s, 3H), 3.04 (s, 4H), 2.82 (s, 5H), 2.20 (s, 3H), 1.38 (d, J=6.8 Hz, 6H), 1.20 (s, 6H).

LCMS: t=3.39 min, 574.1 (M+H⁺).

During preparation of the compound I-88, said 4-(4-isopropylpiperazin-1-yl)-2-methoxy-5-methylaniline (compound 10) was synthesized by a route below

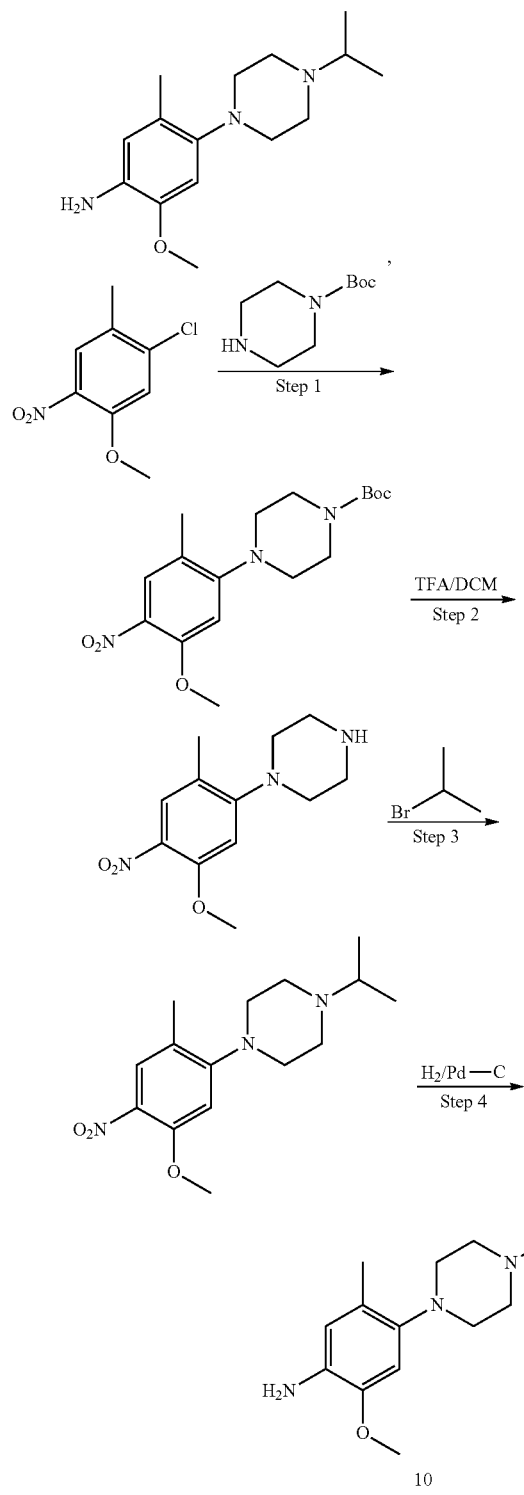

Step 1 Preparation of 4-(5-methoxy-2-methyl-4-nitrophenyl) piperazine-1-tert-butyl carboxylate

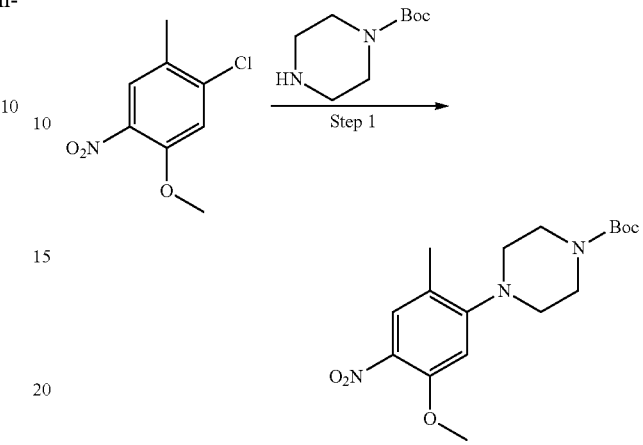

To a 100 mL flask was added compound 1-chloro-5-methoxy-2-methyl-4-nitrobenzene (2 g, 9.92 mmol), N-Boc piperazine (2.032 g, 10.91 mmol), cesium carbonate (9.70 g, 29.8 mmol), Pd$_2$(dba)$_3$ (0.454 g, 0.496 mmol) and Xantphos (0.574 g, 0.992 mmol), and then added with 20 mL 1,4-dioxane. After gas replacement with nitrogen, the mixture was heated to 100° C. under nitrogen atmosphere and stirred overnight. After TLC indicated the reaction was completed, the resulting mixture was diluted with 100 mL water and extracted with ethyl acetate (50 mL×2). The obtained organic phase was washed with saturated aqueous sodium chloride, dried over anhydrous sodium sulfate, filtered and evaporated to remove solvent, and further isolated by column chromatography to give a yellow solid product (2 g, yield 57%).

LCMS: t=4.361 min, 296.0 (M-55).

Step 2 Preparation of 1-(5-methoxy-2-methyl-4-nitrophenyl) piperazine

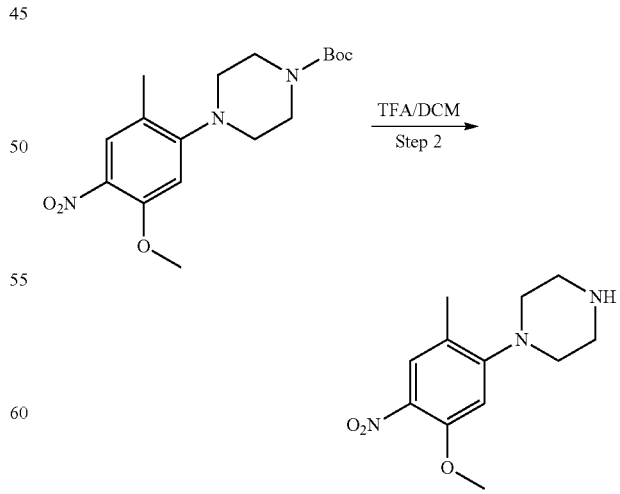

To 10 mL dichloromethane was added compound 4-(5-methoxy-2-methyl-4-nitrophenyl) piperazine-1-tert-butyl carboxylate (2 g, 5.69 mmol), and then added with TFA (4 mL) drop wise at room temperature. The mixture was stirred for 4 hours. After TLC indicated the reaction was completed, the mixture was evaporated to give a black oily product (1.9 g, yield 100%).

Step 3 Preparation of 1-isopropyl-4-(5-methoxy-2-methyl-4-nitrophenyl) piperazine

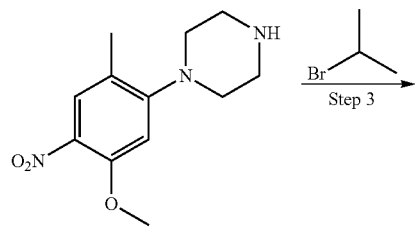

To 20 mL DMF was added compound 1-(5-methoxy-2-methyl-4-nitrophenyl) piperazine (1.9 g, 5.69 mmol), and then added with potassium carbonate (2.36 g, 17.05 mmol) and isopropyl bromide (1.4 g, 11.37 mmol) successively. The mixture was heated to 80° (and stirred for 3 hours. After TLC indicated the reaction was completed, the mixture was diluted with water and extracted with EtOAc. The obtained organic phase was washed with saturated aqueous sodium chloride, dried over anhydrous sodium sulfate, filtered and evaporated to dryness, and further isolated by column chromatography to give a yellow oily product (0.68 g. yield 41%).

LCMS: t=2.676 min, 294.1 (M+H⁺).

Step 4 Preparation of 4-(4-isopropylpiperazin-1-yl)-2-methoxy-5-methylaniline

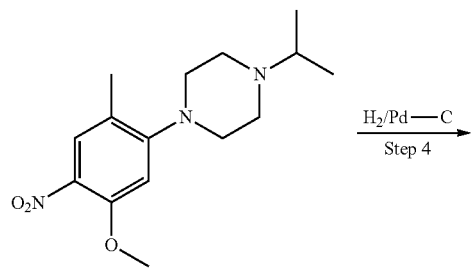

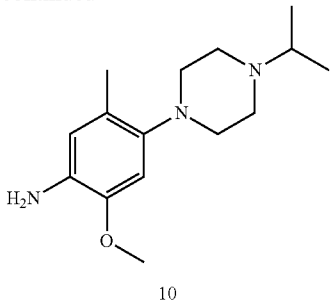

To 10 mL methanol was added compound 1-isopropyl-(5-methoxy-2-methyl-4-nitrophenyl) piperazine (0.68 g, 2.32 mmol), and then added with palladium on carbon (100 mg). After gas replacement with hydrogen, the mixture was stirred under hydrogen atmosphere at room temperature overnight. After TLC indicated the reaction was completed, the mixture was filtrated to remove the palladium on carbon, and concentrated under decreased pressure to give a product (0.4 g, yield 65%).

LCMS: t=4.36 min, 296.1 (M-55).

Example 31 Preparation of 5-chloro-$N^2$-(2-difluoromethoxy)-4-(4-(dimethylamino) piperidin-1-yl) phenyl)-$N^4$-(2-(isopropylsulfonyl) phenyl) pyrimidine-2,4-diamine (Compound I-95)

Scheme

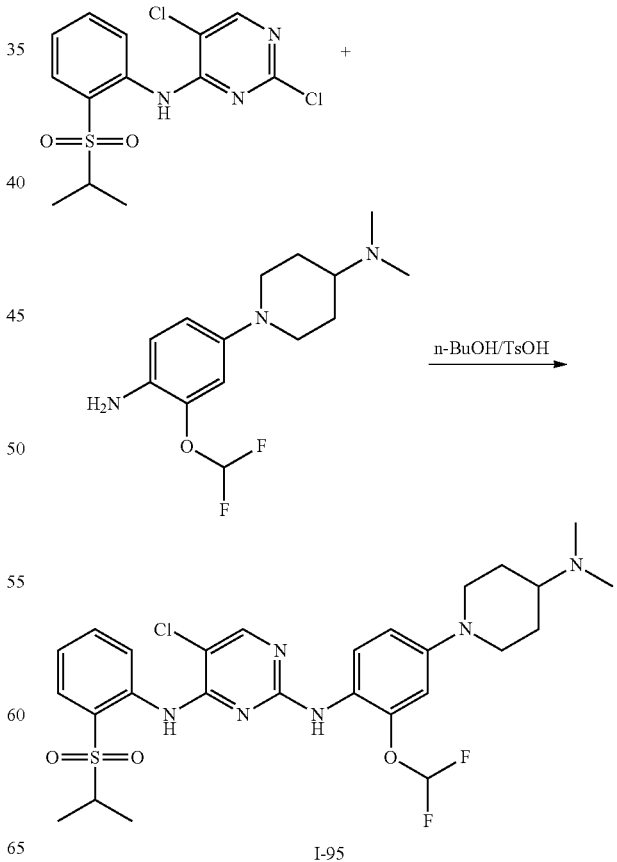

I-95

To n-BuOH (2.5 mL) was added 2,5-dichloro-N-(2-(isopropylsulfonyl) phenyl) pyrimidine-4-amine (180 mg, 0.520 mmol) and compound 3 (150 mg, 0.526 mmol), and then added with p-toluenesulfonic acid (90 mg, 0.523 mmol). The mixture was heated to 120° C. and stirred for 3 hours. After LCMS indicated the reaction was completed, the reaction mixture was cooled to room temperature, then diluted with ethyl acetate (25 mL), washed with water and saturated aqueous sodium chloride. The obtained crude product was dried over anhydrous sodium sulfate, filtered and concentrated, and further isolated and purified by column chromatography to give a yellow solid product, compound I-95 (115 mg, yield 37.2%).

$^1$H NMR (400 MHz, CDCl$_3$): δ 9.60 (s, 1H), 8.53 (d, J=8.4 Hz, 1H), 8.12 (s, 1H), 8.00 (d, J=8.8 Hz, 1H), 7.90 (dd, J=8.0, 1.2 Hz, 1H), 7.58 (t, J=7.2 Hz, 1H), 7.28-7.20 (m, 1H), 7.00 (s, 1H), 6.73 (s, 1H), 6.48 (t, J=73.6 Hz, 2H), 3.65 (d, J=12.8 Hz, 2H), 3.25-3.19 (m, 1H), 2.99-2.85 (m, 1H), 2.72 (dd, J=24.4, 13.2 Hz, 2H), 2.50 (s, 6H), 2.10-2.03 (m, 2H), 1.80-1.72 (m, 2H), 1.29 (t, J=6.8 Hz, 6H).

LCMS: t=3.75 min, 595.14 (M+H$^+$).

Example 32 Preparation of 5-chloro-N$^2$-(4-(4-(dimethylamino) piperidin-1-yl)-2-methoxy-5-methylphenyl)-N$^4$-(2-(isopropylsulfonyl) pyridin-3-yl) pyrimidine-2,4-diamine (Compound I-98)

Preparation Scheme

To n-BuOH (2.5 mL) was added 2,5-dichloro-N-(2-(isopropylsulfonyl) pyridin-3-yl) pyrimidine-4-amine (183 mg, 0.527 mmol) and 1-(4-amino-5-methoxy-2-methylphenyl)-N,N-dimethylpiperidine-4-amine (compound 2) (139 mg, 0.527 mmol), and then added with p-toluenesulfonic acid (91 mg, 0.527 mmol). The mixture was heated to 120° C. and stirred for 3 hours. After LCMS indicated the reaction was completed, the mixture was cooled to room temperature, diluted with ethyl acetate (25 mL), and washed with water and saturated aqueous sodium chloride. The resulting crude product was dried over anhydrous sodium sulfate, filtered and concentrated, and then further isolated and purified by column chromatography to give a white solid product, compound I-98 (50 mg, yield 16.5%).

$^1$H NMR (400 MHz, CDCl$_3$): δ 10.08 (s, 1H), 9.19 (dd, J=8.4, 1.2 Hz, 1H), 8.37 (dd, J=4.4, 1.2 Hz, 1H), 8.16 (s, 1H), 7.91 (s, 1H), 7.55-7.43 (m, 1H), 7.32 (s, 1H), 6.60 (s, 1H), 3.95-3.91 (m, 1H), 3.86 (s, 3H), 3.23 (t, J=12.2 Hz, 2H), 3.16 (t, J=12.0 Hz, 1H), 2.79 (s, 6H), 2.74 (t, J=11.2 Hz, 2H), 2.28 (t, J=12.0 Hz, 2H), 2.18 (s, 3H), 1.97-1.94 (m, 2H), 1.39 (d, J=6.8 Hz, 6H).

LCMS: t=3.52 min, 574.3 (M+H$^+$).

During preparation of the compound I-98, said 1-(4-amino-5-methoxy-2-methylphenyl)-N,N-dimethylpiperidine-4-amine (compound 2) was synthesized by a route below

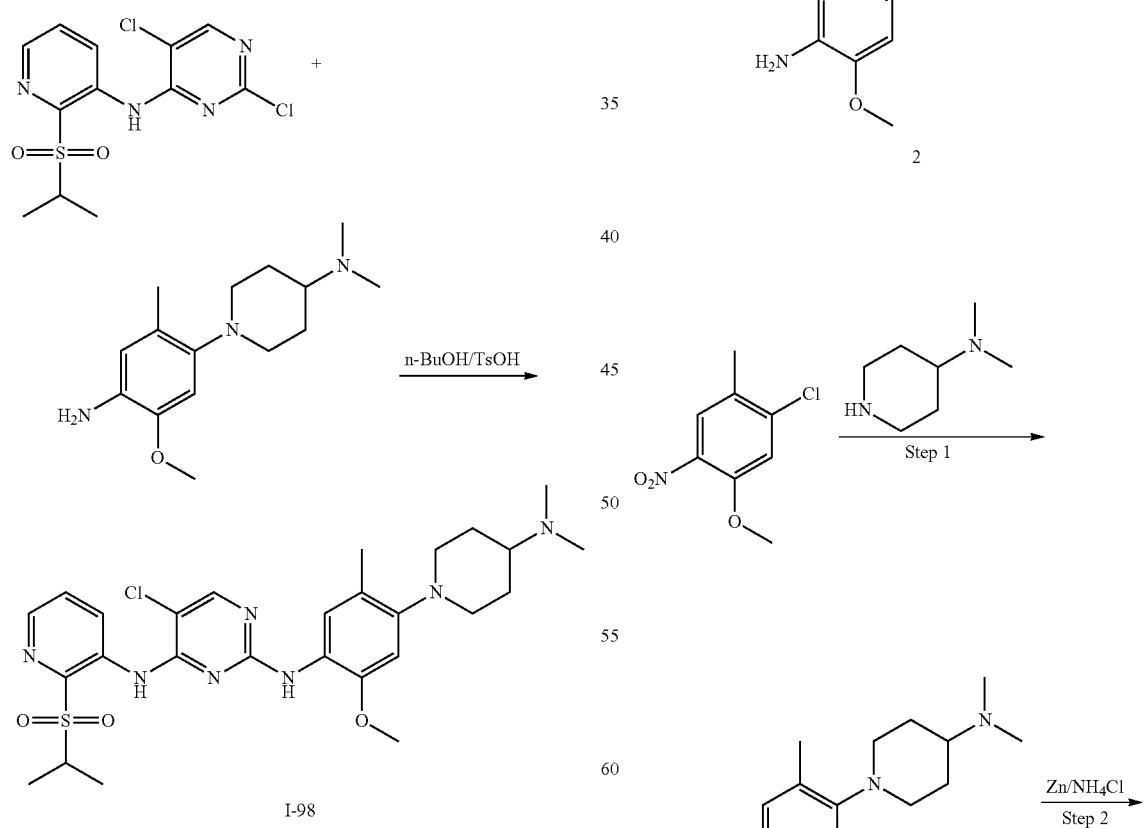

91
-continued

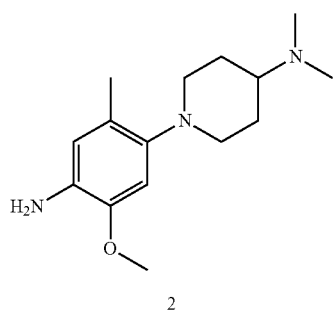

2

Step 1 Preparation of 1-(5-methoxy-2-methyl-4-nitrophenyl)-N,N-dimethylpiperidine-4-amine

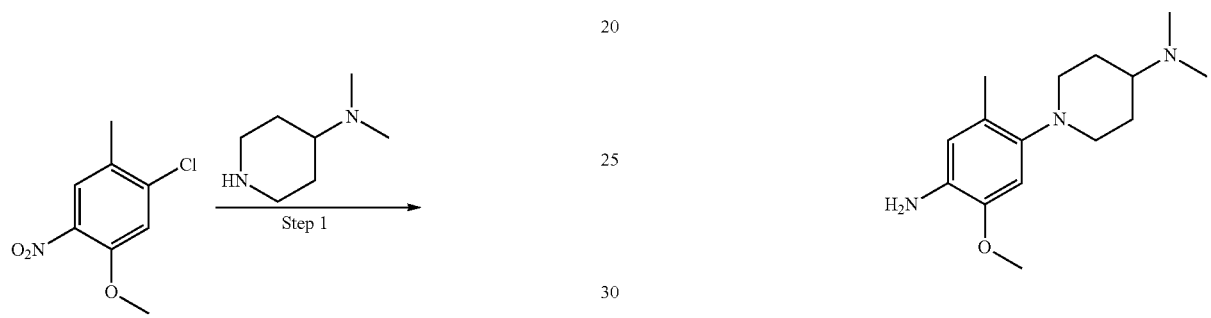

To a 10 mL microwave tube was added compound 1-chloro-5-methoxy-2-methyl-4-nitrobenzene (2 g, 9.92 mmol), N,N-dimethylpiperidine hydrochloride (2.195 g, 10.91 mmol), cesium carbonate (16.16 g, 49.6 mmol). Pd$_2$(dba)$_3$ (0.454 g, 0.496 mmol) and Xantphos (0.574 g, 0.992 mmol), and then added with DMF (20 mL). After air-blew with nitrogen for 2 minutes, the mixture was stirred via microwave at 130° C. (for 40 minutes. After TLC indicated the reaction was completed, the reaction mixture was cooled to room temperature, diluted with water, and extracted with ethyl acetate. The obtained organic phase was washed with saturated aqueous sodium chloride, dried over anhydrous sodium sulfate, filtered and concentrated, and further isolated by column chromatography (DCM:MeOH 20:1) to give a brown solid product (0.45 g. yield 15.46%).

LCMS: t=2.69 min, 294.1 (M+H$^+$).

92

Step 2 Preparation of 1-(4-amino-5-methoxy-2-methylphenyl)-N,N-dimethylpiperidine-4-amine

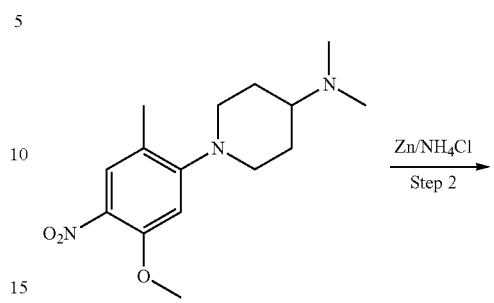

To a 100 mL flask was added compound 1-(5-methoxy-2-methyl-4-nitrophenyl)-N,N-dimethylpiperidine-4-amine (0.45 g, 1.534 mmol) and ammonium chloride (0.410 g, 7.67 mmol), and then added with 10 mL methanol. Zinc powder (0.501 g, 7.67 mmol) was added in portions under stirring at room temperature, and the mixture was refluxed under heating for 3 hours. After TLC indicated the reaction was completed, the reaction mixture was cooled to room temperature, filtered under decreased pressure, evaporated to dryness and further dissolved with DCM. The obtained mixture was washed with sodium bicarbonate, dried over anhydrous sodium sulfate, filtered and concentrated to give a white product (0.38 g, yield 80%).

LCMS: t=0.43 min, 264.1 (M+H$^+$).

Example 33 Preparation of 5-chloro-N$^2$-(2-(difluoromethoxy)-4-(4-(dimethylamino) piperidin-1-yl)-5-methylphenyl)-N$^4$-(2-(isopropylsulfonyl) phenyl) pyrimidine-2,4-diamine (Compound I-102)

Preparation Scheme

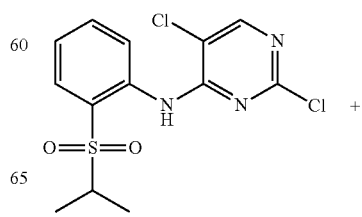 +

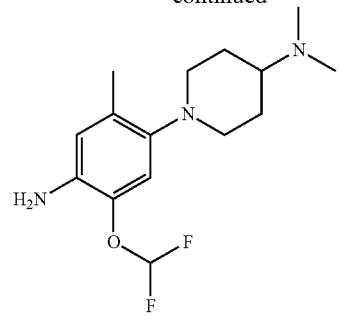

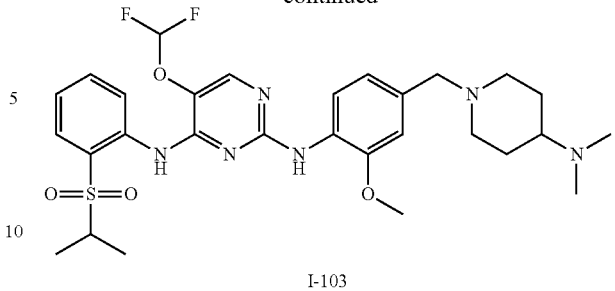

I-103

To n-BuOH (2.5 mL) was added compound a (200 mg, 0.529 mmol) and compound b (140 mg, 0.529 mmol), and then added with p-toluenesulfonic acid (91 mg, 0.529 mmol). The mixture was heated to 120° C. and stirred for 3 hours. After LCMS indicated the reaction was completed, the mixture was cooled to room temperature, diluted with ethyl acetate (25 mL), and washed with water and saturated aqueous sodium chloride. The resulting crude product was dried over anhydrous sodium sulfate, filtered and concentrated, and then further isolated by column chromatography (DCM/MeOH (v/v=40:1 to 20:1)) to give a light yellow solid product, compound I-103 (136 mg, yield 42.5%).

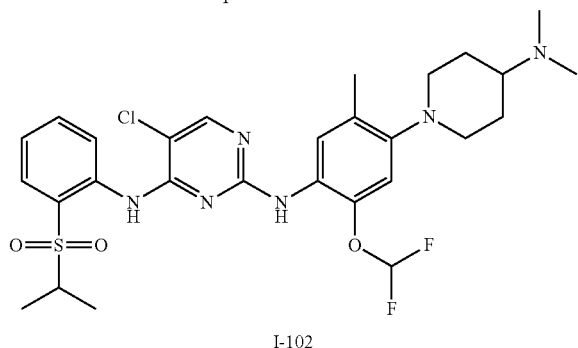

I-102

To n-BuOH (2.5 mL) was added 2,5-dichloro-N-(2-(isopropylsulfonyl) phenyl) pyrimidine-4-amine (183 mg, 0.529 mmol) and 1-(4-amino-5-(difluoromethoxy)-2-methylphenyl)-N,N-dimethylpyridine-4-amine (158 mg, 0.529 mmol), and then added with p-toluenesulfonic acid (91 mg, 0.529 mmol). The mixture was heated to 120° C. and stirred for 3 hours. After LCMS indicated the reaction was completed, the mixture was cooled to room temperature, diluted with ethyl acetate (25 mL), and washed with water and saturated aqueous sodium chloride. The resulting crude product was dried over anhydrous sodium sulfate, filtered and concentrated, and then further isolated and purified by column chromatography to give a yellow solid product, compound I-102 (81 mg, yield 25.2%).

Example 34 Preparation of Compound I-103

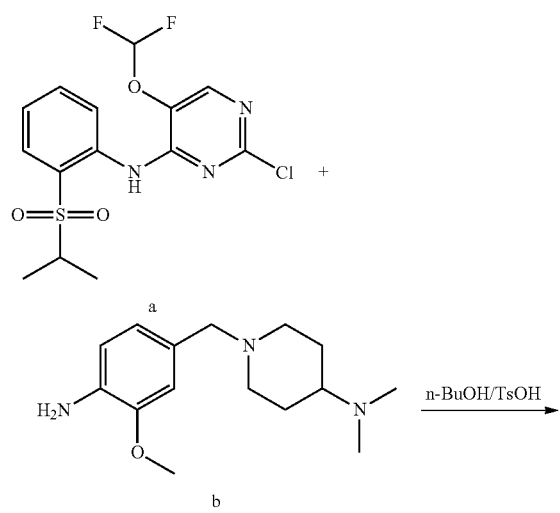

Example 35 Preparation of Compound I-107

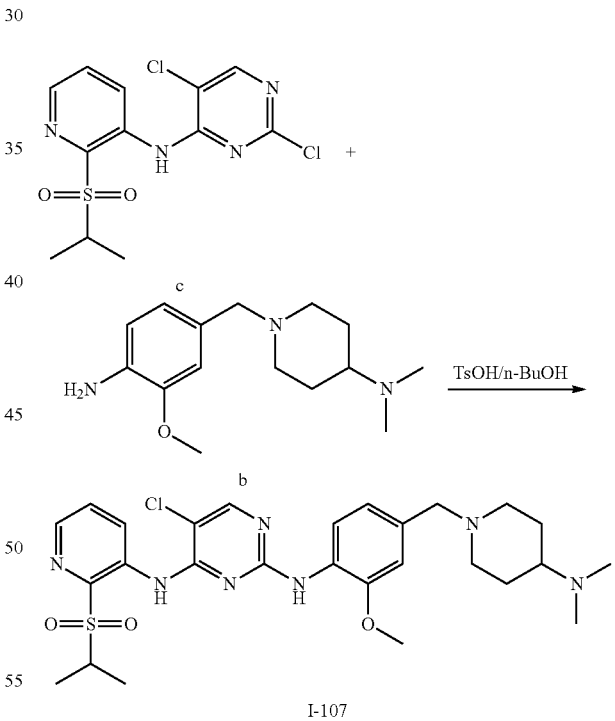

I-107

To n-butanol (1.5 mL) was added compound c (150 mg, 0.43 mmol) and compound b (114 mg, 0.43 mmol), and then added with p-toluenesulfonic acid (74.40 mg, 0.43 mmol). The mixture was heated to 115° C. and stirred for 5 hours. After TLC indicated the reaction was completed, the mixture was cooled to room temperature, evaporated under decreased pressure to remove solvent, and then dissolved with dichlorohexane. The resulting mixture was further washed with saturated sodium bicarbonate and saturated aqueous sodium chloride, dried over anhydrous sodium sulfate, filtered and concentrated to give a crude product, which was further isolated and purified by column chromatography to give a light green solid product, compound I-107 (101 mg, yield 41%).

Example 36 Preparation of Compound I-109

Scheme

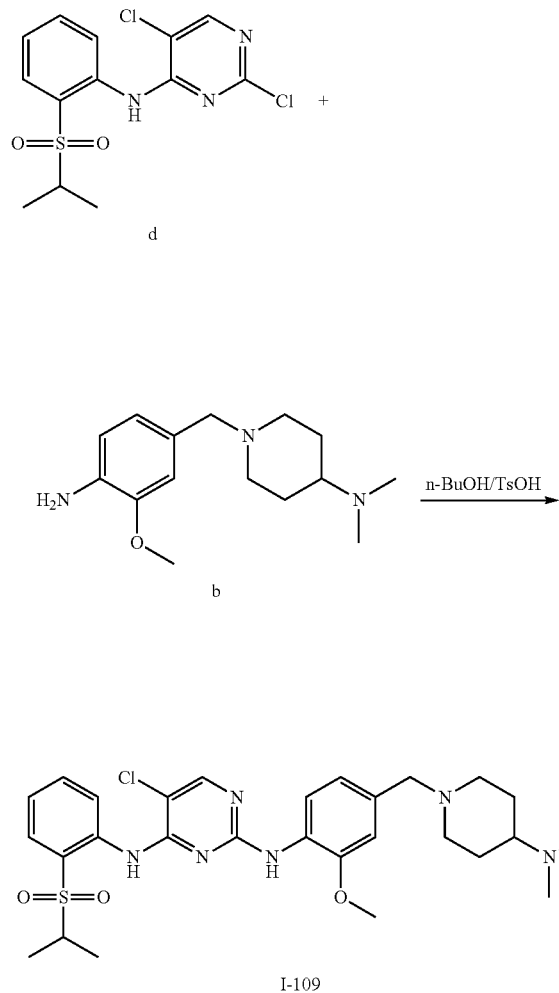

To n-butanol (1.5 mL) was added compound d (137 mg, 0.397 mmol) and compound b (105 mg, 0.397 mmol), and then added with p-toluenesulfonic acid (68 mg, 397 mmol). The mixture was heated to 120° C. and stirred for 3 hours. After LCMS indicated the reaction was completed, the mixture was cooled to room temperature, diluted with ethyl acetate (25 mL), and washed with water and saturated aqueous sodium chloride. The resulting crude product was dried over anhydrous sodium sulfate, filtered and concentrated, and then further isolated by column chromatography (DCM/MeOH (v/v=40:1 to 20:1)) to give a light green solid product, compound I-109 (81 mg, yield 35.6%).

Example 37 Preparation of 5-(difluoromethoxy)-$N^2$-(4-(4-(dimethylamino) piperidin-1-yl)-2-methoxyphenyl)-$N^4$-(2-(isopropylsulfonyl) phenyl) pyrimidine-2,4-diamine (compound I-111)

Preparation Scheme

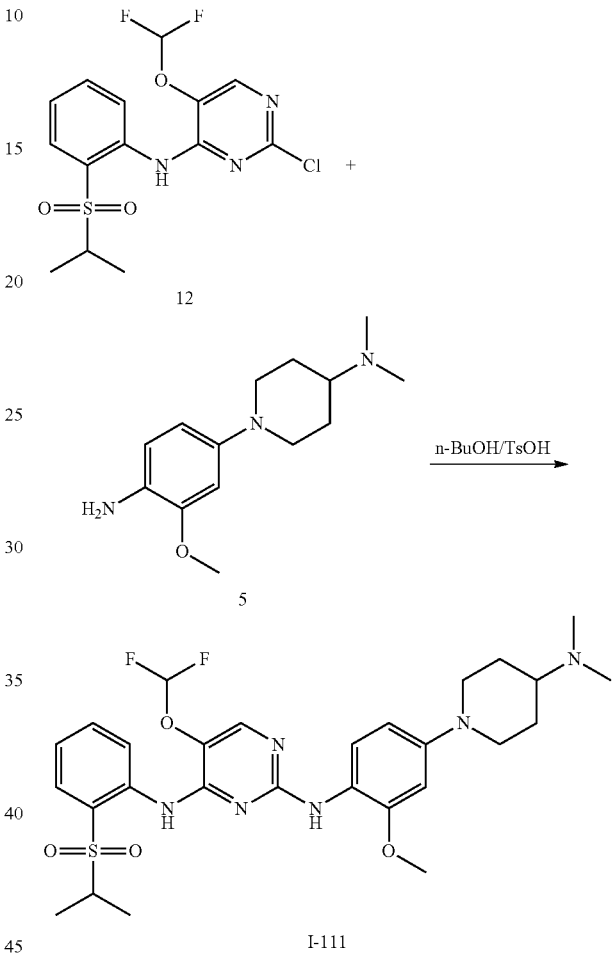

To n-BuOH (2.5 mL) was added 2-chloro-5-(2-fluorinemethoxy)-N-(2-(isopropylsulfonyl) phenyl) pyrimidine-4-amine (compound 12) (200 mg, 0.529 mmol) and 1-(4-amino-3-methoxyphenyl)-N,N-dimethylpiperidine-4-amine (compound 5) (132 mg, 0.529 mmol), and then added with p-toluenesulfonic acid (91 mg, 0.529 mmol). The mixture was heated to 120° C. and stirred for 3 hours. After LCMS indicated the reaction was completed, the mixture was cooled to room temperature, diluted with ethyl acetate (25 mL), and washed with water and saturated aqueous sodium chloride. The resulting crude product was dried over anhydrous sodium sulfate, filtered and concentrated, and then further isolated by column chromatography (DCM/MeOH (v/v=40:1 to 20:1)) to give a light yellow solid product, compound I-111 (121 mg, yield 38.3%).

$^1$H NMR (400 MHz, CDCl$_3$) δ 9.56 (s, 1H), 8.70 (d, J=8.4 Hz, 1H), 8.07-8.04 (m, 2H), 7.87 (dd, J=7.9, 1.2 Hz, 1H), 7.60 (t, J=7.3 Hz, 1H), 7.29 (s, 1H), 7.21 (t, J=7.6 Hz, 1H), 6.62 (d, J=144 Hz, 1H), 6.60-6.54 (m, 1H), 6.50 (dd, J=8.8, 2.4 Hz, 1H), 3.87 (s, 3H), 3.65 (d, J=12.3 Hz, 2H), 3.22 (dt,

J=13.6, 6.8 Hz, 1H), 2.71 (dd. J=12.0, 10.4 Hz, 2H), 2.36 (d, J=12.8 Hz, 7H), 1.99 (d, J=12.3 Hz, 2H), 1.72 (tt, J=12.0, 6.1 Hz, 2H), 1.29 (d, J=6.8 Hz, 6H).

LCMS: t=3.08 min, 591.2 (M+H⁺).

During preparation of the compound I-111, said 1-(4-amino-3-methoxyphenyl)-N,N-dimethylpiperidine-4-amine (compound 5) was synthesized by a route below

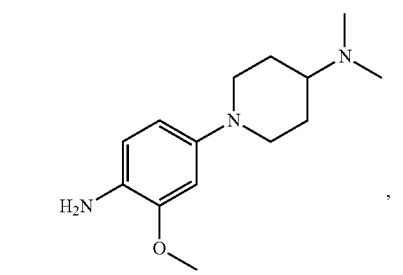

,

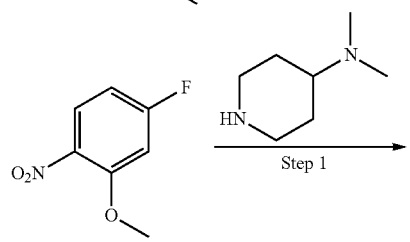

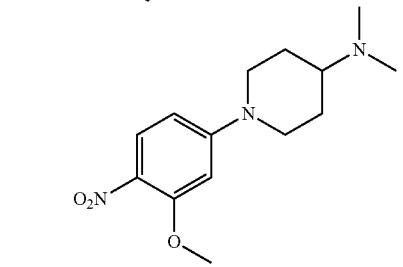

5

Step 1 Preparation of 1-(3-methoxy-4-nitrophenyl)-N,N-dimethylpiperidine-4-amine

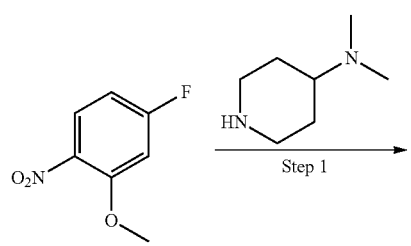

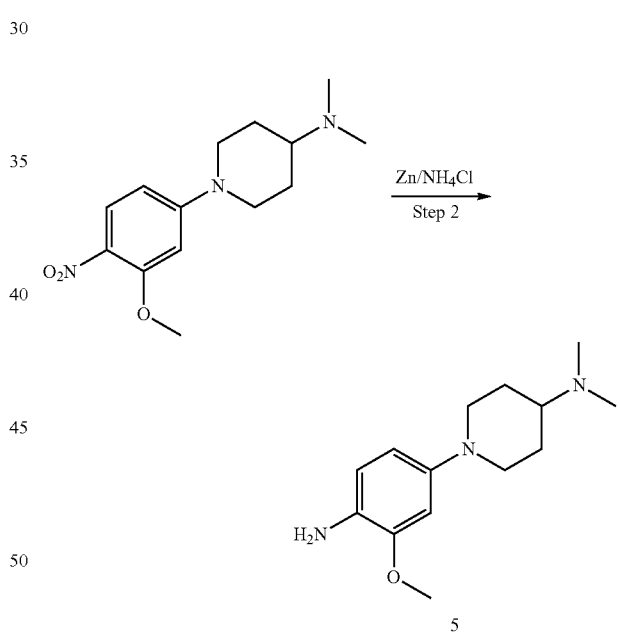

To a 100 mL flask was added compound 4-fluorine-2-methoxy-1-nitrobenzene (5 g, 29.2 mmol), N,N-dimethyl-piperidine-4-amine hydrochloride (5.88 g, 29.2 mmol) and potassium carbonate (12.11 g, 88 mmol), and then added with 60 mL DMF. The mixture was heated to 80° C. and stirred overnight. After TLC indicated the reaction was completed, the mixture was cooled to room temperature, diluted with water and extracted with ethyl acetate twice. The combined organic phase was washed with saturated aqueous sodium chloride, dried over anhydrous sodium sulfate, concentrated to remove solvent to give a brown oily product (5 g, yield 80%).

LCMS: t=0.48 min, 280.1 (M+H⁺).

Step 2 Preparation of 1-(4-amino-3-methoxyphenyl)-N,N-dimethylpiperidine-4-amine To methanol (10 mL) was added compound 1-(3-methoxy-4-nitrophenyl)-N,N-dimethylpiperidine-4-amine (6.5 g, 23.27 mmol), and then added with ammonium chloride (0.410 g, 7.67 mmol). Zinc powder (15.21 g, 233 mmol) was added in portions under stirring at room temperature, and the mixture was refluxed under heating for 3 hours. After TLC indicated the reaction was completed, the mixture was cooled to room temperature, filtered, evaporated to dryness and dissolved with DCM. The resulting mixture was further washed with saturated sodium bicarbonate, dried over anhydrous sodium sulfate, filtered and concentrated to give a brown oily product, compound 5 (5 g. yield 86%).

¹H NMR (400 MHz, dmso): δ 6.47 (d, J=8.4 Hz, 1H), 6.45 (d, J=2.4 Hz, 1H), 6.26 (dd, J=8.4, 2.4 Hz, 1H), 4.17 (s, 2H), 3.70 (s, 3H), 3.38 (d, J=12.4 Hz, 4H), 2.16 (s, 6H), 2.08 (s, 1H), 1.78 (d, J=12.4 Hz, 2H), 1.45 (dd, J=11.6, 3.6 Hz, 2H).

LCMS: t=0.43 min, 250.1 (M+H⁺).

During preparation of the compound 5, said 2-chloro-5-(2-fluorinemethoxy)-N-(2-(isopropylsulfonyl) phenyl) pyrimidine-4-amine (compound 12) was synthesized by a route below:

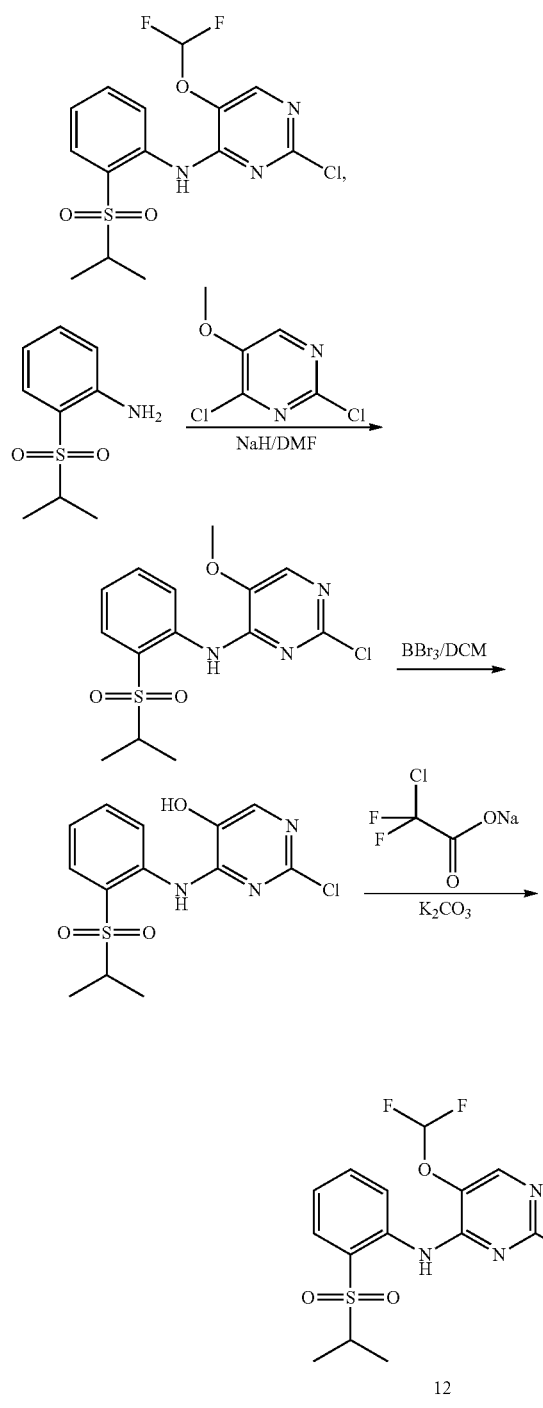

Step 1 Preparation of 2-chloro-N-(2-(isopropylsulfonyl) phenyl)-5-methoxypyrimidine-4-amine To anhydrous DMF (25 mL) was added 2-isopropylsulfonyl aniline (2 g, 10.04 mmol), and the mixture was cooled to 0° C. in an ice bath. NaH (1.806 g, 60.2 mmol, 80%) was added in portions under nitrogen atmosphere, and the mixture was stirred at 0° C. for 1 hour, during which a solution of 2,4-dichloro-5-methoxypyrimidine (10.78 g, 60.2 mmol) in DMF (10 mL) was added. The mixture was warmed to room temperature slowly and stirred for additional 10 hours, and then cooled to 0° C. in an ice bath again. The mixture was quenched with ice water, and then extracted with ethyl acetate and washed with water and saturated aqueous sodium chloride. The resulting crude product was dried over anhydrous sodium sulfate, filtered and concentrated, and then further isolated purified by column chromatography (PE/EA=10:1 to 5:1) to give a white solid product (3.18 g, yield 90%).

LCMS: t=3.85 min, 342.0 (M+H⁺).

Step 2 Preparation of 2-chloro-4-((2-(isopropylsulfonyl) phenyl) amino) pyrimidine-5-phenol To anhydrous dichloromethane (25 mL) was added 2-chloro-4-((2-(isopropylsulfonyl) phenyl)-5-methoxypyrimidine-4-amine (2.5 g, 7.31 mmol), and the mixture was cooled to 0° C. in an ice bath. To the mixture was added boron tribromide (2.78 ml, 29.3 mmol) in dichloromethane (10 mL) drop wise. The mixture was further stirred for 5 hours, and then quenched with ice water, washed with saturated sodium bicarbonate and saturated aqueous sodium chloride. The resulting crude product was dried over anhydrous sodium sulfate, filtered and concentrated, and then further isolated and purified by column chromatography PE/EA (V/V=5:1 to 3:1) to give a white solid product (2.06 g, yield 77%).

LCMS: t=3.60 min, 328.0 (M+H⁺).

Step 3 Preparation of 2-chloro-5-(difluoromethoxy)-N-(2-(isopropylsulfonyl) phenyl) pyrimidine-4-amine To DMF/H₂O (5 mL/1.5 mL) was added 2-chloro-4-((2-(isopropylsulfonyl) phenyl) amino) pyrimidine-5-phenol (500 mg, 1.342 mmol), and then added with 2-chloro-2,2-sodium difluoroacetate (614 mg, 4.03 mmol) and K₂CO₃ (557 mg, 4.03 mmol). The mixture was heated to 120° C. under nitrogen atmosphere and stirred for 15 hours. After the reaction was completed, the mixture was cooled to room temperature, diluted with ethyl acetate (50 mL), and washed with water and saturated aqueous sodium chloride. The resulting crude product was dried over anhydrous sodium sulfate, filtered and concentrated, and then further isolated purified by column chromatography PE/EA (V/V=5:1 to 2:1) to give a white solid product (235 mg, yield 45%).

LCMS: t=4.00 min, 378.0 (M+H⁺).

Example 38 Preparation of 5-(difluoromethoxy)-N²-(4-(4-(dimethylamino) piperidin-1-yl)-2-methoxy-5-methylphenyl)-N⁴-(2-(isopropylsulfonyl) phenyl) pyrimidine-2,4-diamine (Compound I-112)

Preparation Scheme

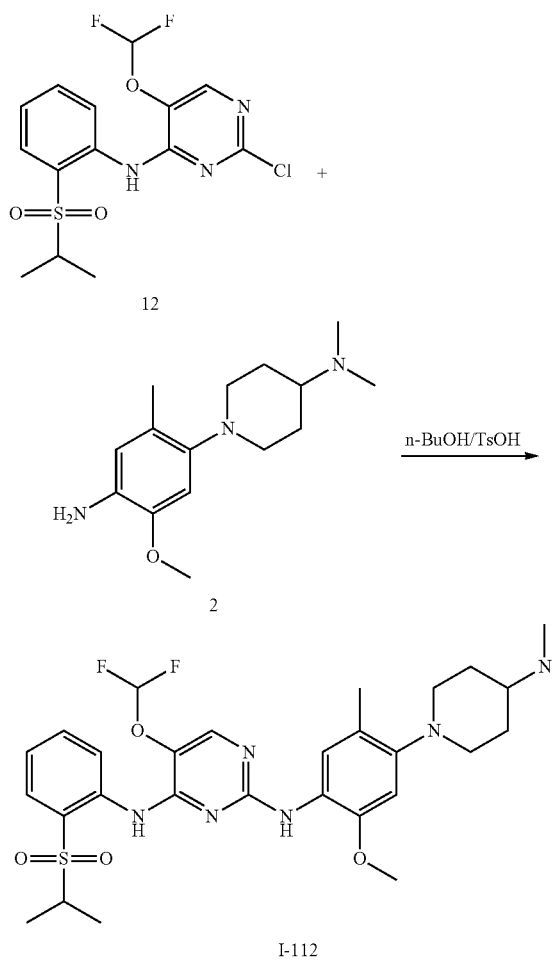

To n-BuOH (2.5 mL) was added intermediate 12 (200 mg, 529 mmol) and 1-(4-amino-5-methoxy-2-methylphenyl)-N,N-dimethylpiperidine-4-amine (compound 2) (139 mg, 529 mmol), and then added with p-toluenesulfonic acid (91 mg, 529 mmol). The mixture was heated to 120° C. and stirred for 3 hours. After LCMS indicated the reaction was completed, the mixture was cooled to room temperature, diluted with ethyl acetate (25 mL), and washed with water and saturated aqueous sodium chloride. The resulting crude product was dried over anhydrous sodium sulfate, filtered and concentrated, and then further isolated by column chromatography (DCM/MeOH (v/v=40:1 to 20:1)) to give an off-white solid product, compound I-112 (64 mg, yield 20%).

$^1$H NMR (400 MHz, CDCl$_3$): δ 9.56 (s, 1H), 8.67 (d, J=8.4 Hz, 1H), 8.06 (d, J=12.8 Hz, 2H), 7.87 (d, J=7.2 Hz, 1H), 7.60 (t, J=7.2 Hz, 1H), 7.38 (s, 1H), 7.21 (t, J=7.6 Hz, 1H), 6.58 (d, J=144 Hz, 1H), 6.58 (s, 2H), 3.85 (s, 3H), 3.23-3.20 (m, 3H), 2.82-2.59 (m, 8H), 2.21 (d, J=11.2 Hz, 2H), 2.17 (s, 3H), 1.90 (dd, J=21.2, 9.2 Hz, 3H), 1.28 (d, J=6.8 Hz, 6H).

LCMS: t=3.05 min, 605.2 (M+H⁺).

Example 39 Preparation of 5-(difluoromethoxy)-N²-(4-(4-(dimethylamino) piperidin-1-yl)-2-isopropoxy phenyl)-N⁴-(2-(isopropylsulfonyl) phenyl) pyrimidine-2,4-diamine (Compound I-113)

Preparation Scheme

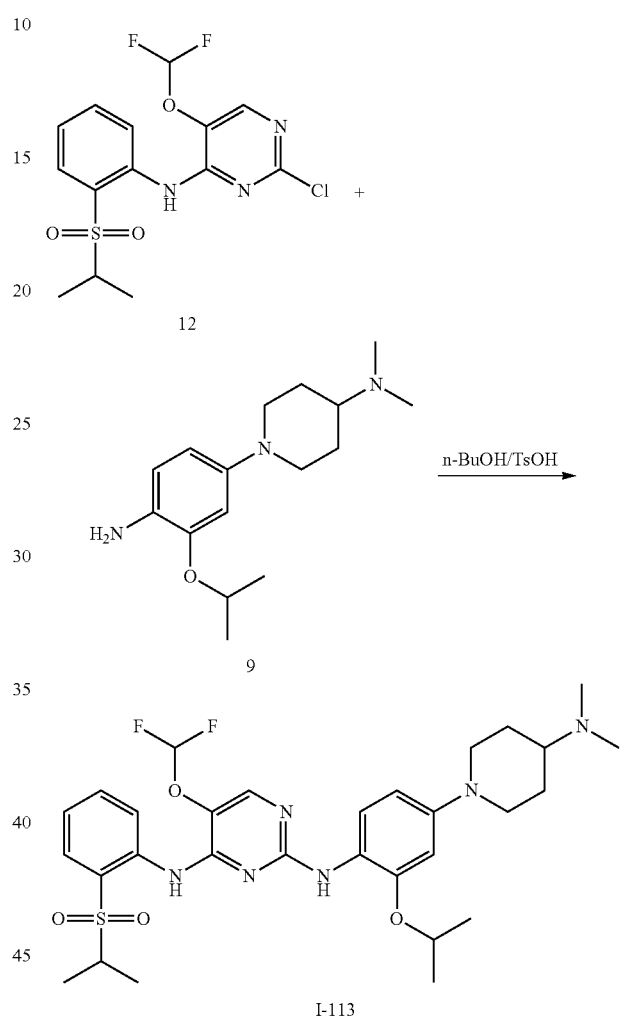

To n-butanol (1.5 mL) was added intermediate 12 (150 mg, 397 mmol) and 1-(4-amino-3-isopropoxyphenyl)-N,N-dimethylaminopiperidine-4-amine (compound 9) (110 mg, 397 mmol), and then added with p-toluenesulfonic acid (68 mg, 397 mmol). The mixture was heated to 120° C. and stirred for 3 hours. After LCMS indicated the reaction was completed, the mixture was cooled to room temperature, diluted with ethyl acetate (25 mL), and washed with water and saturated aqueous sodium chloride. The resulting crude product was dried over anhydrous sodium sulfate, filtered and concentrated, and then further isolated by column chromatography (DCM/MeOH (v/v=−40:1 to 20:1)) to give a light green solid, compound I-113 (54 mg, yield 22%).

$^1$H NMR (400 MHz, CDCl$_3$): δ 9.57 (s, 1H), 8.70 (d, J=8.4 Hz, 1H), 8.11 (d, J=8.8 Hz, 1H), 8.07 (s, 1H), 7.87 (d, J=8.0 Hz, 1H), 7.60 (s, 1H), 7.38 (s, 1H), 7.22 (t, J=7.6 Hz, 1H), 6.67 (d, J=72.2 Hz, 1H), 6.54 (s, 1H), 6.48 (d, J=8.8 Hz,

1H), 4.75-4.40 (m, 2H), 3.66 (d, J=12.0 Hz, 2H), 3.21 (d, J=6.8 Hz, 1H), 2.73 (t, J=12.0 Hz, 2H), 2.65 (s, 6H), 2.18 (d, J=12.0 Hz, 2H), 1.87 (d, J=9.6 Hz, 2H), 1.37 (d, J=8.0 Hz, 6H), 1.29 (d, J=6.8 Hz, 6H).

LCMS: t=3.94 min, 619.0 (M+H$^+$).

Example 40 Preparation of 5-chloro-N$^2$-(2-(difluoromethoxy)-4-(4-(dimethylamino) piperidin-1-yl) phenyl)-N$^4$-(2-(isopropoxysulfonyl) phenyl) pyrimidine-2,4-diamine (Compound I-114)

Preparation Scheme

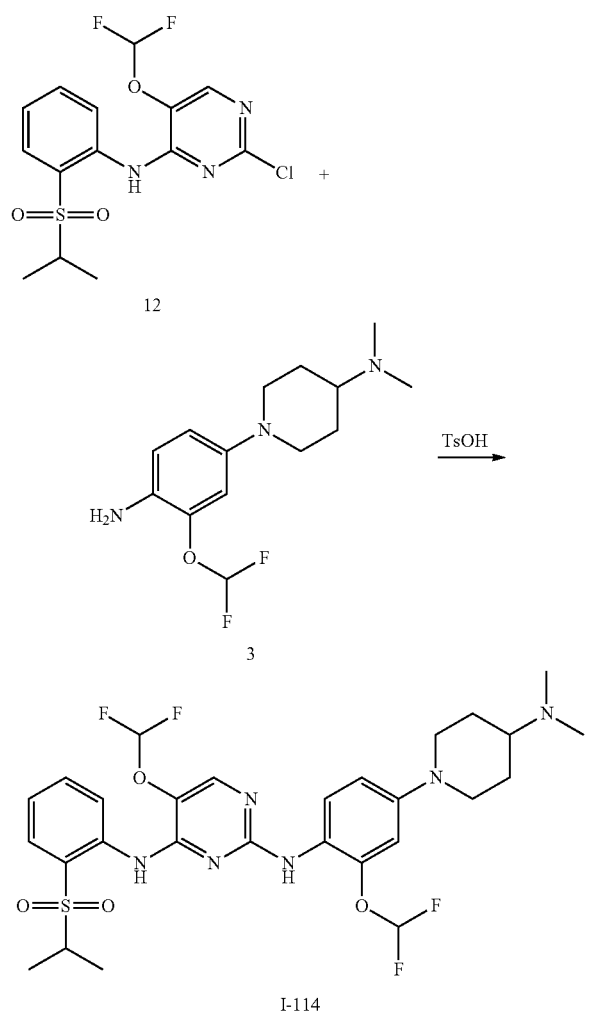

To n-butanol (1.5 mL) was added intermediate 12 (150 mg, 397 mmol) and 1-(4-amino-3-(difluoromethoxy) phenyl)-N,N-dimethylpiperidine-4-amine (compound 3) (113 mg, 397 mmol), and then added with p-toluenesulfonic acid (68 mg, 397 mmol). The mixture was heated to 120° C. and stirred for 3 hours. After LCMS indicated the reaction was completed, the mixture was cooled to room temperature, diluted with ethyl acetate (25 mL), and washed with water and saturated aqueous sodium chloride. The resulting crude product was dried over anhydrous sodium sulfate, filtered and concentrated, and then further isolated by column chromatography (DCM/MeOH (v/v=40:1 to 20:1)) to give a white solid product, compound I-114 (64 mg, yield 25.7%).

$^1$H NMR (400 MHz, CDCl$_3$): δ 9.63 (s, 1H), 8.63 (d, J=8.4 Hz, 1H), 8.07 (s, 1H), 8.03 (d, J=9.2 Hz, 1H), 7.86 (d, J=8.0 Hz, 1H), 7.57 (t, J=8.0 Hz, 1H), 7.21 (t, J=7.6 Hz, 1H), 7.01 (s, 1H), 6.77 (dd, J=8.8, 2.8 Hz, 1H), 6.73 (s, 1H), 6.58-6.31 (m, 2H), 6.54 (d, J=37.6 Hz, 1H), 6.35 (d, J=39.2 Hz, 1H), 3.67 (d, J=12.4 Hz, 2H), 3.20 (dd, J=13.6, 6.8 Hz, 1H), 2.73 (t, J=11.6 Hz, 2H), 2.42 (s, 6H), 2.03 (d, J=11.6 Hz, 2H), 1.71 (dd, J=20.8, 11.6 Hz, 2H), 1.29 (d, J=6.8 Hz, 6H).

LCMS: t=3.62 min, 627.2 (M+H$^+$).

Example 41 Preparation of 5-(difluoromethoxy)-N$^2$-(4-(4-isopropylpiperazin-1-yl)-2-methoxy-5-methylphenyl)-N$^4$-(2-(isopropylsulfonyl) phenyl) pyrimidine-2,4-diamine (Compound I-115)

Scheme

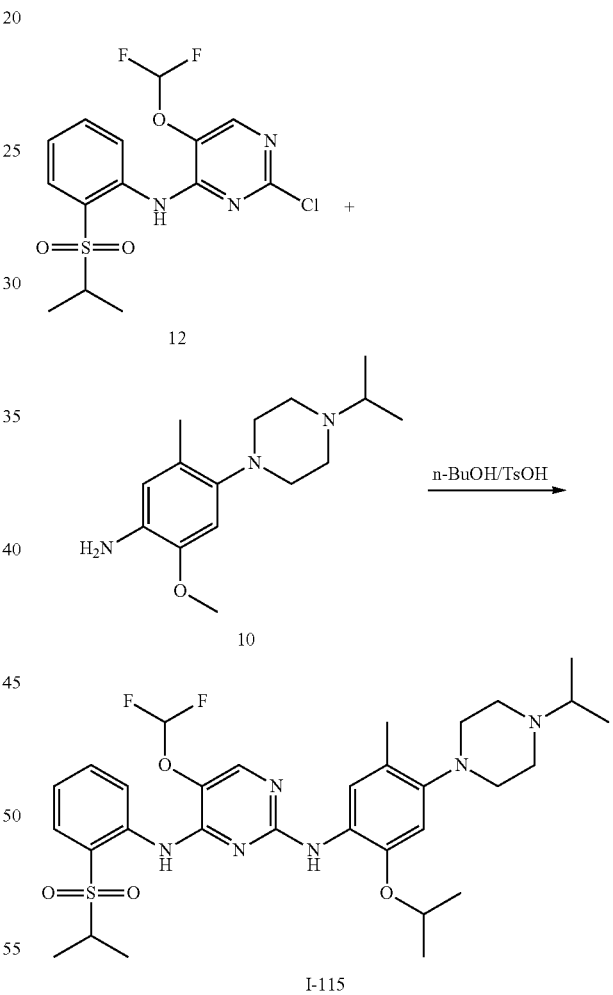

To n-BuOH (2.5 mL) was added compound 12 (150 mg, 397 mmol) and 4-(4-isopropylpiperazin-1-yl)-2-methoxy-5-methylaniline (compound 10) (105 mg, 397 mmol), and then added with p-toluenesulfonic acid (68 mg, 397 mmol). The mixture was heated to 120° C. and stirred for 3 hours. After LCMS indicated the reaction was completed, the mixture was cooled to room temperature, diluted with ethyl acetate (25 mL), and washed with water and saturated aqueous sodium chloride. The resulting crude product was dried over anhydrous sodium sulfate, filtered and concentrated, and then further isolated by column chromatography (DCM/MeOH (v/v=40:1 to 20:1)) to give a white solid product, compound I-115 (42 mg, yield 17.5%).

$^1$H NMR (400 MHz, CDCl$_3$): δ 9.57 (s, 1H), 8.68 (d, J=8.0 Hz, 1H), 8.10 (s, 2H), 7.89 (dd, J=8.0, 1.6 Hz, 1H), 7.69-7.59 (m, 1H), 7.43 (s, 1H), 7.24-7.13 (m, 1H), 6.80-6.37 (m, 3H), 3.88 (s, 3H), 3.57-2.75 (m, 10H), 2.19 (s, 3H), 1.30 (d, J=6.8 Hz, 6H).

LCMS: t=3.42 min, 605.3 (M+H$^+$).

Example 42

Compound I-110 was synthesized with the method similar to that of Example 36.

Example 43

Inhibition of Compound I Against ALK Kinase Activity

All compounds prepared by the above examples were assayed as described hereinafter for inhibition of ALK kinase activity, indicated by IC$_{50}$, corresponding to the concentration at which the ALK kinase activity is suppressed by 50%.

Abbreviation and Definition

Mg milligram
mL milliliter
μg microgramme
μl microlitre
mM millimole per liter
EDTA ethylenediamine tetraacetic acid
DMSO dimethylsulfoxide
SD standard deviation
SOP Standard Operating Procedure
Materials:
ALK (Carna, Cat. No 08-105, Lot. No. 08CBS-0112)
ALK L1196M (Carna, Cat. No 08-529, Lot. No. 11CBS-1134)
Peptide FAM-P22 (GL Biochem, Cat. No. 112393, Lot. No. P080401-XY112393)
ATP (Sigma, Cat. No. A7699-1 G, CAS No. 987-65-5)
DMSO (Sigma, Cat. No. D2650, Lot. No. 474382)
EDTA (Sigma, Cat. No. E5134, CAS No. 60-00-4)
96-well plate (Corning, Cat. No. 3365, Lot. No. 22008026)
384-well plate (Corning, Cat. No. 3573, Lot. No. 12608008)
Staurosporine (Sigma. Cat. No. S4400-1MG, Lot. No. 046K4080)

Experiment Protocol

I. Preparation of 1× kinase buffer and stop buffer
1) 1× Kinase Buffer
50 mM HEPES. pH 7.5
0.0015% Brij-35
10 mM MgCl$_2$
2 mM DTT
2) stop buffer
100 mM HEPES, pH 7.5
0.015% Brij-35
0.2% Coating Reagent #3
50 mM EDTA 2. Prepare a Compound Solution to be Tested Step 2.1 Dilute the compound to 50× of the final desired highest inhibitor concentration in reaction by 100% DMSO. Transfer 100 μl of this compound dilution to a well in a 96-well plate. For example, if desired highest inhibitor concentration is 1 μM, then prepare 50 μM of compound DMSO solution in this step.

Step 2.2 Further dilute said compound dilution by 3-fold in series, thus obtain 10 concentrations.

Step 2.3 Add 100 μl of 100% DMSO to two empty wells for no compound control and no enzyme control in the same 96-well plate. Mark the plate as source plate.

Step 2.4 Prepare an intermediate plate

Transfer 10 μl of each compound from the source plate to a new 96-well plate as the intermediate plate.

Add 90 μl of 1× kinase buffer to each well of the intermediate plate. Mix the compounds in the intermediate plate for 10 min on a shaker.

3 Prepare an Assay Plate

Transfer 5 μl of each well from the 96-well intermediate plate to a 384-well plate in duplicate. For example, A1 of the 96-well plate is transferred to A1 and A2 of the 384-well plate. A2 of the 96-well plate is transferred to A3 and A4 of the 384-well plate, and so on.

4. Kinase Reaction
4.1 Prepare a 2.5× kinase solution
Add kinase in 1× kinase base buffer, thus obtain the 2.5× kinase solution.
4.2 Prepare a 2.5× peptide solution
Add FAM-labeled peptide and ATP in the 1× kinase base buffer, thus obtain the 2.5× substrate solution.
4.3 In each well of the assay plate obtained in step 3, there was 5 μL of the compound in 10% DMSO.
4.4 Transfer the 2.5× enzyme solution to the assay plate.
4.5 Incubate at room temperature for 10 min.
4.6 Transfer the 2.5× peptide solution to the assay plate.
4.7 Kinase reaction and stop
Incubate at 28° C. for 20 min.
Add 25 μl of stop buffer to stop reaction.
5. Caliper Reading
Conversion rate of the kinase was read via the Caliper.
6. Curve-Fitting
6.1 Copy conversion data from Caliper program.
6.2 Convert conversion values to inhibition values with the following formula:

Percent inhibition=(max−conversion)/(max−min)*100 where "max" stands for DMSO control; and "min" stands for low control.

6.3 Fit the data in XLfit excel add-in version 4.3.1 and obtain IC$_{50}$ values according to the following formula:

Y=Bottom+(Top−Bottom)/(+10^((Log IC$_{50}$−X)*HillSlope)).

The biochemical activities of the present compounds were determined via the above tests, and the IC$_{50}$ values of compounds were listed in Table 1.

Note: In terms of the ALK inhibition activity. "A" means the IC$_{50}$ value of compound is below 1 nM; "B" means the IC$_{50}$ value of the compound is 1 nM to 10 nM; and "C" means the IC$_{50}$ value of the compound is above 10 nM. In terms of the ALK L1196M inhibition activity, "a" means the IC$_{50}$ value of the compound is below 1 nM; "b" means the IC$_{50}$ value of the compound is 1 nM to 10 nM; and "c" means the IC$_{50}$ value of the compound is above 10 nM.

TABLE 1

| Compound No. | ALK Inhibition activity $IC_{50}$ (nM) | ALK L1196M Inhibition activity $IC_{50}$ (nM) |
| --- | --- | --- |
| I-1 | A | a |
| I-2 | A | a |
| I-3 | A | a |
| I-4 | B | b |
| I-5 | B | b |
| I-6 | B | b |
| I-7 | B | b |
| I-8 | A | a |
| I-9 | B | b |
| I-10 | B | b |
| I-11 | B | b |
| I-12 | B | b |
| I-13 | A | a |
| I-14 | A | a |
| I-15 | A | a |
| I-16 | A | a |
| I-17 | B | b |
| I-18 | B | b |
| I-23 | B | b |
| I-80 | B | b |
| I-82 | A | a |
| I-84 | B | b |
| I-85 | B | b |
| I-86 | A | a |
| I-88 | B | b |
| I-89 | B | a |
| I-90 | B | b |
| I-91 | B | b |
| I-92 | B | b |
| I-95 | A | a |
| I-98 | A | a |
| I-100 | B | b |
| I-102 | B | a |
| I-103 | B | a |
| I-107 | A | b |
| I-109 | B | b |
| I-110 | B | b |
| I-111 | A | a |
| I-112 | A | a |
| I-113 | A | a |
| I-114 | A | a |
| I-115 | A | a |

The results shows that all the compounds represented in formula I inhibit ALK kinase and ALKL1196M kinase significantly, demonstrating that the present compounds can be all used as an ALK inhibitor for treating a tumor related to activity of anaplastic lymphoma kinase (ALK), particularly be used in preparation of an anti-tumor medicament for treating anaplastic lymphoma kinase (ALK).

Example 44 Suppression of the Compound I Against Karpas299 Cell Proliferation

1. Assay Principle

As the amount of ATP can indicate the number of living cells directly, the living cells in culture are able to be quantified by determining the ATP level. In our experiment, we use a living-cell testing kit to quantify the living cells, which utilizes UltraGlow luciferase to generate a stable glow signal in the presence of ATP which is produced by metabolism of living cells, such as respiration. Specifically, a reagent CellTiter-Glo™ was added into cell culture media, and then the luminescent intensity was determined to measure proliferation of cells, as the luminescent intensity is in direct proportion to the ATP level which correlates positively to the number of living cells. The test plate was tested with the Envision (PE).

2. Materials

Cell media: RPMI-1640 medium, fetal calf serum (FCS), antibiotics (Penicillin-Streptomycin)

Cell line: Karpas299

Assay reagent: Cell Viability Assay Kit CellTiter-Glo

Others: a 96-well plate, a 384-well plate, DMSO

3. Experiment Protocol

Step 3.1 Culturing test cells

Karpas 299 cells were plated into a black 384-well plate, with 2500 cells in 45 μl cell suspension per well. The plate was placed in a carbon dioxide incubator overnight.

Step 3.2 Preparation of the compounds to be tested

Step 3.2.1

Each compound to be tested was dissolved in DMSO at 10 mM as the stock solution, which was left in a nitrogen-gas tank for storage.

Step 3.2.2

After dilution of 10 μL stock solution (10 mM) into 2.5 mM as a starting working solution, 10 concentrations of the working solutions from 5 μM to 0.25 nM were obtained in duplicate by further dilution in 3-fold series with ECHO.

Step 3.3 Mixing the compound with the test cells

To each well of a new 96-well plate were added 49 μl medium and 1 μl of the compounds to be tested at individual working concentrations (10 concentrations in total). After oscillation, 5 μl of mixture in each well of the 96-well plate was transferred into corresponding wells in the 384-well plate in the step 3.1. The 384-well plate was incubated in the carbon dioxide incubator for 3 days.

Step 3.4 Assay

To each well of the 384-well plate was added 25 pd reagent Promega CellTiter-Glo. and incubated at room temperature for 10 minutes to stabilize the luminescence signal. The results were read with the PerkinElmer Envision Multimode Plate Reader.

Table 2 shows that the present compounds suppress proliferation of Karpas299 cells. It should be noted that in the results of Table 2, "D" means the $IC_{50}$ value of the compound is below 50 nM; the "E" means $IC_{50}$ value of the compound is 50 nM to 100 nM; and "F" means the $IC_{50}$ value of the compound is above 50 nM.

TABLE 2

| Compound No. | Inhibition activity on Karpas299 cells $IC_{50}$ (nM) |
| --- | --- |
| I-1 | D |
| I-2 | D |
| I-3 | D |
| I-4 | D |
| I-5 | D |
| I-6 | D |
| I-7 | D |
| I-8 | D |
| I-9 | D |
| I-10 | D |
| I-11 | D |
| I-12 | E |
| I-13 | D |
| I-14 | D |
| I-15 | E |
| I-16 | D |
| I-17 | D |
| I-18 | D |
| I-23 | D |
| I-80 | D |
| I-82 | D |
| I-84 | D |
| I-85 | D |
| I-86 | D |

TABLE 2-continued

| Compound No. | Inhibition activity on Karpas299 cells IC$_{50}$ (nM) |
|---|---|
| I-88 | E |
| I-89 | E |
| I-90 | D |
| I-91 | E |
| I-92 | E |
| I-95 | D |
| I-98 | D |
| I-100 | D |
| I-102 | E |
| I-103 | E |
| I-107 | E |
| I-109 | E |
| I-110 | D |
| I-111 | D |
| I-112 | D |
| I-113 | D |
| I-114 | D |
| I-115 | D |

It shows that all the compounds represented in formula I inhibit the ALK kinase significantly, and suppress the proliferation of Karpas 299 cells potently.

Example 45 Suppression of the Compound I Against Ba/F3 EML4-ALK Cell Proliferation 1. Materials
Cell media: RPMI-1640 medium, fetal calf serum (FCS), antibiotics (Penicillin-Streptomycin), IL-3, puromycin
Cell line: Ba/F3 EML4-ALK
Assay reagent: Cell Viability Assay Kit Celliter-Glo
Others: a 96-well plate, a 384-well plate, DMSO
2. Assay Principle
As the amount of ATP can indicate the number of living cells directly, the living cells in medium are able to be quantified by determining the ATP level. In our experiment, we use a cell viability assay kit to quantify the living cells, which utilizes UltraGlow luciferase to generate a stable glow signal in the presence of ATP which is produced by metabolism of living cells, such as respiration. Specifically, a reagent CellTiter-Glo™ was added into cell culture media, and then the luminescent intensity was determined to measure proliferation of cells, as the luminescent intensity is in direct proportion to the ATP level which correlates positively to the number of living cells. The test plate was assayed by the Envision (PE).
3. Experiment Protocol
Step 3.1 Culturing test cells
Ba/F3 EML4-ALK cells were planted into a 384-well plate, with almost 300 cells per well. The plate was placed in a carbon dioxide incubator overnight.
Step 3.2 Preparation of the compounds to be tested
10 concentrations of the working solutions were obtained in duplicate by dilution in 3-fold series with BRAVO.
Step 3.3 Mixing the compound to be tested with the test cells
The compounds to be tested at individual working concentrations were transferred into corresponding wells in the 384-well plate in the step 3.1, with 5 µM as the initial working concentration, and then the 384-well plate was incubated in the carbon dioxide incubator for 3 days.
4. Assay
To each well of the 384-well plate was added the reagent Promega CellTiter-Glo, and incubated at room temperature for 10 minutes to stabilize the luminescence signal. The results were read by the PerkinElmer Envision Multi-mode Plate Reader.

Table 3 shows that the present compounds suppress proliferation of the Ba/F3 EML4-ALK cells.

It should be noted that in the results of Table 3, "d" means the IC$_{50}$ value of the compound is below 20 nM; "e" means the IC$_{50}$ value of the compound is 20 nM to 100 nM; and "f" means the IC$_{50}$ value of the compound is above 100 nM.

TABLE 3

| Compound NO. | Ba/F3 EML4-ALK (IC$_{50}$ nM) |
|---|---|
| I-1 | d |
| I-2 | d |
| I-3 | d |
| I-4 | d |
| I-5 | d |
| I-6 | d |
| I-7 | d |
| I-8 | d |
| I-9 | e |
| I-10 | d |
| I-11 | d |
| I-12 | d |
| I-13 | d |
| I-14 | d |
| I-15 | d |
| I-16 | d |
| I-17 | d |
| I-18 | d |
| I-23 | d |
| I-80 | e |
| I-82 | e |
| I-84 | e |
| I-85 | e |
| I-86 | d |
| I-88 | e |
| I-89 | d |
| I-90 | d |
| I-91 | d |
| I-92 | d |
| I-95 | e |
| I-98 | e |
| I-100 | e |
| I-102 | d |
| I-103 | d |
| I-107 | e |
| I-109 | d |
| I-110 | d |
| I-111 | d |
| I-112 | d |
| I-113 | d |
| I-114 | d |
| I-115 | d |

It shows that all the compounds represented in formula I suppress the proliferation of Ba/F3 EML4-ALK 299 cells potently.

Example 46 Dynamic Solubility

In the medicament screening stage, dynamic solubility of candidate compounds was assayed for high throughput screening, and results exhibiting higher solubility would help to provide more reliable evidence in vitro and in vivo. The pH value of aqueous phase to be tested was always specified to be pH 7.4, which was equal to the pH value of body fluid, owing to the pH-dependence of dynamic solubility.
Protocol:
A quantified compound was dissolved with 100% DMSO at a final concentration of 10 mM, 10 µL of the test compound and a control compound (10 mM in DMSO) each were added into individual wells (490 µL buffer/well) of a 96-well plate. Afterwards, the 96-well plate was oscillated for 2 minutes, and incubated in the oscillator at a temperature of 22±2° C. for 24 hours. 200 µL of the test solution was transferred to a MultiScreen filter plate which is a polycarbonate membrane, and filtered with a millipore vacuum manifold to give the filtrate, which was further measured with the HPLC-UV detector. Three concentrations of UV-standards and the test compound were detected simultaneously in duplicate, and then the average concentration of the test compound was calculated via a standard curve.

It shows that the present compounds are more water-soluble than the controls (crizotinib and Ceritinib LDK378).

Example 47 Metabolic Stability In Vitro

Clearance rate of compound in phase I reaction was evaluated in metabolic stability assay in vitro, and based on the clearance rate its intrinsic clearance rate in hepatocyte in vivo was predicted. The metabolic stabilities of the present compounds in liver microsomes of human and rat were evaluated in metabolic stability assay in vitro. The controls are crizotinib and Ceritinib LDK378.

Materials:
1. Compounds to be tested
2. Buffer medium: 100 nM Potassium phosphate buffer, PH 7.4; 10 mM $MgCl_2$
3. Stop buffer: A solution of 100 ng/mL Tolbutamide and 100 ng/mL Labetalol (as internal standards) in cooled cyanomethane (CAN)

Protocol:
1. Diluting compounds to be tested
   1.1 Preparing an intermediate solution
   5 µL stock solution of the compound to be tested (10 mM) or 5 µL stock solution of the control (10 mM in DMSO) was diluted with 45 µL DMSO, and then further diluted with 450 µL 1:1 methanol/$H_2O$ (Conc.: 100 µM, 45% methanol).
   1.2 Preparing a working solution
   50 µL of the intermediate solution obtained in step 1.1 was diluted with 450 µL of Potassium phosphate buffer (100 mM) (Conc.: 10 µM, 4.5% methanol).
2. Testing
   2.1 10 µL working solution (10 µM) was added into each well of a 96-well plate with a liquid platform.
   2.2 80 µL of liver microsomal solution (0.625 mg/mL) was added into individual wells obtained in the step 2.1 with the liquid platform, with a final concentration of 0.5 mg/mL.
   2.3 The 96-well plate containing the compound and the microsome was preheated at 37° C. for 10 minutes.
   2.4 To the 96-well plate without the NADPH cofactor obtained in the step 2.3, each well was added with 10 µL potassium phosphate buffer (100 mM), and then stilled for 60 minutes, after which 300 µL CAN stop buffer containing 100 ng/mL Tolbutamide was added, thus obtaining a control sample.
   2.5 To other 96-well plates obtained in the step 2.3, each well was added with 10 µL of the NADPH cofactor solution containing 1 mM NADP, 1 mM magnesium chloride, 6.5 mM Isocitric acid and 1 unit/mL isocitrate dehydrogenase to initiate the metabolic reaction. For a 0-minute plate, prior to adding the liver microsomal solution and the NADPH cofactor solution, 300 µL CAN stop buffer was added, thus obtaining experimental results not undergone the metabolic reaction.
   2.6 For 5-minute, 10-minute, 20-minute, 30-minute and 60-minute plates, 300 µL CAN stop buffer containing 100 ng/mL Tolbutamide was added at the time of 5 minutes, 10 minutes, 20 minutes. 30 minutes and 60 minutes to stop the metabolic reaction.
   2.7 The plates were oscillated sufficiently, and then centrifuged at 4000 rpm for 20 minutes.
   2.8 100 µL of supernatant was mixed with 300 µL purified water, thus obtaining a test sample.
   2.9 The test samples obtained in the step 2.8 were analyzed with the LC-MS/MS detector.

The parameters such as half-life period, clearance rate and intrinsic clearance rate of the compound were calculated by the first-order kinetic equation.

It shows that the present compounds have outstanding metabolic stability, thereby supporting the pre-clinical research robustly.

Example 48 Caco-2 Cell Assay

Caco-2 cells, which are human colonic cancer cells, are wildly used as a model in vitro to study the absorption rate on small intestine. The monolayer of Caco-2 cell has been generally applied to evaluate the passive diffusion and active transport during the intestinal absorption. In our disclosure, the membrane permeability of the compounds was evaluated via Caco-2 cell monolayer model in the presence of GF120918A, a strong inhibitor of efflux transporter including Pglycoprotein (P-gp) and breast cancer resistance protein (BCRP), and the absorption of the compounds on the small intestine was predicted. The controls are crizotinib and Ceritinib (LDK378).

Protocol:
For assay of AP side to BL side direction, 2 µM of the compound solution (DMSO≤1%) was added into the apical side (AP side) of the Caco-2 cell monolayer model, and transport buffer HBSS (pH 7.4) was added into the basolateral side (BL side), and then the model was incubated at 37° C. and 5% $CO_2$ for 2 hours. Afterwards, the samples taken from the apical side and the basolateral side were each mixed with the cooled CAN stop buffer containing an internal standard, and then analyzed according to the LC/MS/MS method to measure apparent permeability coefficient and efflux rate of the compound. Alternatively, for BL side to AP side direction, the operation was the same as above, except that 2 µM of the compound solution was added into the BL side and the transport buffer HBSS was added into the AP side. The assay was conducted in duplicate.

It shows that the present compounds have better membrane permeability than those of controls, thus extending the bioavailability of pharmaceutical compositions.

In the description of this specification, the terms "one embodiment", "some embodiments", "examples", "specific examples" or "some examples" and the like are intended to be a combination of the specific features, structures, materials or characteristics described in connection with the embodiments or examples is included in at least one embodiment or example of the present disclosure. In the present specification, the schematic expression of the terminology described above does not necessarily refer to the same embodiment or example. Moreover, the particular feature, structures, materials, or characteristics described herein maybe combined in any suitable embodiment or example in any suitable manner.

Although the illustrated examples of the disclosure have been described, it should be understood that the examples described above are only exemplary and not be construed as limited to the examples of the disclosure. The changes, modifications, replacements and variations maybe made in present examples by the skilled person in the art within the scope of the present invention, without departing from the principles and purposes of the present invention.

What is claimed is:

1. A compound or a pharmaceutically acceptable salt, a hydrate, a solvate, a metabolite, or a prodrug thereof, wherein the compound is any one selected from

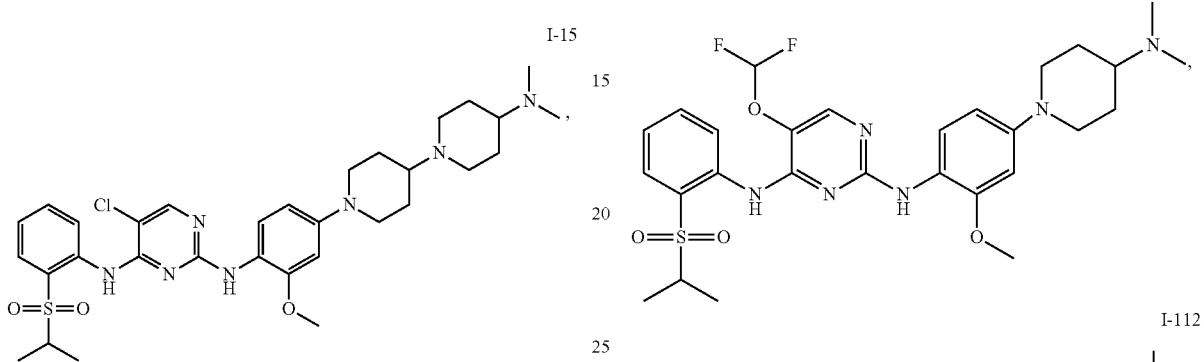

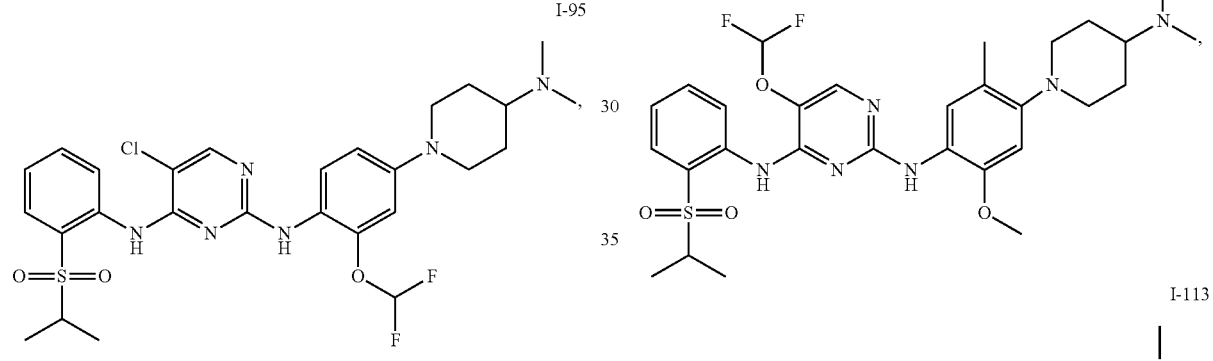

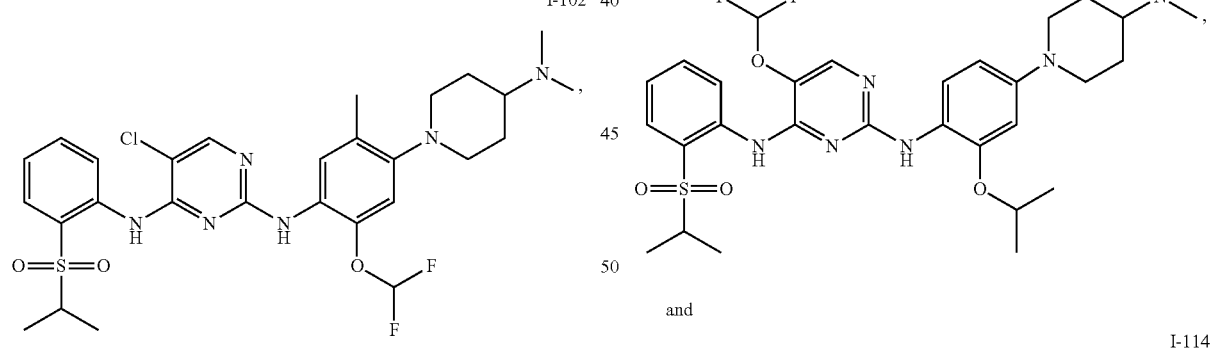

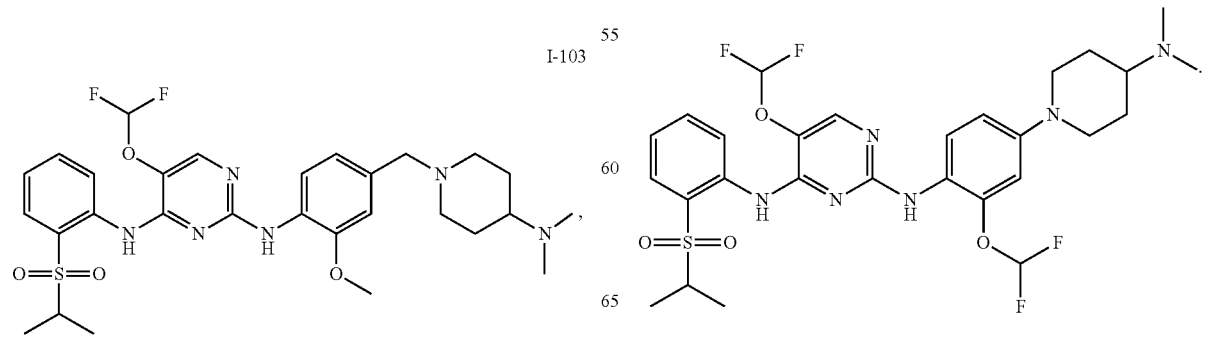

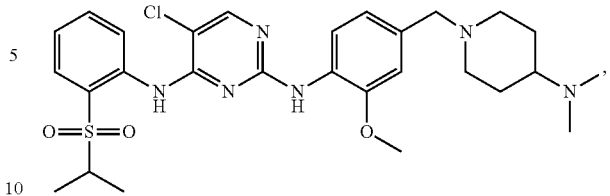

and

2. A pharmaceutical composition comprising the compound of claim 1.

3. The pharmaceutical composition according to claim 2, further comprising a second therapeutic agent, wherein said second therapeutic agent is useful in inhibiting kinase, treating or preventing a cancer or suppressing proliferation of cancer cells.

4. The pharmaceutical composition according to claim 2, further comprising a pharmaceutically acceptable carrier, excipient, diluent, auxiliary, vehicle, or combination thereof.

5. The pharmaceutical composition according to claim 4, wherein the pharmaceutical composition is in the form of tablets, capsules, injections, powder-injections, powders, syrups, solutions, suspensions or aerosols.

6. A method of treating a cancer, comprising administering to a subject in need thereof a therapeutically effective amount of the compound of claim 1, wherein the cancer is related to abnormal activity of anaplastic lymphoma kinase (ALK).

7. The method according to claim 6, wherein the cancer is lung cancer or anaplastic large cell non-Hodgkin lymphoma.

8. The method according to claim 7, wherein the lung cancer is non-small cell lung cancer.

9. A method of treating a cancer, comprising administering to a subject in need thereof a therapeutically effective amount of the pharmaceutical composition of claim 2, wherein the cancer is related to abnormal activity of anaplastic lymphoma kinase (ALK).

10. The method according to claim 9, wherein the cancer is lung cancer or anaplastic large cell non-Hodgkin lymphoma.

11. The method according to claim 10, wherein the lung cancer is non-small cell lung cancer.

12. The compound according to claim 1, wherein the compound is

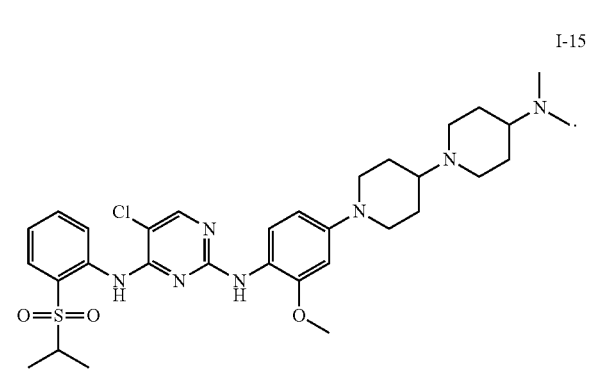 [SMILES: COc1cc(N2CCC(N3CCC(N(C)C)CC3)CC2)ccc1Nc1ncc(Cl)c(Nc2ccccc2S(=O)(=O)C(C)C)n1]

I-15

13. The compound according to claim 1, wherein the compound is

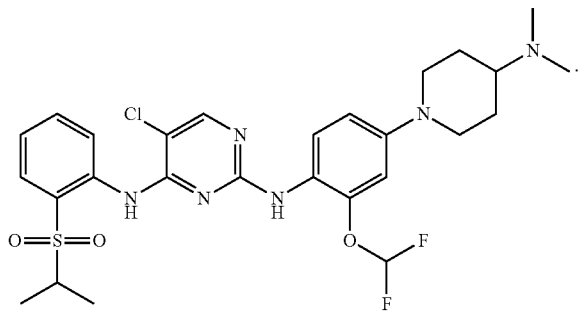

I-95

14. The compound according to claim 1, wherein the compound is

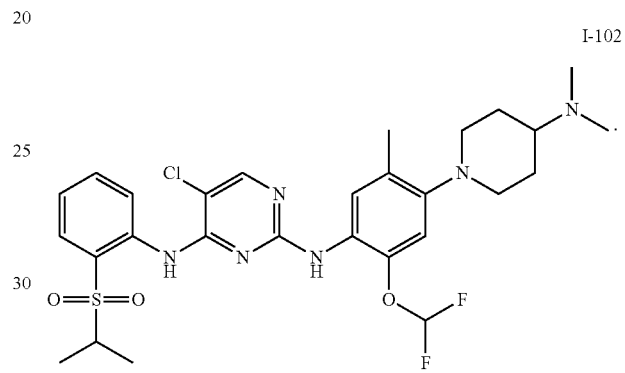

I-102

15. The compound according to claim 1, wherein the compound is

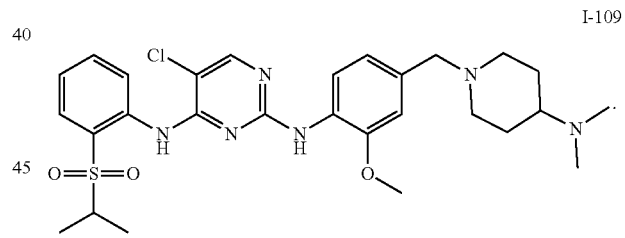

I-109

16. The compound according to claim 1, wherein the compound is

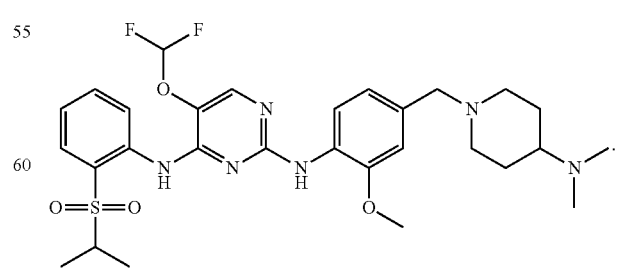

I-103

17. The compound according to claim 1, wherein the compound is

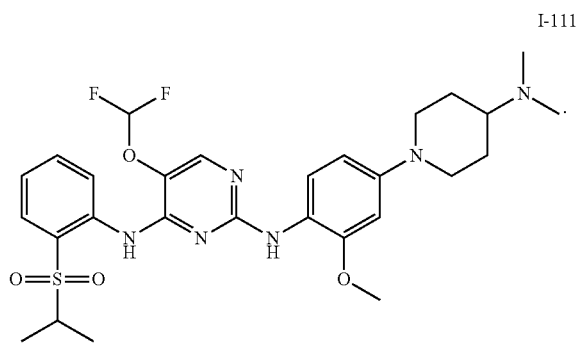 [SMILES: COc1cc(N2CCC(N(C)C)CC2)ccc1Nc1ncc(OC(F)F)c(Nc2ccccc2S(=O)(=O)C(C)C)n1]
I-111
18. The compound according to claim 1, wherein the compound is
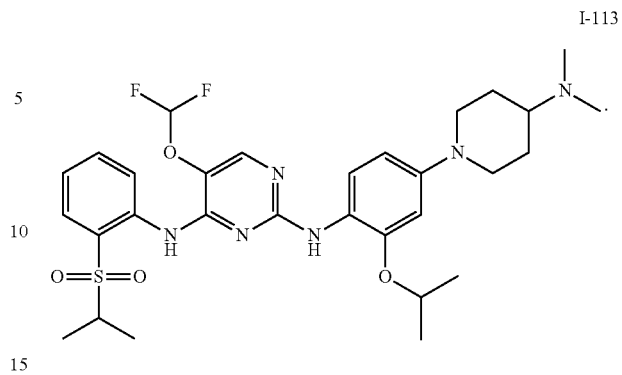
I-113
20. The compound according to claim 1, wherein the compound is
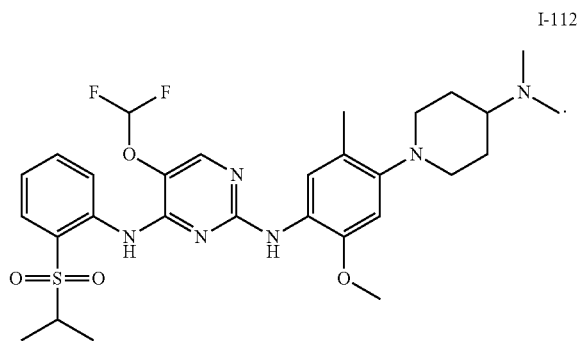 [SMILES: COc1cc(N2CCC(N(C)C)CC2)c(C)cc1Nc1ncc(OC(F)F)c(Nc2ccccc2S(=O)(=O)C(C)C)n1]
I-112
19. The compound according to claim 1, wherein the compound is
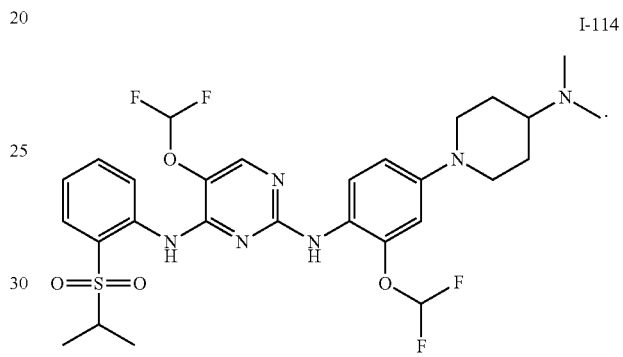
I-114
* * * * *